(12) United States Patent
Peviani et al.

(10) Patent No.: US 12,161,663 B2
(45) Date of Patent: Dec. 10, 2024

(54) COMPOSITIONS AND METHODS FOR TARGETING CELLS

(71) Applicants: Children's Medical Center Corporation, Boston, MA (US); Politecnico di Milano, Milan (IT); Dana-Farber Cancer Institute, Inc., Boston, MA (US)

(72) Inventors: Marco Peviani, Boston, MA (US); Alessandra Biffi, Boston, MA (US); Davide Moscatelli, Milan (IT); Umberto Capasso Palmiero, Milan (IT); Renato Auriemma, Milan (IT); Mattia Sponchioni, Milan (IT); Letterio Salvatore Politi, Milan (IT)

(73) Assignees: Children's Medical Center Corporation, Boston, MA (US); Politecnico di Milano, Milan (IT); Dana-Farber Cancer Institute, Inc., Boston, MA (US)

( * ) Notice: Subject to any disclaimer, the term of this patent is extended or adjusted under 35 U.S.C. 154(b) by 51 days.

(21) Appl. No.: 17/035,339

(22) Filed: Sep. 28, 2020

(65) Prior Publication Data
US 2021/0046105 A1 Feb. 18, 2021

Related U.S. Application Data

(63) Continuation of application No. PCT/US2019/024944, filed on Mar. 29, 2019.

(60) Provisional application No. 62/650,207, filed on Mar. 29, 2018.

(51) Int. Cl.
| | |
|---|---|
| *A61K 9/14* | (2006.01) |
| *A61K 31/655* | (2006.01) |
| *A61K 31/662* | (2006.01) |
| *A61K 31/785* | (2006.01) |
| *A61K 47/54* | (2017.01) |
| *A61K 47/58* | (2017.01) |
| *A61K 47/69* | (2017.01) |
| *A61K 49/08* | (2006.01) |
| *A61K 49/12* | (2006.01) |
| *A61K 49/18* | (2006.01) |
| *A61K 51/06* | (2006.01) |
| *A61K 51/12* | (2006.01) |
| *C08F 290/06* | (2006.01) |

(52) U.S. Cl.
CPC ............ *A61K 31/785* (2013.01); *A61K 9/145* (2013.01); *A61K 31/655* (2013.01); *A61K 31/662* (2013.01); *A61K 47/545* (2017.08); *A61K 47/58* (2017.08); *A61K 47/6933* (2017.08); *A61K 47/6935* (2017.08); *A61K 49/085* (2013.01); *A61K 49/128* (2013.01); *A61K 49/1824* (2013.01); *A61K 49/1854* (2013.01); *A61K 51/065* (2013.01); *A61K 51/1244* (2013.01); *C08F 290/061* (2013.01)

(58) Field of Classification Search
CPC .... A61K 31/785; A61K 9/145; A61K 31/655; A61K 31/662; A61K 47/545; A61K 47/58; A61K 47/6933; A61K 47/6935; A61K 49/085; A61K 49/128; A61K 49/1824; A61K 49/1854; A61K 51/065; A61K 51/1244; C08F 290/061
See application file for complete search history.

(56) References Cited

U.S. PATENT DOCUMENTS

| | | | |
|---|---|---|---|
| 8,207,353 B2 * | 6/2012 | Sill | ........................ C07F 9/4006 549/359 |
| 8,323,621 B2 | 12/2012 | Bornhop et al. | |
| 8,822,670 B2 | 9/2014 | Kinoshita et al. | |
| 2011/0059907 A1 | 3/2011 | Gupta et al. | |
| 2016/0184344 A1 | 6/2016 | Xiong et al. | |

OTHER PUBLICATIONS

Ishihara K, Chen W, Liu Y, Tsukamoto Y, Inoue Y. Cytocompatible and multifunctional polymeric nanoparticles for transportation of bioactive molecules into and within cells. Sci Technol Adv Mater. Jul. 6, 2016;17(1):300-312 (Year: 2016).*
Bhuchar, Neha, et al. "Detailed study of the reversible addition-fragmentation chain transfer polymerization and co-polymerization of 2-methacryloyloxyethyl phosphorylcholine." Polymer Chemistry 2.3 (2011): 632-639. (Year: 2011).*
Samuelson, Lynn E., et al. "TSPO targeted dendrimer imaging agent: synthesis, characterization, and cellular internalization." Bioconjugate chemistry 20.11 (2009): 2082-2089. (Year: 2009).*
Li et al., mprovement of recognition specificity of surface protein-imprinted magnetic microspheres by reducing nonspecific adsorption of competitors using 2-methacryloyloxyethyl phosphorylcholine, Sensors and Actuators B: Chemical, vol. 208, pp. 559-568. (Year: 2015).*
Wang et al., Accelerated blood clearance phenomenon upon cross-administration of PEGylated nanocarriers in beagle dogs, International Journal of Nanomedicine, 10:, 3533-3545 (Year: 2015).*
Fliervoet et al., "Heterofunctional Poly(ethylene glycol) (PEG) Macroinitiator Enabling Controlled Synthesis of ABC Triblock Copolymers," Macromolecules, Oct. 30, 2017, vol. 50, pp. 8390-8397.

(Continued)

*Primary Examiner* — Abigail Vanhorn
(74) *Attorney, Agent, or Firm* — Greenberg Traurig LLP; Melissa Hunter-Ensor; Scott Goncher

(57) ABSTRACT

The present invention provides compositions and methods for targeting cells for therapeutic and/or diagnostic purposes, e.g., delivery of therapeutic and/or diagnostic agents to a cell. Nanoparticles and polymers functionalized with capture molecules, reporter molecules, and/or therapeutic agents are provided for the treatment or prevention of disease, including neurological diseases associated with neuroinflammation, and cancer.

18 Claims, 58 Drawing Sheets

Specification includes a Sequence Listing.

(56) References Cited

OTHER PUBLICATIONS

Kaminskas et al., "Dendrimer pharmacokinetics: the effect of size, structure and surface characteristics on ADME properties," Nanomedicine, 2011, vol. 6, No. 6, pp. 1063-1084.

Liu et al., "Combinational peptide library methods for immunobiology research," Experimental Hematology, 2003, vol. 31, pp. 11-30.

Mastorakos et al., "Highly compacted biodegradable DNA nanoparticles capable of overcoming the mucus barrier for Inhaled lung gene therapy," Proceedings of the National Academy of Sciences of the United States of America, Jul. 14, 2015, vol. 112, No. 28, pp. 8720-8725.

Nicolas, Julien, "Drug-Initiated Synthesis of Polymer Prodrugs: Combining Simplicity and Efficacy in Drug Delivery," Chemistry of Materials, Feb. 21, 2016, vol. 28, pp. 1591-1606.

Zielonka et al., "Mitochondria-Targeted Triphenylphosphonium-Based Compounds: Syntheses, Mechanisms of Action, and Therapeutic and Diagnostic Applications," Chemical Reviews, Aug. 9, 2017, vol. 117, No. 15, pp. 10043-10120.

International Search Report and Written Opinion in corresponding International Patent Application No. PCT/US19/24944, mailed Jun. 12, 2019 (17 pages).

\* cited by examiner

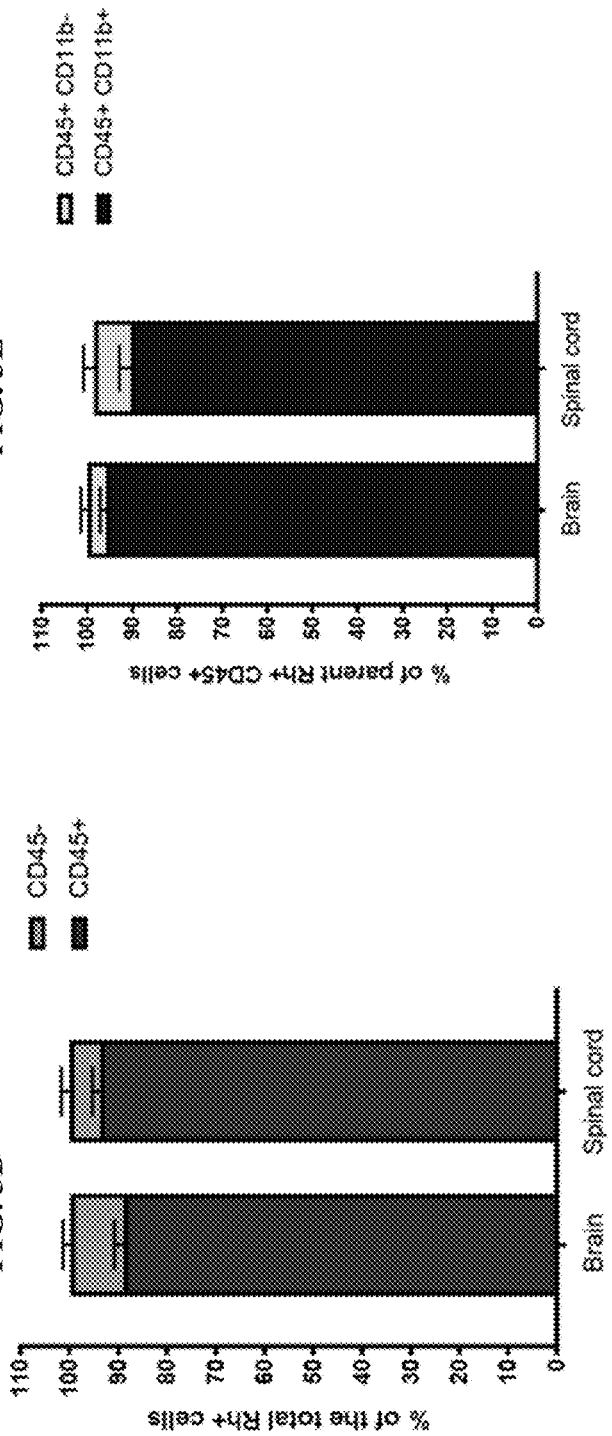
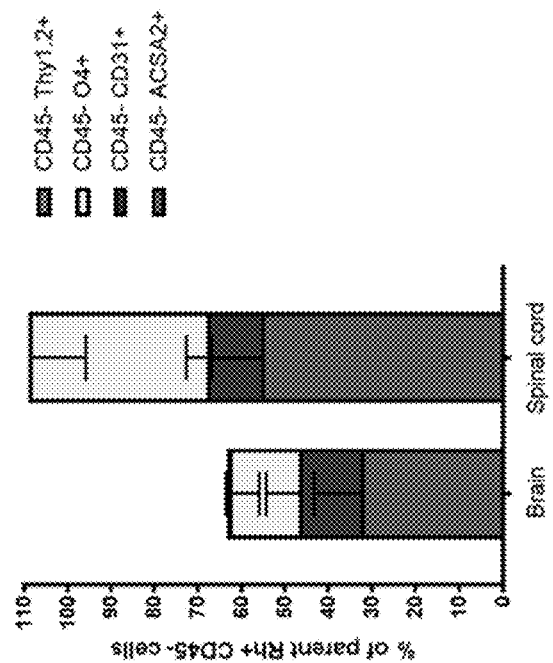
FIG. 3E
FIG. 3D
FIG. 3F

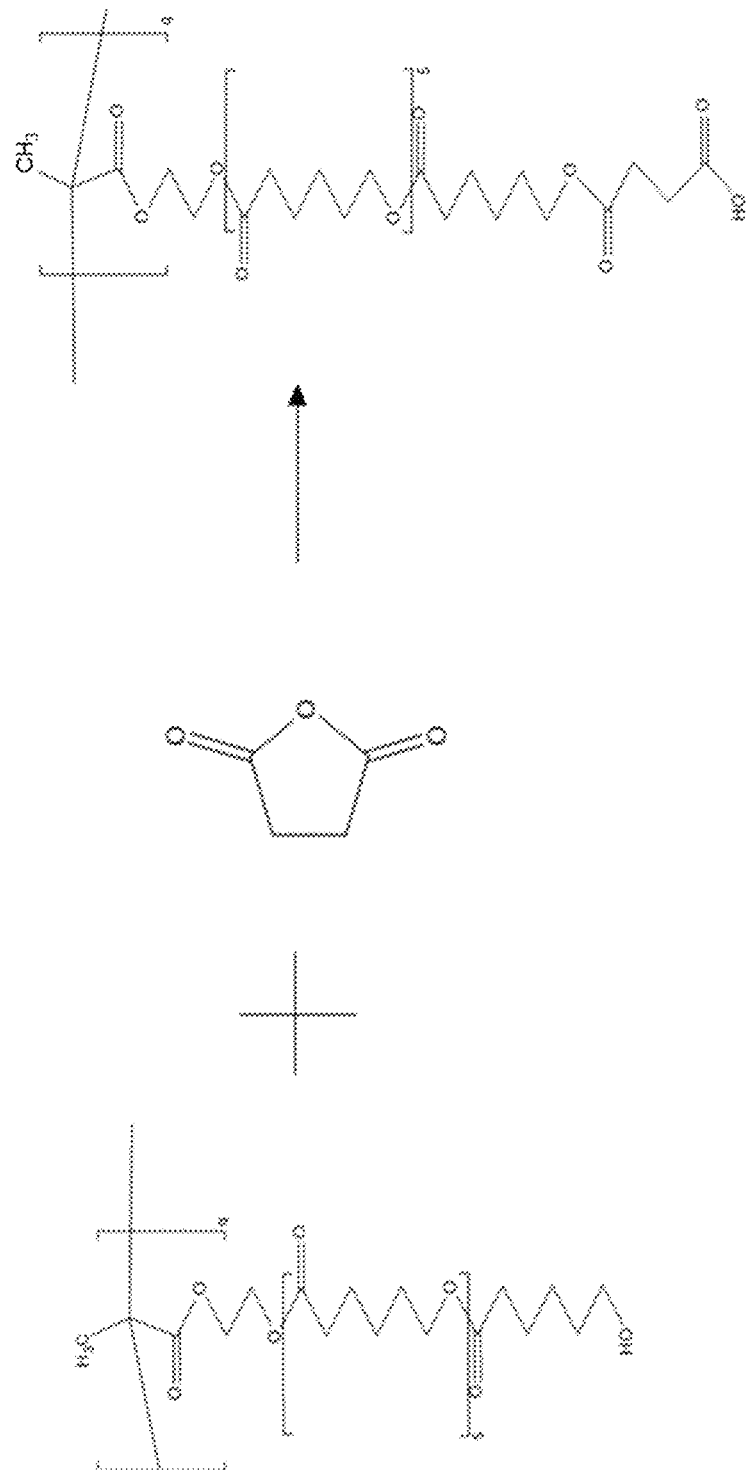
FIG. 4A Functionalization of HemaC15 with a COOH ending group

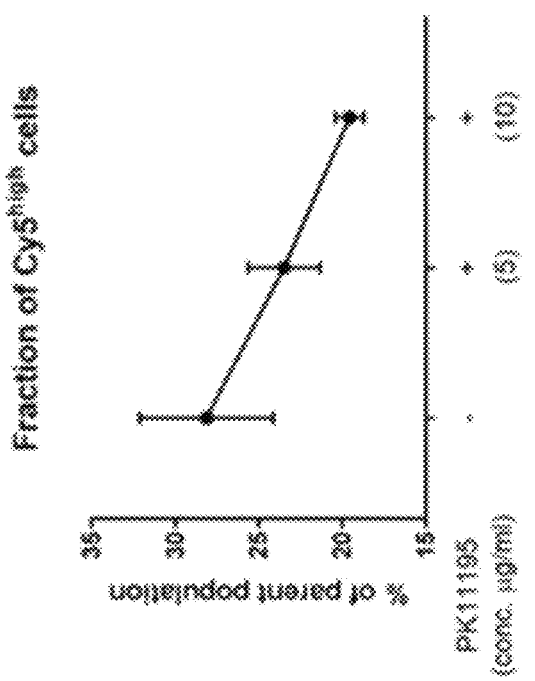
FIG. 12C
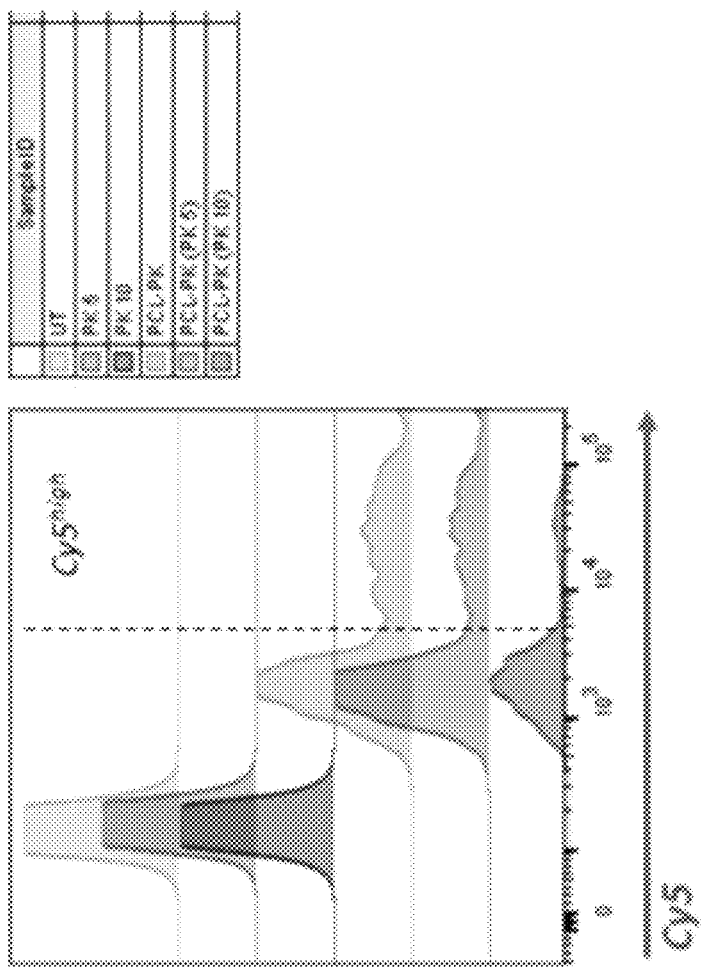

11

15

12

16

13

17

14

SEQUENCE LISTING

```
<160> NUMBER OF SEQ ID NOS: 6

<210> SEQ ID NO 1
<211> LENGTH: 169
<212> TYPE: PRT
<213> ORGANISM: Homo sapiens

<400> SEQUENCE: 1

Met Ala Pro Pro Trp Val Pro Ala Met Gly Phe Thr Leu Ala Pro Ser
1               5                   10                  15

Leu Gly Cys Phe Val Gly Ser Arg Phe Val His Gly Glu Gly Leu Arg
            20                  25                  30

Trp Tyr Ala Gly Leu Gln Lys Pro Ser Trp His Pro Pro His Trp Val
        35                  40                  45

Leu Gly Pro Val Trp Gly Thr Leu Tyr Ser Ala Met Gly Tyr Gly Ser
    50                  55                  60

Tyr Leu Val Trp Lys Glu Leu Gly Gly Phe Thr Glu Lys Ala Val Val
65                  70                  75                  80

Pro Leu Gly Leu Tyr Thr Gly Gln Leu Ala Leu Asn Trp Ala Trp Pro
                85                  90                  95

Pro Ile Phe Phe Gly Ala Arg Gln Met Gly Trp Ala Leu Val Asp Leu
            100                 105                 110

Leu Leu Val Ser Gly Ala Ala Ala Thr Thr Val Ala Trp Tyr Gln
            115                 120                 125

Val Ser Pro Leu Ala Ala Arg Leu Leu Tyr Pro Tyr Leu Ala Trp Leu
    130                 135                 140

Ala Phe Thr Thr Thr Leu Asn Tyr Cys Val Trp Arg Asp Asn His Gly
145                 150                 155                 160

Trp Arg Gly Gly Arg Arg Leu Pro Glu
                165

<210> SEQ ID NO 2
<211> LENGTH: 921
<212> TYPE: DNA
<213> ORGANISM: Homo sapiens

<400> SEQUENCE: 2
ggcggctggg aggggcgggg cggatgcggg gacagcggcc tggctaactc ctgccaggca     60
gtgcccttcc cggagcgtgc cctcgccgct gagctcccct gaacagcagc tgcagcagcc    120
```

```
atggccccgc cctgggtgcc cgccatgggc ttcacgctgg cgcccagcct ggggtgcttc      180
gtgggctccc gctttgtcca cggcgagggt ctccgctggt acgccggcct gcagaagccc      240
tcgtggcacc cgccccactg ggtgctgggc cctgtctggg gcacgctcta ctcagccatg      300
gggtacggct cctacctggt ctggaaagag ctgggaggct tcacagagaa ggctgtggtt      360
cccctgggcc tctacactgg gcagctggcc ctgaactggg catggccccc catcttcttt      420
ggtgcccgac aaatgggctg gccttggtg atctcctgc tggtcagtgg ggcggcggca        480
gccactaccg tggcctggta ccaggtgagc ccgctggccg cccgcctgct ctaccccctac     540
ctggcctggc tggccttcac gaccacactc aactactgcg tatggcggga caaccatggc      600
tggcgtgggg gacggcggct gccagagtga gtgcccggcc caccagggac tgcagctgca      660
ccagcaggtg ccatcacgct tgtgatgtgg tggccgtcac gctttcatga ccactgggcc      720
tgctagtctg tcagggcctt ggcccagggg tcagcagagc ttcagaggtg cccccacctg      780
agccccacc cggagcagt gtcctgtgct tctgcatgc ttagagcatg ttcttggaac          840
atggaatttt ataagctgaa taaagttttt gacttccttt aaaaaaaaaa aaaaaaaaa       900
aaaaaaaaa aaaaaaaaaa a                                                 921

<210> SEQ ID NO 3
<211> LENGTH: 595
<212> TYPE: PRT
<213> ORGANISM: Homo sapiens

<400> SEQUENCE: 3

Met Pro Ala Cys Cys Ser Cys Ser Asp Val Phe Gln Tyr Glu Thr Asn
1               5                   10                  15

Lys Val Thr Arg Ile Gln Ser Met Asn Tyr Gly Thr Ile Lys Trp Phe
            20                  25                  30

Phe His Val Ile Ile Phe Ser Tyr Val Cys Phe Ala Leu Val Ser Asp
        35                  40                  45

Lys Leu Tyr Gln Arg Lys Glu Pro Val Ile Ser Ser Val His Thr Lys
    50                  55                  60

Val Lys Gly Ile Ala Glu Val Lys Glu Glu Ile Val Glu Asn Gly Val
65                  70                  75                  80

Lys Lys Leu Val His Ser Val Phe Asp Thr Ala Asp Tyr Thr Phe Pro
                85                  90                  95

Leu Gln Gly Asn Ser Phe Phe Val Met Thr Asn Phe Leu Lys Thr Glu
            100                 105                 110

Gly Gln Glu Gln Arg Leu Cys Pro Glu Tyr Pro Thr Arg Arg Thr Leu
        115                 120                 125

Cys Ser Ser Asp Arg Gly Cys Lys Lys Gly Trp Met Asp Pro Gln Ser
    130                 135                 140

Lys Gly Ile Gln Thr Gly Arg Cys Val Val Tyr Glu Gly Asn Gln Lys
145                 150                 155                 160

Thr Cys Glu Val Ser Ala Trp Cys Pro Ile Glu Ala Val Glu Glu Ala
                165                 170                 175

Pro Arg Pro Ala Leu Leu Asn Ser Ala Glu Asn Phe Thr Val Leu Ile
            180                 185                 190

Lys Asn Asn Ile Asp Phe Pro Gly His Asn Tyr Thr Thr Arg Asn Ile
        195                 200                 205

Leu Pro Gly Leu Asn Ile Thr Cys Thr Phe His Lys Thr Gln Asn Pro
    210                 215                 220
```

Gln Cys Pro Ile Phe Arg Leu Gly Asp Ile Phe Arg Glu Thr Gly Asp
225                 230                 235                 240

Asn Phe Ser Asp Val Ala Ile Gln Gly Gly Ile Met Gly Ile Glu Ile
            245                 250                 255

Tyr Trp Asp Cys Asn Leu Asp Arg Trp Phe His His Cys Arg Pro Lys
        260                 265                 270

Tyr Ser Phe Arg Arg Leu Asp Asp Lys Thr Thr Asn Val Ser Leu Tyr
    275                 280                 285

Pro Gly Tyr Asn Phe Arg Tyr Ala Lys Tyr Lys Glu Asn Asn Val
290                 295                 300

Glu Lys Arg Thr Leu Ile Lys Val Phe Gly Ile Arg Phe Asp Ile Leu
305                 310                 315                 320

Val Phe Gly Thr Gly Lys Phe Asp Ile Ile Gln Leu Val Val Tyr
            325                 330                 335

Ile Gly Ser Thr Leu Ser Tyr Phe Gly Leu Ala Ala Val Phe Ile Asp
            340                 345                 350

Phe Leu Ile Asp Thr Tyr Ser Ser Asn Cys Cys Arg Ser His Ile Tyr
            355                 360                 365

Pro Trp Cys Lys Cys Cys Gln Pro Cys Val Val Asn Glu Tyr Tyr Tyr
370                 375                 380

Arg Lys Lys Cys Glu Ser Ile Val Glu Pro Lys Pro Thr Leu Lys Tyr
385                 390                 395                 400

Val Ser Phe Val Asp Glu Ser His Ile Arg Met Val Asn Gln Gln Leu
            405                 410                 415

Leu Gly Arg Ser Leu Gln Asp Val Lys Gly Gln Glu Val Pro Arg Pro
            420                 425                 430

Ala Met Asp Phe Thr Asp Leu Ser Arg Leu Pro Leu Ala Leu His Asp
            435                 440                 445

Thr Pro Pro Ile Pro Gly Gln Pro Glu Glu Ile Gln Leu Leu Arg Lys
            450                 455                 460

Glu Ala Thr Pro Arg Ser Arg Asp Ser Pro Val Trp Cys Gln Cys Gly
465                 470                 475                 480

Ser Cys Leu Pro Ser Gln Leu Pro Glu Ser His Arg Cys Leu Glu Glu
            485                 490                 495

Leu Cys Cys Arg Lys Lys Pro Gly Ala Cys Ile Thr Thr Ser Glu Leu
            500                 505                 510

Phe Arg Lys Leu Val Leu Ser Arg His Val Leu Gln Phe Leu Leu Leu
            515                 520                 525

Tyr Gln Glu Pro Leu Leu Ala Leu Asp Val Asp Ser Thr Asn Ser Arg
            530                 535                 540

Leu Arg His Cys Ala Tyr Arg Cys Tyr Ala Thr Trp Arg Phe Gly Ser
545                 550                 555                 560

Gln Asp Met Ala Asp Phe Ala Ile Leu Pro Ser Cys Cys Arg Trp Arg
            565                 570                 575

Ile Arg Lys Glu Phe Pro Lys Ser Glu Gly Gln Tyr Ser Gly Phe Lys
            580                 585                 590

Ser Pro Tyr
        595

<210> SEQ ID NO 4
<211> LENGTH: 3680
<212> TYPE: DNA
<213> ORGANISM: Homo sapiens

<400> SEQUENCE: 4

```
gtcattggag gagcttgaag ttaaagactc ctgctaaaaa ccagtacgtt tcattttgca      60
gttactggga gggggcttgc tgtggccctg tcaggaagag tagagctctg gtccagctcc     120
gcgcagggag ggaggctgtc accatgccgg cctgctgcag ctgcagtgat gttttccagt     180
atgagacgaa caaagtcact cggatccaga gcatgaatta tggcaccatt aagtggttct     240
tccacgtgat catcttttcc tacgtttgct ttgctctggt gagtgacaag ctgtaccagc     300
ggaaagagcc tgtcatcagt tctgtgcaca ccaaggtgaa ggggatagca gaggtgaaag     360
aggagatcgt ggagaatgga gtgaagaagt tggtgcacag tgtctttgac accgcagact     420
acaccttccc tttgcagggg aactctttct tcgtgatgac aaactttctc aaaacagaag     480
gccaagagca gcggttgtgt cccgagtatc ccacccgcag gacgctctgt tcctctgacc     540
gaggttgtaa aaagggatgg atggacccgc agagcaaagg aattcagacc ggaaggtgtg     600
tagtgtatga agggaaccag aagacctgtg aagtctctgc ctggtgcccc atcgaggcag     660
tggaagaggc cccccggcct gctctcttga acagtgccga aaacttcact gtgctcatca     720
agaacaatat cgacttcccc ggccacaact acaccacgag aaacatcctg ccaggtttaa     780
acatcacttg taccttccac aagactcaga atccacagtg tcccattttc cgactaggag     840
acatcttccg agaaacaggc gataattttt cagatgtggc aattcagggc ggaataatgg     900
gcattgagat ctactgggac tgcaacctag accgttggtt ccatcactgc cgtcccaaat     960
acagtttccg tcgccttgac gacaagacca ccaacgtgtc cttgtaccct ggctacaact    1020
tcagatacgc caagtactac aaggaaaaca atgttgagaa acggactctg ataaaagtct    1080
tcgggatccg ttttgacatc ctggtttttg gcaccggagg aaaatttgac attatccagc    1140
tggttgtgta catcggctca accctctcct acttcggtct ggccgctgtg ttcatcgact    1200
tcctcatcga cacttactcc agtaactgct gtcgctccca tatttatccc tggtgcaagt    1260
gctgtcagcc ctgtgtggtc aacgaatact actacaggaa gaagtgcgag tccattgtgg    1320
agccaaagcc gacattaaag tatgtgtcct ttgtggatga atcccacatt aggatggtga    1380
accagcagct actagggaga agtctgcaag atgtcaaggg ccaagaagtc ccaagacctg    1440
cgatggactt cacagatttg tccaggctgc ccctggccct ccatgacaca cccccgattc    1500
ctggacaacc agaggagata cagctgctta gaaaggaggc gactcctaga tccagggata    1560
gccccgtctg gtgccagtgt ggaagctgcc tcccatctca actccctgag agccacaggt    1620
gcctggagga gctgtgctgc cggaaaaagc cgggggcctg catcaccacc tcagagctgt    1680
tcaggaagct ggtcctgtcc agacacgtcc tgcagttcct cctgctctac caggagcccc    1740
tgctggcgct ggatgtggat tccaccaaca gccggctgcg gcactgtgcc tacaggtgct    1800
acgccacctg gcgcttcggc tcccaggaca tggctgactt tgccatcctg cccagctgct    1860
gccgctggag gatccggaaa gagttccgaa gagtgaagg gcagtacagt ggcttcaaga    1920
gtccttactg aagccaggca ccgtggctca cgtctgtaat cccagcgctt gggaggccg     1980 aggcaggcag atcacctgag gtcgggagtt ggagacccgc ctggctaaca aggcgaaatc    2040
ctgtctgtac taaaaataca aaaatcagcc agacatggtg gcatgcacct gcaatcccag    2100
ctactcggga ggctgaggca caagaatcac ttgaacccgg gaggcagagg ttgtagtgag    2160
cccagattgt gccactgctc tccagcctgg gaggcacagc aaactgtccc ccaaaaaaaa    2220
aaaagagtcc ttaccaatag caggggctgc agtagccatg ttaacatgac atttaccagc    2280
aacttgaact tcacctgcaa agctctgtgg ccacattttc agccaaaggg aaatatgctt    2340
```

```
tcatcttctg ttgctctctg tgtctgagag caaagtgacc tggttaaaca aaccagaatc    2400
cctctacatg gactcagaga aaagagattg agatgtaagt ctcaactctg tccccaggaa    2460
gttgtgtgac cctaggcctc tcacctctgt gcctctgtct ccttgttgcc caactactat    2520
ctcagagata ttgtgaggac aaattgagac agtgcacatg aactgtcttt taatgtgtaa    2580
agatctacat gaatgcaaaa catttcatta tgaggtcaga ctaggataat gtccaactaa    2640
aaacaaaccc ttttcatcct ggctggagaa tgtggagaac taaaggtggc cacaaattct    2700
ttgacactca agtcccccaa gacctaaggg ttttatctcc tccccttgaa tatgggtggc    2760
tctgattgct ttatccaaaa gtggaagtga cattgtgtca gtttcagatc ctgatcttaa    2820
gaggctgaca gcttctactt gctgtccctt ggaactcttg ctatcgggga agccagacgc    2880
catttaaaag tctgcctatc ctggccaggt gtggtggctc acacctgtaa tcccagcact    2940
ttgggagacc aaggcgggcg gatcacttaa agtcaggagt ccaagaccag actcgccaac    3000
atggtgaaac cgtatctcta ataaaaatac aaaaattagc tgggcatggt gcgggcacct    3060
gtagtcctag ctatcaagag gctgagacag gagaaacact tgaacctggg aggtggaggt    3120
tgcattgagc tgagatcgtg ccactgcact ccaggctggg tgacagagcg agactccatc    3180
tcaaaaaaaa aaaaagaaa aaaaaaatgt ctgcctatcc tgagactgcc ctgctgtgag    3240
gaagcccaag cagtcacgtg gacagtgcct gaccagcccc agctttcaag ccatccaagc    3300
ccagtcacca aacatgagag agaagaagcc ttcaggtgat tctggactcc actaacatat    3360
gactgatacc gcatgataca tcccaagtga gaactgcccc ataaatccag aaaaccacat    3420
tgctatctta agtccctaag tttggggctt atttgttcca cagcaacagg taactggaac    3480
agagggcaag cctgatgaat gggcacacag actcagccca taccttccct ggttctaatg    3540
ttctcaggga gccggacca acctggag cctcaggaac ttaggtttcc actggacagt    3600
tctagaaggg ctatagacca aatcaggtaa ctcaccagac cagccttgga atctatcaaa    3660
tctaactgct gagctaccca                                                 3680
```

<210> SEQ ID NO 5
<211> LENGTH: 360
<212> TYPE: PRT
<213> ORGANISM: Homo sapiens

<400> SEQUENCE: 5

Met Glu Glu Cys Trp Val Thr Glu Ile Ala Asn Gly Ser Lys Asp Gly
 1               5                  10                  15

Leu Asp Ser Asn Pro Met Lys Asp Tyr Met Ile Leu Ser Gly Pro Gln
            20                  25                  30

Lys Thr Ala Val Ala Val Leu Cys Thr Leu Leu Gly Leu Leu Ser Ala
        35                  40                  45

Leu Glu Asn Val Ala Val Leu Tyr Leu Ile Leu Ser Ser His Gln Leu
    50                  55                  60

Arg Arg Lys Pro Ser Tyr Leu Phe Ile Gly Ser Leu Ala Gly Ala Asp
65                  70                  75                  80

Phe Leu Ala Ser Val Val Phe Ala Cys Ser Phe Val Asn Phe His Val
                85                  90                  95

Phe His Gly Val Asp Ser Lys Ala Val Phe Leu Leu Lys Ile Gly Ser
            100                 105                 110

Val Thr Met Thr Phe Thr Ala Ser Val Gly Ser Leu Leu Leu Thr Ala
        115                 120                 125

Ile Asp Arg Tyr Leu Cys Leu Arg Tyr Pro Pro Ser Tyr Lys Ala Leu

|  | 130 |  | 135 |  |  | 140 |  |

Leu Thr Arg Gly Arg Ala Leu Val Thr Leu Gly Ile Met Trp Val Leu
145                 150                 155                 160

Ser Ala Leu Val Ser Tyr Leu Pro Leu Met Gly Trp Thr Cys Cys Pro
                165                 170                 175

Arg Pro Cys Ser Glu Leu Phe Pro Leu Ile Pro Asn Asp Tyr Leu Leu
            180                 185                 190

Ser Trp Leu Leu Phe Ile Ala Phe Leu Phe Ser Gly Ile Ile Tyr Thr
        195                 200                 205

Tyr Gly His Val Leu Trp Lys Ala His Gln His Val Ala Ser Leu Ser
    210                 215                 220

Gly His Gln Asp Arg Gln Val Pro Gly Met Ala Arg Met Arg Leu Asp
225                 230                 235                 240

Val Arg Leu Ala Lys Thr Leu Gly Leu Val Leu Ala Val Leu Leu Ile
                245                 250                 255

Cys Trp Phe Pro Val Leu Ala Leu Met Ala His Ser Leu Ala Thr Thr
            260                 265                 270

Leu Ser Asp Gln Val Lys Lys Ala Phe Ala Phe Cys Ser Met Leu Cys
        275                 280                 285

Leu Ile Asn Ser Met Val Asn Pro Val Ile Tyr Ala Leu Arg Ser Gly
    290                 295                 300

Glu Ile Arg Ser Ser Ala His His Cys Leu Ala His Trp Lys Lys Cys
305                 310                 315                 320

Val Arg Gly Leu Gly Ser Glu Ala Lys Glu Glu Ala Pro Arg Ser Ser
                325                 330                 335

Val Thr Glu Thr Glu Ala Asp Gly Lys Ile Thr Pro Trp Pro Asp Ser
            340                 345                 350

Arg Asp Leu Asp Leu Ser Asp Cys
        355                 360

<210> SEQ ID NO 6
<211> LENGTH: 1789
<212> TYPE: DNA
<213> ORGANISM: Homo sapiens

<400> SEQUENCE: 6
caggtcctgg gagaggacag aaaacaactg ggactcctca gccccggca gctcccagtg      60
cccagccacc cacaacacaa cccaaagcct tctagacaag ctcagtggaa tctgaagggc    120
ccaccccatg gaggaatgct gggtgacaga atagccaat ggctccaagg atggcttgga    180
ttccaaccct atgaaggatt acatgatcct gagtggtccc cagaagacag ctgttgctgt    240
gttgtgcact cttctgggcc tgctaagtgc cctggagaac gtggctgtgc tctatctgat    300
cctgtcctcc caccaactcc gccggaagcc ctcatacctg ttcattggca gcttggctgg    360
ggctgacttc ctggccagtg tggtctttgc atgcagcttt gtgaatttcc atgttttcca    420
tggtgtggat tccaaggctg tcttcctgct gaagattggc agcgtgacta tgaccttcac    480
agcctctgtg ggtagcctcc tgctgaccgc cattgaccga tacctctgcc tgcgctatcc    540
accttcctac aaagtctctg ctcacccgtg aagggcactg gtgaccctgg gcatcatgtg    600
ggtcctctca gcactagtct cctacctgcc cctcatggga tggacttgct gtcccaggcc    660
ctgctctgag cttttcccac tgatccccaa tgactacctg ctgagctggc tcctgttcat    720
cgccttcctc ttttccggaa tcatctacac ctatgggcat gttctctgga aggcccatca    780
gcatgtggcc agcttgtctg gccaccagga caggcaggtg ccaggaatgg cccgaatgag    840

-continued

```
gctggatgtg aggttggcca agaccctagg gctagtgttg gctgtgctcc tcatctgttg    900
gttcccagtg ctggccctca tgcccacag cctggccact acgctcagtg accaggtcaa    960
gaaggccttt gctttctgct ccatgctgtg cctcatcaac tccatggtca accctgtcat   1020
ctatgctcta cggagtggag agatccgctc tctgcccat cactgcctgg ctcactggaa   1080
gaagtgtgtg aggggccttg ggtcagaggc aaaagaagaa gccccgagat cctcagtcac   1140
cgagacagag gctgatggga aaatcactcc gtggccagat tccagagatc tagacctctc   1200
tgattgctga tgaggcctct tcccaattta acaactcaa gtcagaaatc agttcactcc   1260
ctggaagaga gagaggggtc ttggcactct cttcttactt aaaccagtcc cagacaccta   1320
gacacggacc ccttttgct gatgagtgtt gggactgact cctggaagac agcctggcct   1380
tgcccacctg cacacagtct gttggatagg tagggccacg aggagtagcc aggtaggcga   1440
gacacaaaag gcctgggaca gggtcagtac aagtcaggtc aggcttcatg cctgcatcct   1500
ccagagacca caggagccaa agcgagcctc caggcccagc aatgagggac ttgggagaaa   1560
tctgagaaga atgggttgtt ctcttgggaa gtcagggtat cagatgggat ggacatccag   1620
gtcttctctc tgcctaattg tcaaggcctc cttggctctg gagctatgaa aggcccact    1680
ttcaagtcac ccttgccact gaggaccgag gactatgcta tgatgaggat taaggtgttg   1740
acttgcctct ttcagagata aatgacaagc cttcaaaaaa aaaaaaaa              1789
```

COMPOSITIONS AND METHODS FOR TARGETING CELLS

CROSS-REFERENCE TO RELATED APPLICATION

This application is a U.S. National Stage filed under 35 U.S.C. § 111(a), which is a continuation of and claims priority to PCT/US2019/024944, filed Mar. 29, 2019, which claims the benefit of and priority to U.S. Provisional Application No. 62/650,207, filed Mar. 29, 2018, the entire contents of each of which are incorporated herein by reference.

STATEMENT OF RIGHTS TO INVENTIONS MADE UNDER FEDERALLY SPONSORED RESEARCH

This invention was made with government support under Grant No. W81XWH-17-1-0036 awarded by the Department of Defense. The government has certain rights in the invention.

BACKGROUND OF THE INVENTION

Accumulating lines of evidence suggest that neuroinflammation, i.e., the activation of glial cells in the central nervous system (CNS), is not just the result of reaction to neuronal death or damage, but is a key pathological process that actively contributes to the worsening and progression of symptoms in several neurodegenerative diseases, such as acute brain or spinal cord injury, and Amyotrophic Lateral Sclerosis (ALS).

The current therapeutic approaches for ALS are based on chronic administration of neuroprotective factors (e.g., trophic or anti-apoptotic factors, treatment with anti-glutamatergic drugs, or compounds enhancing proteasome or mitochondrial metabolic activity) or anti-inflammatory molecules (e.g., cyclooxygenase inhibitors or minocycline) among others. These strategies suffer from limited efficacy, possibly due to induction of pharmacological tolerance or to the lack of specificity for particular cell types (e.g., glia versus neurons or neurotoxic versus neuro-supportive microglia). Moreover, these strategies do not take into account the complexity of ALS pathology, such as compensatory neuro-supportive responses that co-exist with, or eventually evolve to, pro-degenerative cellular and molecular responses in different CNS districts. In fact, the most common initial presentation of ALS is focal asymmetric distal weakness accompanied by muscular atrophy, which reflects the presence of specific foci of neuronal dysfunction in restricted CNS areas. The organism senses this damage and initially tries to compensate for the neuronal loss, for example, by compensatory reinnervation from nearby motor neurons, which permits maintenance of motor function until more than 50% of motor units have been lost. However, over time this scenario eventually worsens. Damage spreading to other neuronal districts causes progressive deterioration of motor function, which eventually leads to a fatal outcome.

Microglia cells, the innate immune cells in the CNS, have recently gained great interest as a potential target for several therapeutic approaches to neurodegenerative disease. For example, fine tuning microglia/macrophage reactivity may play a key role in modulating neuroinflammatory processes, thereby producing potential significant therapeutic benefits. The major challenge for developing such therapeutic approaches is to achieve selective targeting of reactive microglia/macrophages in the CNS. Accordingly, new compositions and methods of treatment for neurodegenerative disease are urgently required.

SUMMARY OF THE INVENTION

As described below, the present invention features compositions and methods for targeting and delivery of therapeutic and/or diagnostic agents to a cell (e.g., microglia, tumor cell). The invention generally provides the use of nanoparticles and polymers functionalized with capture molecules, reporter molecules, and/or therapeutic agents for the treatment or prevention of disease (e.g., cancer, neurological diseases associated with neuroinflammation).

In one aspect, the invention provides a polymer or functionalized polymer having a first monomer: 2-Methacryloyloxyethyl phosphorylcholine (MPC), and a second monomer: methacrylate/amide PEG including a functionalized amine or azide, where one or more of a capture reagent and detectable is covalently linked via the functionalized amine or azide.

In another aspect the invention provides a method of making a polymer or functionalized polymer involving contacting a first monomer: 2-Methacryloyloxyethyl phosphorylcholine (MPC), and a second monomer: methacrylate/amide PEG having a functionalized amine or azide, in the presence of a radical and a thiocarbonylthio compound.

In another aspect, the invention provides a polymer or functionalized polymer made according to the method of any aspect of the invention.

In various embodiments of any aspect delineated herein, the polymer comprises Formula I

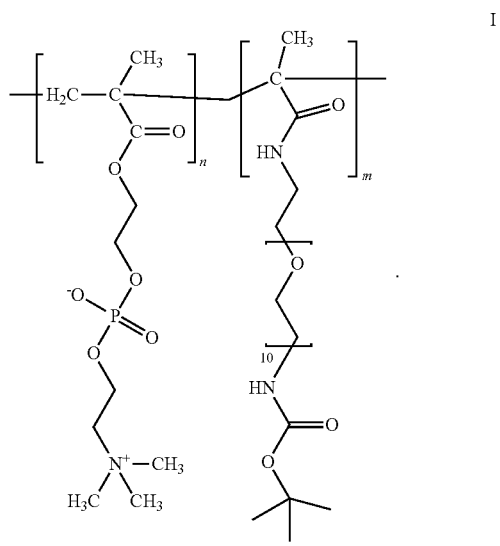

In various embodiments of any aspect delineated herein, the ratio of the first monomer to the second monomer is about 25:3 to about 25:6. In various embodiments of any aspect delineated herein, the functionalized amine is protected by a tert-Butyloxycarbonyl group.

In various embodiments of any aspect delineated herein, the polymer includes a third monomer: hydroxyethyl methacrylate polycaprolactone (HEMA-PCL) having a functionalized carboxyl group. In various embodiments, the polymer comprises Formula II:

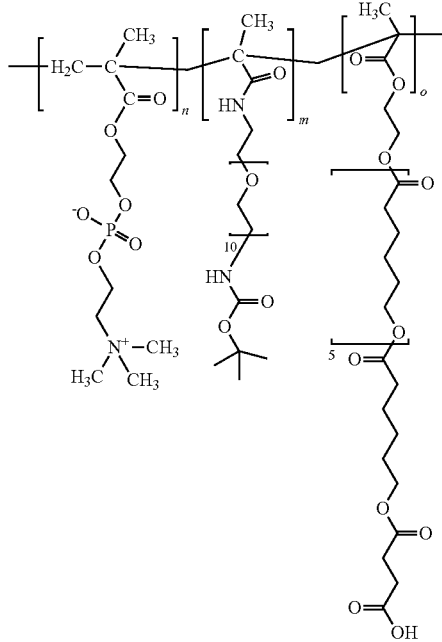

In various embodiments, the polymer contains a hydroxyethyl methacrylate-rhodamine (HEMA-Rhodamine) monomer. In various embodiments, the polymer contains a hydroxyethyl methacrylate-succinate (HEMA-succinate) monomer.

In another aspect, the invention provides a nanoparticle containing a polymer according to any aspect of the invention.

In another aspect, the invention provides a method of targeting a cell involving contacting the cell with a nanoparticle according to any aspect of the invention.

In another aspect, the invention provides a polymer or functionalized polymer containing a TSPO ligand or precursor or analog thereof covalently linked to a branched PEG polymer. In various embodiments, the TSPO ligand is one or more of PK11195, PBR28, Ro5-4864, GE180, FGIN-1-27, Alpidem, DPA-714, or precursor or analog thereof. In various embodiments, polymer or functionalized polymer includes a detectable moiety covalently linked to the branched PEG polymer. In various embodiments, the detectable moiety is a fluorescent dye, rhodamine, Fluorescein isothiocyanate (FITC), Cy5, or aminomethylcoumarin acetate (AMCA).

In another aspect, the invention provides a nanoparticle containing a polymer and iron, where the polymer contains a first monomer: 2-Methacryloyloxyethyl phosphorylcholine (MPC), and a second monomer: methacrylate PEG having a covalently linked diapocynin.

In another aspect, the invention provides a nanoparticle containing a polymer, where the polymer contains a first monomer: 2-Methacryloyloxyethyl phosphorylcholine (MPC), a second monomer: methacrylate PEG having a covalently linked diapocynin, and a third monomer: hydroxyethyl methacrylate-deferoxamine (HEMA-deferoxamine), where the deferoxamine is bound to Zirconium[89].

In another aspect, the invention provides a nanoparticle containing a biodegradable polycation or ionizable polymer containing a poly(β-amino ester) (PBAE), and a nucleic acid molecule, wherein the polymer comprises a first monomer: 2-Methacryloyloxyethyl phosphorylcholine (MPC), and a second monomer: methacrylate PEG.

In another aspect, the invention provides a method of detecting a cell involving contacting the cell with a nanoparticle containing a polymer, where the polymer contains a first monomer: 2-Methacryloyloxyethyl phosphorylcholine (MPC); a second monomer: methacrylate PEG comprising a covalently linked TSPO ligand, PK11195, PBR28, or a precursor or analog thereof; and a third monomer: hydroxyethyl methacrylate-deferoxamine (HEMA-deferoxamine), wherein the deferoxamine is bound to Zirconium[89].

In another aspect, the invention provides a method of detecting a cell involving contacting the cell with a nanoparticle containing a polymer and iron, where the polymer contains a first monomer: 2-Methacryloyloxyethyl phosphorylcholine (MPC), and a second monomer: methacrylate PEG comprising a covalently linked TSPO ligand, PK11195, PBR28, or a precursor or analog thereof.

In another aspect, the invention provides a method of detecting a cell involving contacting the cell with a nanoparticle containing a polymer, Poly(β-amino ester), and a nucleic acid molecule, where the polymer contains a first monomer: 2-Methacryloyloxyethyl phosphorylcholine (MPC), and a second monomer: methacrylate PEG; where the nucleic acid molecule expresses a fluorescent protein or green fluorescent protein (GFP).

In another aspect, the invention provides a method of delivering an agent to a cell involving contacting the cell with nanoparticle containing a polymer and the agent, where the polymer contains a first monomer: 2-Methacryloyloxyethyl phosphorylcholine (MPC), and a second monomer: methacrylate PEG covalently linked to one or more of a capture reagent, detectable moiety, or combination thereof.

In another aspect, the invention provides a method of delivering a nucleic acid molecule to a cell involving contacting the cell with a nanoparticle containing a polymer, Poly(β-amino ester), and a nucleic acid molecule, where the polymer contains a first monomer: 2-Methacryloyloxyethyl phosphorylcholine (MPC), and a second monomer: methacrylate PEG covalently linked to one or more of a capture reagent, detectable moiety, or combination thereof.

In another aspect, the invention provides a method of treating neuroinflammation in a subject involving administering to the subject a nanoparticle containing a polymer, where the polymer contains a first monomer: 2-Methacryloyloxyethyl phosphorylcholine (MPC), and a second monomer: methacrylate PEG having a covalently linked TSPO ligand, PK11195, PBR28, or a precursor or analog thereof; and a third monomer: hydroxyethyl methacrylate-deferoxamine (HEMA-deferoxamine), where the deferoxamine is bound to Zirconium[89].

In another aspect, the invention provides a method of treating neuroinflammation in a subject involving administering to the subject a nanoparticle containing a polymer and iron, where the polymer contains a first monomer: 2-Methacryloyloxyethyl phosphorylcholine (MPC), and a second monomer: methacrylate PEG having a covalently linked TSPO ligand, PK11195, PBR28, or a precursor or analog thereof.

In another aspect, the invention provides a method of treating cancer in a subject involving administering to the subject a nanoparticle containing a polymer and a chemotherapeutic agent, where the polymer contains a first monomer: 2-Methacryloyloxyethyl phosphorylcholine (MPC), and a second monomer: methacrylate PEG having a covalently linked TSPO ligand, PK11195, PBR28, or a precursor or analog thereof; and wherein the chemotherapeutic agent is selected from etoposide, busulfan, and lomustine.

In various embodiments of any aspect delineated herein, the nanoparticle contains iron (e.g., an Fe ion). In various embodiments of any aspect delineated herein, the nanoparticle contains hydroxyethyl methacrylate covalently linked to a chelator; deferoxamine (DFO); 1,4,7,10-Tetraazacyclododecane-1,4,7,10-tetraacetic acid; Tetraxetan; or EDTA. In various embodiments, the deferoxamine (DFO) is bound to a radioisotope, including e.g., Zirconium$^{89}$, Fluoride$^{18}$, or Carbonium$^{11}$. In various embodiments of any aspect delineated herein, the nanoparticle contains biodegradable polycation or ionizable polymer, comprising a poly(β-amino ester) (PBAE) polymer, wherein the PBAE polymer comprises polycaprolactone (PCL).

In various embodiments of any aspect delineated herein, the nanoparticle contains a nucleic acid molecule, polypeptide, or small molecule. In various embodiments, the nucleic acid molecule is a plasmid, vector, inhibitory nucleic acid, antisense oligonucleotide, or small interfering RNA (siRNA). In various embodiments, the nucleic acid molecule expresses a polypeptide or polynucleotide, including a therapeutic or reporter polypeptide, e.g., a fluorescent protein, green fluorescent protein (GFP), metallothionein, or Insulin growth factor (IGF1). In various embodiments of any aspect delineated herein, the nucleic acid molecule, polypeptide, or small molecule is directly conjugated to the nanoparticle. In various embodiments of any aspect delineated herein, the nucleic acid molecule, polypeptide, or small molecule is loaded in the nanoparticle.

In various embodiments of any aspect delineated herein, the nanoparticle contains a capture molecule or binding agent. In various embodiments, a cell (e.g., microglia, cancer cell, etc.) is targeted. In various embodiments, the targeting occurs in vitro or in vivo. In particular embodiments, the nanoparticle is administered to a subject (e.g., by Intra-cerebral Ventricular Injection (ICV) or intrathecal administration (ITL). In certain embodiments, the nanoparticle contains a Translocator protein (TSPO) ligand or capture molecule, including but not limited to, PK11195, PBR28, Ro5-4864, GE180, FGIN-1-27, Alpidem, DPA-714, or a precursor or analog thereof. In various embodiments of any aspect delineated herein, the nanoparticle targets a cell.

In certain embodiments, a cell surface protein or moiety is contacted with a capture molecule or ligand on the nanoparticle. In various embodiments, the cell surface protein or moiety is Translocator protein (TSPO), P2X purinoceptor 7 (P2X7r), Cannabinoid receptor type 2 (CB2r), CD68, fractalkine receptor CX3CR1, Glutamate aspartate transporter, proteoglycan NG2, oligodendrocyte antigen O4, CD31, CD90, or Acetylcholine receptor, or fragment thereof.

In various embodiments of any aspect delineated herein, a therapeutic agent or reporter is delivered (e.g., to a cell) using the nanoparticle. In various embodiments, the delivering occurs in vitro or in vivo. In certain embodiments, cell uptake of a therapeutic agent or reporter is provided using the nanoparticle. In certain embodiments, the therapeutic agent is an anti-inflammatory agent, e.g., diapocynin, or chemotherapeutic agent, e.g., etoposide, busulfan, or lomustine. In particular embodiments, the nanoparticle or component thereof is detectable by Positron Emission Tomography (PET) or Magnetic Resonance Imaging (Mill) (FIG. 1). In various embodiments, the detecting occurs in vitro or in vivo.

Other features and advantages of the invention will be apparent from the detailed description, and from the claims.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "Translocator protein (TSPO) polypeptide" is meant a polypeptide or fragment thereof having at least about 85%, or greater, amino acid identity to NCBI Accession No. NP_000705 (below) and having binding activity to benzodiazepine, and analogs thereof.

```
  1 mappwvpamg ftlapslgcf vgsrfvhgeg lrwyaglqkp swhpphwvlg pvwgtlysam
 61 gygsylvwke lggftekavv plglytggla lnwawppiff garqmgwalv dlllvsgaaa
121 attvawyqvs plaarllypy lawlaftttl nycvwrdnhg wrggrrlpe
                  50
```

By "TSPO nucleic acid molecule" is meant a polynucleotide encoding a TSPO polypeptide. An exemplary TSPO nucleic acid molecule sequence is provided at NCBI Accession No. NM_000714 (below):

```
  1 ggcggctggg aggggcgggg cggatgcggg gacagcggcc tggctaactc ctgccaggca
 61 gtgcccttcc cggagcgtgc cctcgccgct gagctcccct gaacagcagc tgcagcagcc
121 atggccccgc cctgggtgcc cgccatgggc ttcacgctgg cgcccagcct ggggtgcttc
181 gtgggctccc gctttgtcca cggcgagggt ctccgctggt acgccggcct gcagaagccc
241 tcgtggcacc cgccccactg ggtgctgggc cctgtctggg gcacgctcta ctcagccatg
301 gggtacggct cctacctggt ctggaaagag ctgggaggct tcacagagaa ggctgtggtt
```

```
361 ccccctgggcc tctacactgg gcagctggcc ctgaactggg catggccccc catcttcttt 421 ggtgcccgac aaatgggctg ggccttggtg gatctcctgc tggtcagtgg ggcggcggca 481 gccactaccg tggcctggta ccaggtgagc ccgctggccg cccgcctgct ctaccgctac 541 ctggcctggc tggccttcac gaccacactc aactactgcg tatggcggga caaccatggc 601 tggcgtgggg gacggcggct gccagagtga gtgcccggcc caccagggac tgcagctgca 661 ccagcaggtg ccatcacgct tgtgatgtgg tggccgtcac gctttcatga ccactgggcc 721 tgctagtctg tcagggcctt ggcccagggg tcagcagagc ttcagaggtg gccccacctg 781 agcccccacc cgggagcagt gtcctgtgct ttctgcatgc ttagagcatg ttcttggaac 841 atggaatttt ataagctgaa taaagttttt gacttccttt aaaaaaaaaa aaaaaaaaaa 901 aaaaaaaaaa aaaaaaaaa a
```

By "TSPO ligand" is meant an agent that specifically binds TSPO. Exemplary TSPO ligands are known in the art and include, but are not limited to, PK11195, PBR28, Ro5-4864, GE180, FGIN-1-27, Alpidem, DPA-714, and analogs thereof.

By "P2X purinoceptor 7 (P2X7r) polypeptide" is meant a polypeptide or fragment thereof having at least about 85%, or greater, amino acid identity to NCBI Accession No. NP_002553 (below) and having binding activity to ATP, and analogs thereof.

```
  1 mpaccscsdv fqyetnkvtr iqsmnygtik wffhviifsy vcfalvsdkl yqrkepviss 61 vhtkvkgiae vkeeivengv kklvhsvfdt adytfplqgn sffvmtnflk tegqeqrlcp 121 eyptrrtlcs sdrgckkgwm dpqskgiqtg rcvvyegnqk tcevsawcpi eaveeaprpa 181 llnsaenftv liknnidfpg hnyttrnilp glnitctfhk tqnpqcpifr lgdifretgd 241 nfsdvaiqgg imgieiywdc nldrwfhhcr pkysfrrldd kttnvslypg ynfryakyyk 301 ennvekrtli kvfgirfdil vfgtggkfdi iqlvvyigst lsyfglaavf idflidtyss 361 nccrshiypw ckccqpcvvn eyyyrkkces ivepkptlky vsfvdeshir mvnqqllgrs 421 lqdvkgqevp rpamdftdls rlplalhdtp pipgqpeeiq llrkeatprs rdspvwcqcg 481 sclpsqlpes hrcleelccr kkpgacitts elfrklvlsr hvlqflllyq epllaldvds 541 tnsrlrhcay rcyatwrfgs qdmadfailp sccrwrirke fpksegqysg fkspy
```

By "P2X7r nucleic acid molecule" is meant a polynucleotide encoding a P2X7r polypeptide. An exemplary P2X7r nucleic acid molecule sequence is provided at NCBI Accession No. NM_002562 (below):

```
  1 gtcattggag gagcttgaag ttaaagactc ctgctaaaaa ccagtacgtt tcattttgca 61 gttactggga gggggcttgc tgtggccctg tcaggaagag tagagctctg gtccagctcc 121 gcgcagggag ggaggctgtc accatgccgg cctgctgcag ctgcagtgat gttttccagt 181 atgagacgaa caaagtcact cggatccaga gcatgaatta tggcaccatt aagtggttct 241 tccacgtgat catctttttcc tacgtttgct ttgctctggt gagtgacaag ctgtaccagc 301 ggaaagagcc tgtcatcagt tctgtgcaca ccaaggtgaa ggggatagca gaggtgaaag 361 aggagatcgt ggagaatgga gtgaagaagt tggtgcacag tgtctttgac accgcagact 421 acaccttccc tttgcagggg aactcttttc tcgtgatgac aaactttctc aaaacagaag 481 gccaagagca gcggttgtgt ccgagtatc ccaccgcag gacgctctgt tcctctgacc 541 gaggttgtaa aaagggatgg atggacccgc agagcaaagg aattcagacc ggaaggtgtg 601 tagtgtatga agggaaccag aagacctgtg aagtctctgc ctggtgcccc atcgaggcag 661 tggaagaggc ccccggcct gctctcttga acagtgccga aaacttcact gtgctcatca
```

-continued

```
 721 agaacaatat cgacttcccc ggccacaact acaccacgag aaacatcctg ccaggtttaa
 781 acatcacttg taccttccac aagactcaga atccacagtg tcccattttc cgactaggag
 841 acatcttccg agaaacaggc gataattttt cagatgtggc aattcagggc ggaataatgg
 901 gcattgagat ctactgggac tgcaacctag accgttggtt ccatcactgc cgtcccaaat
 961 acagtttccg tcgccttgac gacaagacca ccaacgtgtc cttgtaccct ggctacaact
1021 tcagatacgc caagtactac aaggaaaaca atgttgagaa acggactctg ataaaagtct
1081 tcgggatccg ttttgacatc ctggttttg gcaccggagg aaaatttgac attatccagc
1141 tggttgtgta catcggctca accctctcct acttcggtct ggccgctgtg ttcatcgact
1201 tcctcatcga cacttactcc agtaactgct gtcgctccca tatttatccc tggtgcaagt
1261 gctgtcagcc ctgtgtggtc aacgaatact actacaggaa gaagtgcgag tccattgtgg
1321 agccaaagcc gacattaaag tatgtgtcct ttgtggatga atcccacatt aggatggtga
1381 accagcagct actagggaga agtctgcaag atgtcaaggg ccaagaagtc ccaagacctg
1441 cgatggactt cacagatttg tccaggctgc ccctggccct ccatgacaca ccccgattc
1501 ctggacaacc agaggagata cagctgctta gaaaggaggc gactcctaga tccagggata
1561 gccccgtctg gtgccagtgt ggaagctgcc tcccatctca actccctgag agccacaggt
1621 gcctggagga gctgtgctgc cggaaaaagc cgggggcctg catcaccacc tcagagctgt
1681 tcaggaagct ggtcctgtcc agacacgtcc tgcagttcct cctgctctac caggagccct
1741 tgctggcgct ggatgtggat tccaccaaca gccggctgcg gcactgtgcc tacaggtgct
1801 acgccacctg gcgcttcggc tcccaggaca tggctgactt tgccatcctg cccagctgct
1861 gccgctggag gatccggaaa gagtttccga agagtgaagg gcagtacagt ggcttcaaga
1921 gtccttactg aagccaggca ccgtggctca cgtctgtaat cccagcgctt gggaggccg
1981 aggcaggcag atcacctgag gtcgggagtt ggagacccgc ctggctaaca aggcgaaatc
2041 ctgtctgtac taaaaataca aaatcagcc agacatggtg gcatgcacct gcaatcccag
2101 ctactcggga ggctgaggca caagaatcac ttgaacccgg gaggcagagg ttgtagtgag
2161 cccagattgt gccactgctc tccagcctgg gaggcacagc aaactgtccc caaaaaaaa
2221 aaaagagtcc ttaccaatag caggggctgc agtagccatg ttaacatgac atttaccagc
2281 aacttgaact tcacctgcaa agctctgtgg ccacattttc agccaaaggg aaatatgctt
2341 tcatcttctg ttgctctctg tgtctgagag caaagtgacc tggttaaaca aaccagaatc
2401 cctctcacatg gactcagaga aaagagattg agatgtaagt ctcaactctg tccccaggaa
2461 gttgtgtgac cctaggcctc tcacctctgt gcctctgtct ccttgttgcc caactactat
2521 ctcagagata ttgtgaggac aaattgagac agtgcacatg aactgtcttt taatgtgtaa
2581 agatctacat gaatgcaaaa catttcatta tgaggtcaga ctaggataat gtccaactaa
2641 aaacaaaccc ttttcatcct ggctggagaa tgtggagaac taaaggtggc cacaaattct
2701 ttgacactca agtcccccaa gacctaaggg ttttatctcc tcccttgaa tatgggtggc
2761 tctgattgct ttatccaaaa gtggaagtga cattgtgtca gtttcagatc ctgatcttaa
2821 gaggctgaca gcttctactt gctgtccctt ggaactcttg ctatcgggga agccagacgc
2881 catttaaaag tctgcctatc ctggccaggt gtggtggctc acacctgtaa tcccagcact
2941 ttgggagacc aaggcgggcg gatcacttaa agtcaggagt ccaagaccag actcgccaac
3001 atggtgaaac cgtatctcta ataaaaatac aaaaattagc tgggcatggt gcgggcacct
3061 gtagtcctag ctatcaagag gctgagacag gagaaacact tgaacctggg aggtggaggt
3121 tgcattgagc tgagatcgtg ccactgcact ccaggctggg tgacagagcg agactccatc
```

```
3181 tcaaaaaaaa aaaaaagaaa aaaaaaatgt ctgcctatcc tgagactgcc ctgctgtgag 3241 gaagcccaag cagtcacgtg gacagtgcct gaccagcccc agctttcaag ccatccaagc 3301 ccagtcacca aacatgagag agaagaagcc ttcaggtgat tctggactcc actaacatat 3361 gactgatacc gcatgataca tcccaagtga aactgcccc ataaatccag aaaaccacat 3421 tgctatctta agtccctaag tttggggctt atttgttcca cagcaacagg taactggaac 3481 agagggcaag cctgatgaat gggcacacag actcagccca taccttccct ggttctaatg 3541 ttctcaggga gcccggacca accctgggag cctcaggaac ttaggtttcc actggacagt 3601 tctagaaggg ctatagacca aatcaggtaa ctcaccagac cagccttgga atctatcaaa 3661 tctaactgct gagctaccca
```

By "Cannabinoid receptor type 2 (CB2r) polypeptide" is meant a polypeptide or fragment thereof having at least about 85%, or greater, amino acid identity to NCBI Accession No. NP_001832 (below) and having binding activity to tetrahydrocannabinol (THC) 2-Arachidonoylglycerol (2-AG), N-arachidonylethanolamide, anandamide, SR145528, AM320, and analogs thereof.

```
  1 meecwvteia ngskdgldsn pmkdymilsg pqktavavlc tllgllsale nvavlylils 61 shqlrrkpsy lfigslagad flasvvfacs fvnfhvfhgv dskavfllki gsvtmtftas 121 vgsllltaid rylclrypps ykalltrgra lvtlgimwvl salvsylplm gwtccprpcs 181 elfplipndy llswllfiaf lfsgiiytyg hvlwkahqhv aslsghqdrq vpgmarmrld 241 vrlaktlglv lavllicwfp vlalmahsla ttlsdqvkka fafcsmlcli nsmvnpviya 301 lrsgeirssa hhclahwkkc vrglgseake eaprssvtet eadgkitpwp dsrdldlsdc
```

By "CNR2 nucleic acid molecule" is meant a polynucleotide encoding a CB2r polypeptide. An exemplary CB2r nucleic acid molecule sequence is provided at NCBI Accession No. NM_001841 (below):

```
   1 caggtcctgg gagaggacag aaaacaactg ggactcctca gcccccggca gctcccagtg 61 cccagccacc cacaacacaa cccaaagcct tctagacaag ctcagtggaa tctgaagggc 121 ccaccccatg gaggaatgct gggtgacaga gatagccaat ggctccaagg atggcttgga 181 ttccaaccct atgaaggatt acatgatcct gagtggtccc cagaagacag ctgttgctgt 241 gttgtgcact cttctgggcc tgctaagtgc cctggagaac gtggctgtgc tctatctgat 301 cctgtcctcc caccaactcc gccggaagcc ctcataccty ttcattggca gcttggctgg 361 ggctgacttc ctggccagtg tggtctttgc atgcagcttt gtgaatttcc atgttttcca 421 tggtgtggat tccaaggctg tcttcctgct gaagattggc agcgtgacta tgaccttcac 481 agcctctgtg ggtagcctcc tgctgaccgc cattgaccga tacctctgcc tgcgctatcc 541 accttcctac aaagctctgc tcacccgtgg aagggcactg gtgaccctgg gcatcatgtg 601 ggtcctctca gcactagtct cctacctgcc cctcatggga tggacttgct gtcccaggcc 661 ctgctctgag ctttttccac tgatccccaa tgactacctg ctgagctggc tcctgttcat 721 cgccttcctc ttttccggaa tcatctacac ctatgggcat gttctctgga aggcccatca 781 gcatgtggcc agcttgtctg gccaccagga caggcaggtg ccaggaatgg cccgaatgag 841 gctggatgtg aggttggcca agaccctagg ctagtgttg gctgtgctcc tcatctgttg 901 gttcccagtg ctggccctca tggcccacag cctggccact acgctcagtg accaggtcaa 961 gaaggccttt gctttctgct ccatgctgtg cctcatcaac tccatggtca accctgtcat
```

```
1021  ctatgctcta cggagtggag agatccgctc ctctgcccat cactgcctgg ctcactggaa 1081  gaagtgtgtg aggggccttg ggtcagaggc aaaagaagaa gccccgagat cctcagtcac 1141  cgagacagag gctgatggga aaatcactcc gtggccagat tccagagatc tagacctctc 1201  tgattgctga tgaggcctct tcccaattta aacaactcaa gtcagaaatc agttcactcc 1261  ctggaagaga gagagggtc  ttggcactct cttcttactt aaaccagtcc cagacaccta 1321  gacacggacc cctttttgct gatgagtgtt gggactgact cctggaagac agcctggcct 1381  tgcccacctg cacacagtct gttggatagg tagggccacg aggagtagcc aggtaggcga 1441  gacacaaaag gcctgggaca gggtcagtac aagtcaggtc aggcttcatg cctgcatcct 1501  ccagagacca caggagccaa agcgagcctc caggcccagc aatgagggac ttgggagaaa 1561  tctgagaaga atgggttgtt ctcttgggaa gtcagggtat cagatgggat ggacatccag 1621  gtcttctctc tgcctaattg tcaaggcctc cttggctctg gagctatgaa aggcccact 1681  ttcaagtcac ccttgccact gaggaccgag gactatgcta tgatgaggat taaggtgttg 1741  acttgcctct ttcagagata aatgacaagc cttcaaaaaa aaaaaaaaa
```

By "agent" is meant any small molecule chemical compound, antibody, nucleic acid molecule, or polypeptide, or fragments thereof.

By "ameliorate" is meant decrease, suppress, attenuate, diminish, arrest, or stabilize the development or progression of a disease.

The term "antibody," as used herein, refers to an immunoglobulin molecule which specifically binds with an antigen. The term "antibody fragment" refers to a portion of an intact antibody and refers to the antigenic determining variable regions of an intact antibody.

By "alteration" or "change" is meant an increase or decrease. An alteration may be by as little as 1%, 2%, 3%, 4%, 5%, 10%, 20%, 30%, or by 40%, 50%, 60%, or even by as much as 70%, 75%, 80%, 90%, or 100%.

By "biologic sample" is meant any tissue, cell, fluid, or other material derived from an organism.

By "capture reagent" or "binding agent" is meant a reagent that specifically binds a nucleic acid molecule or polypeptide to select or isolate the nucleic acid molecule or polypeptide. In various embodiments, the capture reagent is one or more of a small molecule, peptide, scFv, or aptamer that specifically binds a polypeptide marker of interest.

As used herein, the terms "determining", "assessing", "assaying", "measuring" and "detecting" refer to both quantitative and qualitative determinations, and as such, the term "determining" is used interchangeably herein with "assaying," "measuring," and the like. Where a quantitative determination is intended, the phrase "determining an amount" of an analyte and the like is used. Where a qualitative and/or quantitative determination is intended, the phrase "determining a level" of an analyte or "detecting" an analyte is used.

"Detect" refers to identifying the presence, absence or amount of the analyte to be detected.

By "detectable label" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "disease" is meant any condition or disorder that damages or interferes with the normal function of a cell, tissue, or organ.

By "effective amount" is meant the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "fragment" is meant a portion of a protein or nucleic acid that is substantially identical to a reference protein or nucleic acid. In some embodiments the portion retains at least 50%, 75%, or 80%, or more preferably 90%, 95%, or even 99% of the biological activity of the reference protein or nucleic acid described herein.

By "inhibitory nucleic acid" or "inhibitory polynucleotide" is meant a double-stranded RNA, siRNA, shRNA, or antisense RNA, or a portion thereof, or a mimetic thereof, that when administered to a mammalian cell results in a decrease (e.g., by 10%, 25%, 50%, 75%, or even 90-100%) in the expression of a target gene. Typically, a nucleic acid inhibitor comprises at least a portion of a target nucleic acid molecule, or an ortholog thereof, or comprises at least a portion of the complementary strand of a target nucleic acid molecule. For example, an inhibitory nucleic acid molecule comprises at least a portion of any or all of the nucleic acids delineated herein.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "detectable moiety" or "label" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes, biotin, digoxigenin, or haptens.

By "marker" is meant any clinical indicator, protein, metabolite, or polynucleotide having an alteration associated with a disease, disorder, or condition. In various embodiments, the marker is a protein present on the surface of a cell, e.g., a receptor.

The term "monomer" or "building block" refers to any discreet chemical compound of any molecular weight. A monomer or building block may comprise two or more smaller monomers connected through chemical bonds, for example.

By "microglia" is meant an immune cell of the central nervous system.

By "nanoparticle" is meant a composite structure of nanoscale dimensions. In particular, nanoparticles are typically particles of a size in the range of from about 1 to about 500 nm, and are usually spherical although different morphologies are possible depending on the nanoparticle composition. The portion of the nanoparticle contacting an environment external to the nanoparticle is generally identified as the surface of the nanoparticle. In nanoparticles herein described, the size limitation can be restricted to two dimensions and so that nanoparticles herein described include composite structure having a diameter from about 1 to about 500 nm, where the specific diameter depends on the nanoparticle composition and on the intended use of the nanoparticle according to the experimental design. For example, nanoparticles to be used in several therapeutic and/or diagnostic applications typically have a size of about 200 nm or below, and the ones used, in particular, for delivery associated with therapeutic agents typically have a diameter from about 1 to about 100 nm.

As used herein "neurodegenerative disease" refers to any of a group of diseases characterized by the progressive loss of structure and/or function of neurons, including death of neurons. Exemplary neurodegenerative diseases include, without limitation, amyotrophic lateral sclerosis.

As used herein, the term "polymer" refers to a molecule composed of repeating structural units (or monomers) typically connected by covalent chemical bonds. The term "polymer" is also meant to include the terms copolymer and oligomers. In one embodiment, a polymer comprises a backbone (i.e., the chemical connectivity that defines the central chain of the polymer, including chemical linkages among the various polymerized monomeric units) and a side chain (i.e., the chemical connectivity that extends away from the backbone).

As used herein, the term "polymerization" or "crosslinking" refers to at least one reaction that consumes at least one functional group in a monomeric molecule (or monomer), oligomeric molecule (or oligomer) or polymeric molecule (or polymer), to create at least one chemical linkage between at least two distinct molecules (e.g., intermolecular bond), at least one chemical linkage within the same molecule (e.g., intramolecular bond), or any combinations thereof. A polymerization or crosslinking reaction may consume between about 0% and about 100% of the at least one functional group available in the system. In one embodiment, polymerization or crosslinking of at least one functional group results in about 100% consumption of the at least one functional group. In another embodiment, polymerization or crosslinking of at least one functional group results in less than about 100% consumption of the at least one functional group. Polymerization reactions comprise, for example, ether formation, thioether formation, thioester formation, ester formation and amide formation.

A "copolymer" is a polymer derived from two or more monomeric species (or monomers or building blocks). Copolymerization refers to methods used to chemically synthesize a copolymer. Copolymers vary depending on the different types and arrangement of monomers. For example, in a copolymer consisting of two different types of monomers, the copolymers may be alternating (wherein the two different types of monomers alternate on the copolymer), block (wherein the copolymer comprises two or more homopolymers linked by covalent units), periodic (wherein a specific sequence of the two types of monomers repeats itself throughout the copolymer), or statistical (wherein the sequence of monomers follows a statistical rule).

By "increasing proliferation" is meant increasing cell division of a cell in vivo or in vitro.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

The term "subject" or "patient" refers to an animal which is the object of treatment, observation, or experiment. By way of example only, a subject includes, but is not limited to, a mammal, including, but not limited to, a human or a non-human mammal, such as a non-human primate, murine, bovine, equine, canine, ovine, or feline.

By "reduces" is meant a negative alteration of at least 10%, 25%, 50%, 75%, or 100%.

By "reference" is meant a standard of comparison or control condition.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95%, 96%, 97%, 98%, or even 99% or more identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "specifically binds" is meant a compound (e.g., peptide) that recognizes and binds a molecule (e.g., polypeptide), but which does not substantially recognize and bind other molecules in a sample, for example, a biological sample.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Any compounds, compositions, or methods provided herein can be combined with one or more of any of the other compositions and methods provided herein.

As used herein, the singular forms "a", "an", and "the" include plural forms unless the context clearly dictates otherwise. Thus, for example, reference to "a biomarker" includes reference to more than one biomarker.

Unless specifically stated or obvious from context, as used herein, the term "or" is understood to be inclusive.

The term "including" is used herein to mean, and is used interchangeably with, the phrase "including but not limited to."

As used herein, the terms "comprises," "comprising," "containing," "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

BRIEF DESCRIPTION OF THE DRAWINGS

FIG. 2A depicts the structure of methacryloyloxyethyl phosphorylcholine (MPC). FIG. 2B depicts the structures of $NH_2$-Peg-Boc and MePeg-BOC. FIG. 2C depicts the structure of nMPC-mMePegBoc. FIG. 2D depicts the structure of block copolymer of nMPC mMePegBoc qPCL5Q. FIG. 2E depicts Dynamic Light Scattering (DLS) analysis of methacryloyloxyethyl phosphorylcholine nanoparticles (NP-MPC). FIG. 2F depicts functional group (Peg-N3) can be used for ligand functionalization through click-chemistry in place of Peg-Boc in the structures depicted in FIGS. 2B-2D. In FIGS. 2B-2D and 2F, the box highlights the functional group utilized for ligand functionalization (Peg-Boc)

FIG. 3A depicts uptake of NP50 or NP-MPC in BV2 microglia cell lines, assessed by flow cytometry. FIG. 3B depicts flow cytometric evaluation of NP50 or NP-MPC biodistribution in the brain of mice, upon injection in the cerebral lateral ventricles (ICV) or intrathecally at lumbar level (ITL). FIG. 3C depicts flow cytometric evaluation of NP50 or NP-MPC biodistribution in the spinal cord of mice upon injection in the cerebral lateral ventricles (ICV) or intrathecally at lumbar level (ITL). FIG. 3D depicts cytofluorimetric quantification of the biodistribution of NP-MPC within different CNS cell types: $CD45^+$ versus $CD45^-$. FIG. 3E depicts cytofluorimetric quantification of the biodistribution of NP-MPC within different CNS cell types: $CD11b^+$ microglia versus $CD11b^-$ leukocytes within $CD45^+$ fraction. FIG. 3F depicts cytofluorimetric quantification of the biodistribution of NP-MPC within different CNS cell types: $O4^+$ oligodendrocytes versus $ACSA2^+$ astrocytes, $CD31^+$ vascular endothelial cells or Thy1.2 positive neurons, within $CD45^-$ fraction.

FIG. 4A depicts a schematic representation of the steps for production of a block copolymer capable of loading iron in NPs (top panel).

FIG. 5A depicts T2 (spin-spin) and SWI (susceptibility weighted imaging) Mill images of the brain of a wild type or a SOD1.G93A mouse. The latter was injected bilaterally ICV (SOD1.G93A, arrows in upper left panel) with NP-SPION. Hyper-intense signal was detected in the facial nucleus of SOD1.G93A mouse (SOD1.G93A, arrows in upper right panel), consistent with the neurodegeneration occurring at this disease stage. Prominent NPs+ signal (arrow) was detected by SWI at the site of injection and throughout the brain parenchyma (SOD1.G93A, arrows in bottom panels). FIG. 5B depicts cytofluorimetric analysis of rhodaminated NP-SPION biodistribution, confirming the uptake by CNS $CD45^+/CD11b^+$ microglia cells.

FIG. 12C are graphs illustrating the different fractions of Cy5$^{high}$ cells and the percentage of Cy5$^{high}$ cells in a population of cells after treatment with PK11195.

FIG. 13A depicts assessment performed after 4 hours of incubation of the polymers on cells. **=$p<0.001$; 2-way ANOVA followed by Tukey's post-hoc test (n≥3). FIG. 13B depicts assessment performed after 24 hours of incubation of the polymers on cells. **=$p<0.001$; 2-way ANOVA followed by Tukey's post-hoc test (n≥3).

FIG. 14A depicts normalized fluorescence intensity (Fnorm) evaluated for red fluorescent tagged hTSPO alone or in the presence of PK11195. FIG. 14B depicts normalized fluorescence intensity (Fnorm) evaluated for red fluorescent tagged hTSPO alone or in the presence of Ro5-4864. FIG. 14C depicts MST traces evaluated for non-functionalized polymers. FIG. 14D depicts MST traces evaluated for PK11195-functionalized polymer. FIG. 14E depicts quantification of baseline normalized fluorescence intensity for the traces shown in FIGS. 14C and 14D and highlights binding of P3F and P5F to hTSPO target. ****=$p<0.001$; 1-way ANOVA followed by Dunnet's post-hoc test vs No ligand (n≥3).

FIG. 16A is a graph illustrating the uptake of batch 2_1 NP-MPC functionalized with PBR-28 precursor (MPC-PBR) and non-functionalized (MPC-NF) after 4 hours or 24 hours of incubation in BV2 cells. FIG. 16B is a graph illustrating the uptake of batch 2_2 NP-MPC functionalized with PBR-28 precursor (MPC-PBR) and non-functionalized (MPC-NF) after 4 hours or 24 hours of incubation in BV2 cells. FIG. 16C is a graph illustrating the uptake of batch 1_1 NP-MPC functionalized with PBR-28 precursor (MPC-PBR) and non-functionalized (MPC-NF) after 4 hours or 24 hours of incubation in BV2 cells. FIG. 16D is a graph illustrating the uptake of batch 1_2 NP-MPC functionalized with PBR-28 precursor (MPC-PBR) and non-functionalized (MPC-NF) after 4 hours or 24 hours of incubation in BV2 cells. Table 4 provides a summary of MPC-PBR and MPC-NF batches. FIG. 16E is a graph illustrating the uptake of batch 2_1 MPC-PBR or MPC-NF in BV2 cells after incubation for 4 hours in the presence of increasing concentrations of the free ligand PBR-28. FIG. 16F is a graph illustrating the uptake of batch 2_2 MPC-PBR or MPC-NF in BV2 cells after incubation for 4 hours in the presence of increasing concentrations of the free ligand PBR-28. FIG. 16G is a graph illustrating the uptake of batch 1_1 MPC-PBR or MPC-NF in BV2 cells after incubation for 4 hours in the presence of increasing concentrations of the free ligand PBR-28. FIG. 16H is a graph illustrating the uptake of batch 1_2 MPC-PBR or MPC-NF in BV2 cells after incubation for 4 hours in the presence of increasing concentrations of the free ligand PBR-28. Values are shown as percentage to the uptake reported in the untreated controls (UT, i.e. no PBR-28 in the culture medium). *=$p<0.001$; =$p<0.01$; *=$p<0.05$; 2-way ANOVA followed by Dunnet's post-hoc test versus respective UT (n≥3).

FIG. 17A depicts assessment performed after 4 hours of incubation of the NPs on cells. 2-way ANOVA (n≥3). FIG. 17B depicts assessment performed after 24 hours of incubation of the NPs on cells. 2-way ANOVA (n≥3).

DETAILED DESCRIPTION OF THE INVENTION

Figure 1:
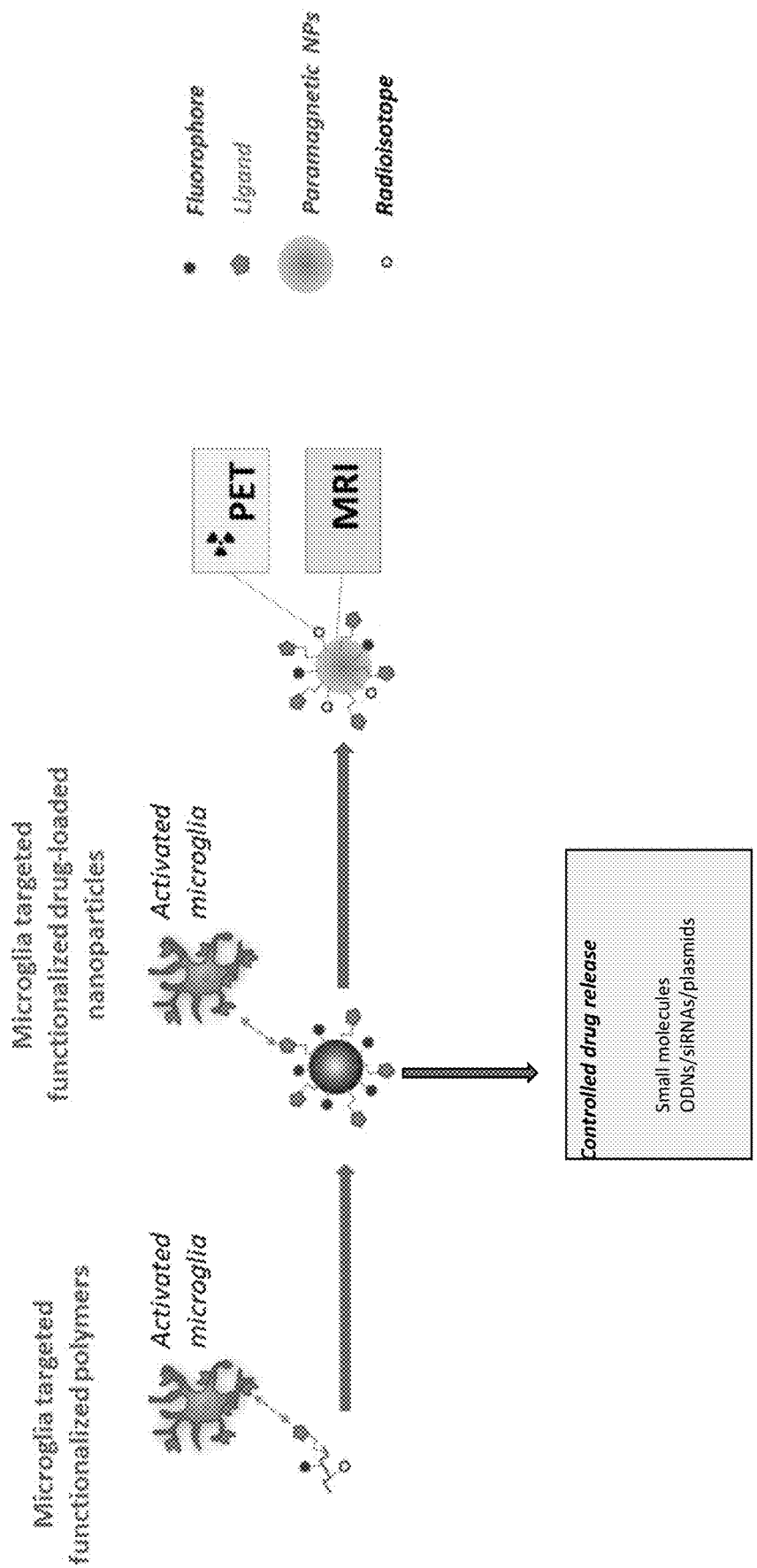
FIG. 1 depicts cell targeted functionalized polymers and cell targeted functionalized drug-loaded nanoparticles and their uses in therapeutic drug delivery and/or diagnostics.

As described herein, the present invention features compositions and methods for targeting and delivery of therapeutic and/or diagnostic agents to a cell. This invention is directed to an innovative pharmacological platform that can provide cell-target specificity and the possibility to monitor non-invasively the drug biodistribution and the therapeutic efficacy in vivo. The invention includes the use of nanoparticles and polymers functionalized with capture molecules, reporter molecules, and/or therapeutic agents for the treatment or prevention of disease, including neurological diseases associated with neuroinflammation and cancer.

The present invention is based at least in part on several discoveries described herein. Briefly, the innovation comprises the use of polymeric nanoparticles functionalized with cell-target selective ligands, combining, at the same time, the capability of: i) cell-specific delivery of therapeutic molecules, with potential improvement in drug efficacy and prevention of possible unwanted side effects; ii) controlled release of multiple drugs, thus widening the spectrum of key molecular pathways that can be targeted at the same time (an aspect of great value for multi-factorial diseases such as Amyotrophic Lateral Sclerosis (ALS) and other neurodegenerative diseases where neuroinflammation is involved); and/or iii) providing prognostic/diagnostic information (by identification of the CNS areas affected by neuroinflammation) and monitoring the sites of drug delivery.

This approach reflects principles of precision medicine, an advancing field of science that holds great promise for ALS and neurodegenerative diseases. In contrast to the therapeutic approaches tested up to now, that were mainly based on chronic administration of neuroprotective factors (e.g. trophic or anti-apoptotic factors, treatment with anti-glutamatergic drugs or compounds enhancing proteasome or mitochondrial metabolic activity) or anti-inflammatory molecules (such as cyclooxygenase inhibitors or minocycline) among others. These strategies suffered of limited efficacy, due to possible induction of pharmacological tolerance or to the lack of specificity for selective cell types (glia versus neurons or neurotoxic versus neuro-supportive microglia). Moreover, they do not take into account the complexity of the CNS pathology, where in different CNS districts we can observe compensatory neuro-supportive attempts that co-exist with, or eventually evolve to, pro-degenerative cellular and molecular responses. In fact, as an example, the most common initial presentation of ALS is focal asymmetric distal weakness accompanied by muscular atrophy, which reflects the presence of specific foci of neuronal dysfunction in restricted CNS areas. Like in any biological system, the organism senses these damages and initially tries to compensate the neuronal loss (e.g., compensatory reinnervation from nearby motor neurons permits a good maintenance of the motor function until more than 50% of motor units have been lost). However, over-time this scenario eventually worsens through spreading of the damage to the other neuronal districts, finally causing the progressive deterioration of motor function which eventually leads to a fatal outcome. The response of microglia cells in ALS fits perfectly in this picture: microglia activation initially exerts a neuro-supportive function but eventually this response results insufficient and is overwhelmed by a shift towards a more neuro-toxic phenotype.

Neurodegenerative Diseases

Neurodegenerative diseases are a class of neurological diseases that are characterized by the progressive loss of the structure and/or function of neurons and/or neuronal cell death. Inflammation has been implicated for a role in several neurodegenerative diseases. Progressive loss of motor and sensory neurons and the ability of the mind to refer sensory information to an external object is affected in different kinds of neurodegenerative diseases. Non-limiting examples of neurodegenerative diseases include ALS, e.g., familial ALS and sporadic ALS.

Relationships between microglia and neurodegeneration have been observed. Activation of glial cells in ALS plays an important role in disease progression and spreading of the pathology to other CNS districts. Aberrant activation of microglia cells in ALS orchestrates a neurotoxic environment.

A health care professional may diagnose a subject as having a neurodegenerative disease by the assessment of one or more symptoms of a neurodegenerative disease in the subject. Non-limiting symptoms of a neurodegenerative disease in a subject include difficulty lifting the front part of the foot and toes; weakness in arms, legs, feet, or ankles; hand weakness or clumsiness; slurring of speech; difficulty swallowing; muscle cramps; twitching in arms, shoulders, and tongue; difficulty chewing; difficulty breathing; muscle paralysis; partial or complete loss of vision; double vision; tingling or pain in parts of body; electric shock sensations that occur with head movements; tremor; unsteady gait; fatigue; dizziness; loss of memory; disorientation; misinterpretation of spatial relationships; difficulty reading or writing; difficulty concentrating and thinking; difficulty making judgments and decisions; difficulty planning and performing familiar tasks; depression; anxiety; social withdrawal; mood swings; irritability; aggressiveness; changes in sleeping habits; wandering; dementia; loss of automatic movements; impaired posture and balance; rigid muscles; bradykinesia; slow or abnormal eye movements; involuntary jerking or writhing movements (chorea); involuntary, sustained contracture of muscles (dystonia); lack of flexibility; lack of impulse control; and changes in appetite. A health care professional may also base a diagnosis, in part, on the subject's family history of a neurodegenerative disease. A health care professional may diagnose a subject as having a neurodegenerative disease upon presentation of a subject to a health care facility (e.g., a clinic or a hospital). In some instances, a health care professional may diagnose a subject as having a neurodegenerative disease while the subject is admitted in an assisted care facility. Typically, a physician diagnoses a neurodegenerative disease in a subject after the presentation of one or more symptoms.

Nanoparticles

The present invention provides methods of delivering nanoparticles comprising a capture reagent, a therapeutic agent, cytotoxic agent (e.g., cell ablation), and/or a detectable reporter comprising administering a nanoparticle comprising the one or more agents to a subject (e.g., a mammal such as a human).

In general, a "nanoparticle" refers to any particle having a diameter of less than 500 nm. In certain preferred embodiments, nanoparticles of the invention have a greatest dimension (e.g., diameter) of 200 nm or less. In other preferred embodiments, nanoparticles of the invention have a greatest dimension ranging between 25 nm and 100 nm. In other preferred embodiments, nanoparticles of the invention have a greatest dimension of 100 nm or less. In other preferred embodiments, nanoparticles of the invention have a greatest dimension ranging between about 45 nm and 50 nm. Nanoparticles encompassed in the present invention may be provided in different forms, e.g., as solid nanoparticles (e.g., non-metal, lipid-based solids, polymers), suspensions of nanoparticles, or combinations thereof. Metal, dielectric, and semiconductor nanoparticles may be prepared, as well as hybrid structures (e.g., core-shell nanoparticles). Such nanoscale particles are used in biomedical applications as drug carriers or imaging agents and may be adapted for similar purposes in the present invention. Semi-solid and soft nanoparticles have been manufactured, and are within the scope of the present invention. Nanoparticles with surfaces that are half hydrophilic and half hydrophobic are termed Janus particles and are particularly effective for stabilizing emulsions. They can self-assemble at water/oil interfaces and act as solid surfactants. In one embodiment, nanoparticles based on self assembling bioadhesive polymers are contemplated, which may be applied to oral delivery of agents, intravenous delivery of agents and nasal delivery of agents, all to the brain. Other embodiments, such as oral absorption of hydrophobic drugs, are also contemplated. The molecular envelope technology involves an engineered polymer envelope that is protected and delivered to the site of the disease (Mazza et al. ACS Nano 7, 1016-1026 (2013); Siew et al. Mol Pharm 9, 14-28 (2012); Lalatsa et al. J Control Release 161, 523-536 (2012); Lalatsa et al. Mol Pharm 9, 1665-1680 (2012); Garrett et al. J Biophotonics 5, 458-468 (2012); Uchegbu, Expert Opin Drug Deliv 3, 629-640 (2006); Uchegbu et al. Int J Pharm 224, 185-199 (2001); Qu et al. Biomacromolecules 7, 3452-3459 (2006)).

Several types of particle delivery systems and/or formulations are known to be useful in a diverse spectrum of biomedical applications. In general, a particle is defined as a small object that behaves as a whole unit with respect to its transport and properties. Particles are further classified according to diameter. Coarse particles cover a range between 2,500 and 10,000 nanometers. Fine particles are sized between 100 and 2,500 nanometers. Ultrafine particles, or nanoparticles, are generally between 1 and 100 nanometers in size. The basis of the 100-nm limit is the fact that novel properties that differentiate particles from the bulk material typically develop at a critical length scale of under 100 nm.

As used herein, a particle delivery system/formulation is defined as any biological delivery system/formulation, which includes a particle in accordance with the present invention. A particle in accordance with the present invention is any entity having a greatest dimension (e.g. diameter) of less than 500 nm. In some embodiments, inventive particles have a greatest dimension of less than 200 nm. In some embodiments, inventive particles have a greatest dimension of less than 100 nm. In some embodiments, inventive particles have a greatest dimension of less than 500 nm, 400 nm, 300 nm, 200 nm, or 100 nm. Typically, inventive particles have a greatest dimension (e.g., diameter) of 500 nm or less. In some embodiments, inventive particles have a greatest dimension (e.g., diameter) of 250 nm or less. In some embodiments, inventive particles have a greatest dimension (e.g., diameter) of 200 nm or less. In some embodiments, inventive particles have a greatest dimension (e.g., diameter) of 150 nm or less. In some embodiments, inventive particles have a greatest dimension (e.g., diameter) of 100 nm or less. Smaller particles, e.g., having a greatest dimension of 50 nm or less are used in some embodiments of the invention. In some embodiments, inventive particles have a greatest dimension ranging between 25 nm and 200 nm.

Particle characterization (including e.g., characterizing morphology, dimension, etc.) is done using a variety of different techniques. Common techniques are electron microscopy (TEM, SEM), atomic force microscopy (AFM), dynamic light scattering (DLS), X-ray photoelectron spectroscopy (XPS), powder X-ray diffraction (XRD), Fourier transform infrared spectroscopy (FTIR), matrix-assisted laser desorption/ionization time-of-flight mass spectrometry (MALDI-TOF), ultraviolet-visible spectroscopy, dual polarisation interferometry, microscale thermophoresis (MST), and nuclear magnetic resonance (NMR). Characterization (dimension measurements) may be made as to native particles (i.e., preloading) or after loading of the cargo (therapeutic agents, detectable reporters, or any combination thereof, and may include additional carriers and/or excipients) to provide particles of an optimal size for delivery for any in vitro, ex vivo, and/or in vivo application of the present invention. In certain preferred embodiments, particle dimension (e.g., diameter) characterization is based on measurements using dynamic laser scattering (DLS).

Particle delivery systems within the scope of the present invention may be provided in any form, including but not limited to solid, semi-solid, emulsion, or colloidal particles. As such any of the delivery systems described herein may be provided as particle delivery systems within the scope of the present invention.

Methods of Treatment

The present invention provides methods of treating disease and/or disorders or symptoms thereof which comprise administering a therapeutically effective amount of a pharmaceutical composition comprising a nanoparticle or polymer described herein to a subject (e.g., a mammal such as a human). In certain embodiments, the subject has a neurological disease, e.g., associated with neuroinflammation, and the nanoparticle or polymer is used to deliver a therapeutic agent, e.g., diapocynin, to a cell in the CNS, e.g., a microglia. In other embodiments, the subject has cancer or a neoplasia, and the nanoparticle or polymer is used to deliver a chemotherapeutic and/or cytotoxic agent, e.g., etoposide or lomustine, to a cancer cell. Thus, in various embodiments the invention is directed to methods of treating a subject suffering from or susceptible to a disease or disorder or symptom thereof. The method includes the step of administering to the mammal a therapeutic amount of a nanoparticle or polymer herein sufficient to treat the disease or disorder or symptom thereof, under conditions such that the disease or disorder is treated.

The methods herein include administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method). Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like). In some embodiments, the compounds herein are also used in the treatment of any other disorders in which myelination deficiency or loss is implicated, including multiple sclerosis.

Compounds and Synthesis

The compounds of the invention can be prepared from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures. Those skilled in the art of organic synthesis will recognize that the nature and order of the synthetic steps presented may be varied for the purpose of optimizing the formation of the compounds described herein.

Synthetic chemistry transformations (including protecting group methodologies) useful in synthesizing the compounds described herein are known in the art and include, for example, those such as described in R. C. Larock, *Comprehensive Organic Transformations*, 2d. ed., Wiley-VCH Publishers (1999); P. G. M. Wuts and T. W. Greene, *Protective Groups in Organic Synthesis*, 4th Ed., John Wiley and Sons (2007); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy (FT-IR), spectrophotometry (e.g., UV-visible), or mass spectrometry (MS), or by chromatography such as high performance liquid chromatography (HPLC) or thin layer chromatography (TLC).

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene, et al., *Protective Groups in Organic Synthesis*, 2d. Ed., Wiley & Sons, 1991, which is incorporated herein by reference in its entirety.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

Resolution of racemic mixtures of compounds can be carried out by any of numerous methods known in the art. An example method includes preparation of the Mosher's ester or amide derivative of the corresponding alcohol or amine, respectively. The absolute configuration of the ester or amide is then determined by proton and/or $^{19}$F NMR spectroscopy. An example method includes fractional recrystallization using a "chiral resolving acid," which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid, or the various optically active camphorsulfonic acids. Resolution of racemic mixtures can also be carried out by elution on a column packed with an optically active resolving agent (e.g., dinitrobenzoylphenylglycine). Suitable elution solvent compositions can be determined by one skilled in the art.

Antibodies

As reported herein, antibodies that specifically bind a marker (e.g., a cell surface moiety or receptor) are useful in the methods of the invention, including therapeutic and diagnostic methods. In particular embodiments, the invention provides a nanoparticle or polymer having an scFv or antibody fragment that specifically binds a cell surface marker of a microglia and contains a therapeutic and/or diagnostic agent.

Antibodies can be intact immunoglobulins derived from natural sources or from recombinant sources and can be immunoreactive portions of intact immunoglobulins. Antibodies are typically tetramers of immunoglobulin molecules. Tetramers may be naturally occurring or reconstructed from single chain antibodies or antibody fragments. As used herein, the term "antibody" means not only intact antibody molecules, but also fragments of antibody molecules that retain immunogen-binding ability. Such fragments are also well known in the art and are regularly employed both in vitro and in vivo. Examples of antibody fragments include, but are not limited to, Fab, Fab', F(ab') 2, and Fv fragments, linear antibodies, scFv antibodies, single-domain antibodies, such as camelid antibodies (Riechmann, 1999, Journal of Immunological Methods 231:25-38), composed of either a VL or a VH domain which exhibit sufficient affinity for the target, and multispecific antibodies formed from antibody fragments.

The antibodies in the present invention may exist in a variety of forms including, for example, polyclonal antibodies, monoclonal antibodies, Fv, Fab and F(ab') 2, as well as single chain antibodies (scFv), humanized antibodies, and human antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426). For example, F(ab')$_2$, and Fab fragments that lack the Fc fragment of an intact antibody, clear more rapidly from the circulation, and may have less non-specific tissue binding than an intact antibody (Wahl et al., *J. Nucl. Med.* 24:316-325 (1983). Thus, the antibodies of the invention comprise, without limitation, whole native antibodies, bispecific antibodies; chimeric antibodies; Fab, Fab', single chain V region fragments (scFv), fusion polypeptides, and unconventional antibodies.

Unconventional antibodies include, but are not limited to, nanobodies, linear antibodies (Zapata et al., Protein Eng. 8(10): 1057-1062, 1995), single domain antibodies, single chain antibodies, and antibodies having multiple valencies (e.g., diabodies, tribodies, tetrabodies, and pentabodies). Nanobodies are the smallest fragments of naturally occurring heavy-chain antibodies that have evolved to be fully functional in the absence of a light chain. Nanobodies have the affinity and specificity of conventional antibodies although they are only half of the size of a single chain Fv fragment. The consequence of this unique structure, combined with their extreme stability and a high degree of homology with human antibody frameworks, is that nanobodies can bind therapeutic targets not accessible to conventional antibodies. Recombinant antibody fragments with multiple valencies provide high binding avidity and unique targeting specificity to cancer cells. These multimeric scFvs (e.g., diabodies, tetrabodies) offer an improvement over the parent antibody since small molecules of ~60-100 kDa in size provide faster blood clearance and rapid tissue uptake. See Power et al., (Generation of recombinant multimeric antibody fragments for tumor diagnosis and therapy. Methods Mol Biol, 207, 335-50, 2003); and Wu et al. (Anticarcinoembryonic antigen (CEA) diabody for rapid tumor targeting and imaging. Tumor Targeting, 4, 47-58, 1999).

Various techniques for making and using unconventional antibodies have been described. Bispecific antibodies produced using leucine zippers are described by Kostelny et al. (J. Immunol. 148(5):1547-1553, 1992). Diabody technology is described by Hollinger et al. (Proc. Natl. Acad. Sci. USA 90:6444-6448, 1993). Another strategy for making bispecific antibody fragments using single-chain Fv (sFv) diners is described by Gruber et al. (J. Immunol. 152:5368, 1994). Trispecific antibodies are described by Tutt et al. (J. Immunol. 147:60, 1991). Single chain Fv polypeptide antibodies include a covalently linked VH:VL heterodimer which can be expressed from a nucleic acid including $V_H$- and $V_L$-encoding sequences either joined directly or joined by a peptide-encoding linker as described by Huston, et al. (Proc. Nat. Acad. Sci. USA, 85:5879-5883, 1988). See, also, U.S. Pat. Nos. 5,091,513, 5,132,405 and 4,956,778; and U.S. Patent Publication Nos. 20050196754 and 20050196754.

In various embodiments, an antibody is monoclonal. Alternatively, the antibody is a polyclonal antibody. The preparation and use of polyclonal antibodies are also known by the skilled artisan. The invention also encompasses hybrid antibodies, in which one pair of heavy and light chains is obtained from a first antibody, while the other pair of heavy and light chains is obtained from a different second antibody. Such hybrids may also be formed using humanized heavy and light chains. Such antibodies are often referred to as "chimeric" antibodies.

In general, intact antibodies are said to contain "Fc" and "Fab" regions. The Fc regions are involved in complement activation and are not involved in antigen binding. An antibody from which the Fc' region has been enzymatically cleaved, or which has been produced without the Fc' region, designated an "F(ab')$_2$" fragment, retains both of the antigen binding sites of the intact antibody. Similarly, an antibody from which the Fc region has been enzymatically cleaved, or which has been produced without the Fc region, designated an "Fab" fragment, retains one of the antigen binding sites of the intact antibody. Fab fragments consist of a covalently bound antibody light chain and a portion of the antibody heavy chain, denoted "Fd." The Fd fragments are the major determinants of antibody specificity (a single Fd fragment may be associated with up to ten different light chains without altering antibody specificity). Isolated Fd fragments retain the ability to specifically bind to immunogenic epitopes.

Methods of preparing antibodies are well known to those of ordinary skill in the science of immunology. Antibodies can be made by any of the methods known in the art utilizing a soluble polypeptide, or immunogenic fragment thereof, as an immunogen. One method of obtaining antibodies is to immunize suitable host animals with an immunogen and to follow standard procedures for polyclonal or monoclonal antibody production. The immunogen will facilitate presentation of the immunogen on the cell surface. Immunization of a suitable host can be carried out in a number of ways. Nucleic acid sequences encoding polypeptides or immunogenic fragments thereof, can be provided to the host in a delivery vehicle that is taken up by immune cells of the host. The cells will in turn express the polypeptide thereby generating an immunogenic response in the host. Alternatively, nucleic acid sequences encoding human polypeptides or immunogenic fragments thereof, can be expressed in cells in vitro, followed by isolation of the polypeptide and administration of the polypeptide to a suitable host in which antibodies are raised.

Alternatively, antibodies may, if desired, be derived from an antibody phage display library. A bacteriophage is capable of infecting and reproducing within bacteria, which can be engineered, when combined with human antibody genes, to display human antibody proteins. Phage display is the process by which the phage is made to 'display' the human antibody proteins on its surface. Genes from the human antibody gene libraries are inserted into a population of phage. Each phage carries the genes for a different antibody and thus displays a different antibody on its surface.

Antibodies made by any method known in the art can then be purified from the host. Antibody purification methods may include salt precipitation (for example, with ammonium sulfate), ion exchange chromatography (for example, on a cationic or anionic exchange column preferably run at neutral pH and eluted with step gradients of increasing ionic strength), gel filtration chromatography (including gel filtration HPLC), and chromatography on affinity resins such as protein A, protein G, hydroxyapatite, and anti-immunoglobulin.

Antibodies can be conveniently produced from hybridoma cells engineered to express the antibody. Methods of making hybridomas are well known in the art. The hybridoma cells can be cultured in a suitable medium, and spent medium can be used as an antibody source. Polynucleotides encoding the antibody of interest can in turn be obtained from the hybridoma that produces the antibody, and then the antibody may be produced synthetically or recombinantly from these DNA sequences. For the production of large amounts of antibody, it is generally more convenient to obtain an ascites fluid. The method of raising ascites generally comprises injecting hybridoma cells into an immunologically naive histocompatible or immunotolerant mammal, especially a mouse. The mammal may be primed for ascites production by prior administration of a suitable composition (e.g., Pristane).

Monoclonal antibodies (Mabs) produced by methods of the invention can be "humanized" by methods known in the art. "Humanized" antibodies are antibodies in which at least part of the sequence has been altered from its initial form to render it more like human immunoglobulins. Techniques to humanize antibodies are particularly useful when non-human animal (e.g., murine) antibodies are generated. Examples of methods for humanizing a murine antibody are provided in U.S. Pat. Nos. 4,816,567, 5,530,101, 5,225,539, 5,585,089, 5,693,762 and 5,859,205.

Aptamers

Aptamers are another class of binding agent or capture reagent that can be used to target the compositions of the invention to a cell. Aptamers are nucleic acid-based molecules that bind specific ligands. Aptamers that specifically bind a marker of the cell (e.g., a cell surface moiety or receptor) are useful in the methods of the invention. Methods for making aptamers with a particular binding specificity are known as detailed in U.S. Pat. Nos. 5,475,096; 5,670,637; 5,696,249; 5,270,163; 5,707,796; 5,595,877; 5,660,985; 5,567,588; 5,683,867; 5,637,459; and 6,011,020.

Recombinant Polypeptide Expression

The nanoparticle and polymer compositions of the invention can be functionalized with polypeptide capture molecules and detectable reporters. To express the polypeptides of the invention, DNA molecules obtained by any of the methods described herein or those that are known in the art, can be inserted into appropriate expression vectors by techniques well-known in the art. For example, a double stranded DNA can be cloned into a suitable vector by restriction enzyme linking involving the use of synthetic DNA linkers or by blunt-ended ligation. DNA ligases are usually used to ligate DNA molecules and undesirable joining can be avoided by treatment with alkaline phosphatase.

Therefore, the invention includes vectors (e.g., recombinant plasmids) that include nucleic acid molecules (e.g., genes or recombinant nucleic acid molecules encoding genes) as described herein. The term "recombinant vector" includes a vector (e.g., plasmid, phage, phasmid, virus, cosmid, fosmid, or other purified nucleic acid vector) that has been altered, modified or engineered such that it contains greater, fewer, or different nucleic acid sequences than those included in the native or natural nucleic acid molecule from which the recombinant vector was derived. For example, a recombinant vector may include a nucleotide sequence encoding a polypeptide, or fragment thereof, operatively linked to regulatory sequences, e.g., promoter sequences, terminator sequences, and the like, as defined herein. Recombinant vectors which allow for expression of the genes or nucleic acids included in them are referred to as "expression vectors."

In some of the molecules of the invention described herein, one or more DNA molecules having a nucleotide sequence encoding one or more polypeptides of the invention are operatively linked to one or more regulatory sequences, which are capable of integrating the desired DNA molecule into a prokaryotic host cell. Cells which have been stably transformed by the introduced DNA can be selected, for example, by introducing one or more markers which allow for selection of host cells which contain the expression vector. A selectable marker gene can either be linked directly to a nucleic acid sequence to be expressed, or be introduced into the same cell by co-transfection. Additional elements may also be needed for optimal synthesis of proteins described herein. It would be apparent to one of ordinary skill in the art which additional elements to use.

Factors of importance in selecting a particular plasmid or viral vector include, but are not limited to, the ease with which recipient cells that contain the vector are recognized and selected from those recipient cells which do not contain the vector; the number of copies of the vector which are desired in a particular host; and whether it is desirable to be able to "shuttle" the vector between host cells of different species.

Once the vector(s) is constructed to include a DNA sequence for expression, it may be introduced into an appropriate host cell by one or more of a variety of suitable methods that are known in the art, including but not limited to, for example, transformation, transfection, conjugation, protoplast fusion, electroporation, calcium phosphate-precipitation, direct microinjection, etc.

After the introduction of one or more vector(s), host cells are usually grown in a selective medium, which selects for the growth of vector-containing cells. Expression of recombinant proteins can be detected by immunoassays including Western blot analysis, immunoblot, and immunofluorescence. Purification of recombinant proteins can be carried out by any of the methods known in the art or described herein, for example, any conventional procedures involving extraction, precipitation, chromatography, and electrophoresis. A further purification procedure that may be used for purifying proteins is affinity chromatography using monoclonal antibodies which bind a target protein. Generally, crude preparations containing a recombinant protein are passed through a column on which a suitable monoclonal antibody is immobilized. The protein usually binds to the column via the specific antibody while impurities pass through. After washing the column, the protein is eluted from the gel by changing pH or ionic strength, for example.

The nanoparticle and polymer compositions of the invention can also be used to achieve gene transfer. cDNA expression for use in polynucleotide therapy methods can be directed from any suitable promoter (e.g., the human cytomegalovirus (CMV) promoter), and regulated by any appropriate mammalian regulatory element. For example, if desired, enhancers known to preferentially direct gene expression in specific cell types can be used to direct the expression of a nucleic acid. The enhancers used can include, without limitation, those that are characterized as tissue- or cell-specific enhancers. Alternatively, if a genomic clone is used as a therapeutic construct, regulation can be mediated by the cognate regulatory sequences or, if desired, by regulatory sequences derived from a heterologous source, including any of the promoters or regulatory elements described above.

Methods for Evaluating Therapeutic Efficacy

In one approach, the efficacy of the treatment is evaluated by measuring, for example, the biological function of the treated organ (e.g., neuronal function). Such methods are standard in the art and are described, for example, in the Textbook of Medical Physiology, Tenth edition, (Guyton et al., W.B. Saunders Co., 2000). In particular, a method of the present invention, increases the biological function of a tissue or organ by at least 5%, 10%, 20%, 40%, 50%, 60%, 70%, 80%, 90%, 100%, 150%, 200%, or even by as much as 300%, 400%, or 500%. In one embodiment, the tissue is neuronal tissue.

In another approach, the therapeutic efficacy of the methods of the invention is assayed by measuring an increase or decrease in cell number in the treated tissue or organ as compared to a corresponding control tissue or organ (e.g., a tissue or organ that did not receive treatment). Preferably, cell number in a tissue or organ is increased or decreased, depending on the disease, by at least 5%, 10%, 20%, 40%, 60%, 80%, 100%, 150%, or 200% relative to a corresponding tissue or organ. Methods for assaying cell proliferation are known to the skilled artisan and are described, for example, in Bonifacino et al., (Current Protocols in Cell Biology Loose-leaf, John Wiley and Sons, Inc., San Francisco, Calif.). For example, assays for cell proliferation may involve the measurement of DNA synthesis during cell replication. In one embodiment, DNA synthesis is detected using labeled DNA precursors, such as [$^{3H}$]-thymidine or 5-bromo-2*-deoxyuridine [BrdU], which are added to cells (or animals) and then the incorporation of these precursors into genomic DNA during the S phase of the cell cycle (replication) is detected (Ruefli-Brasse et al., Science 302 (5650):1581-4, 2003; Gu et al., Science 302 (5644):445-9, 2003).

In one approach, therapeutic efficacy is assessed by measuring an increase or reduction in cell death, including apoptosis, depending on the disease. Apoptotic cells are characterized by morphological changes, including chromatin condensation, cell shrinkage and membrane blebbing, which can be clearly observed using light microscopy. The biochemical features of apoptosis include DNA fragmentation, protein cleavage at specific locations, increased mitochondrial membrane permeability, and the appearance of phosphatidylserine on the cell membrane surface. Assays for apoptosis are known in the art. Exemplary assays include TUNEL (Terminal deoxynucleotidyl Transferase Biotin-dUTP Nick End Labeling) assays, caspase activity (specifically caspase-3) assays, and assays for fas-ligand and annexin V. Commercially available products for detecting apoptosis include, for example, Apo-ONE® Homogeneous Caspase-3/7 Assay, FragEL TUNEL kit (ONCOGENE RESEARCH PRODUCTS, San Diego, CA), the ApoBrdU DNA Fragmentation Assay (BIOVISION, Mountain View, CA), and the Quick Apoptotic DNA Ladder Detection Kit (BIOVISION, Mountain View, CA).

Kits

The invention provides kits for the treatment or prevention of a neurological disease. In one embodiment, the kit includes a composition comprising a nanoparticle of the invention, e.g., a nanoparticle having a capture molecule (e.g., a ligand) that specifically binds a cell surface marker of a microglia, and a therapeutic and/or diagnostic agent. In some embodiments, the kit comprises a sterile container which contains a therapeutic or prophylactic composition; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

If desired an agent of the invention is provided together with instructions for administering the agent to a subject having or at risk of developing a disease. In certain embodiments, the disease is a neurological disease or disorder of the central nervous system, including a disease or disorder associated with neuroinflammation. In other embodiments, the disease or disorder is cancer or neoplasia. The instructions will generally include information about the use of the composition for the treatment or prevention of the disease or disorder. In other embodiments, the instructions include at least one of the following: description of the therapeutic agent; dosage schedule and administration for treatment or prevention of a neurological disease or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, therapeutic and/or diagnostic methods of the invention, and are not intended to limit the scope of what the inventors regard as their invention.

EXAMPLES

Example 1. Synthesis and Characterization of a New Class of Nanoparticles (NPs), Suitable for Drug and Gene Delivery and with Features Optimized for Surface Functionalization and in Vivo Administration A novel class of nanoparticles (NPs) were obtained, optimized for better biodistribution in vivo and for functionalization with: i) TSPO-selective ligands; ii) moieties allowing loading and controlled release of small molecules and/or oligodeoxynucleotides in vivo; and iii) functional groups allowing MRI/PET traceability (FIG. 1).

Figure 2A:
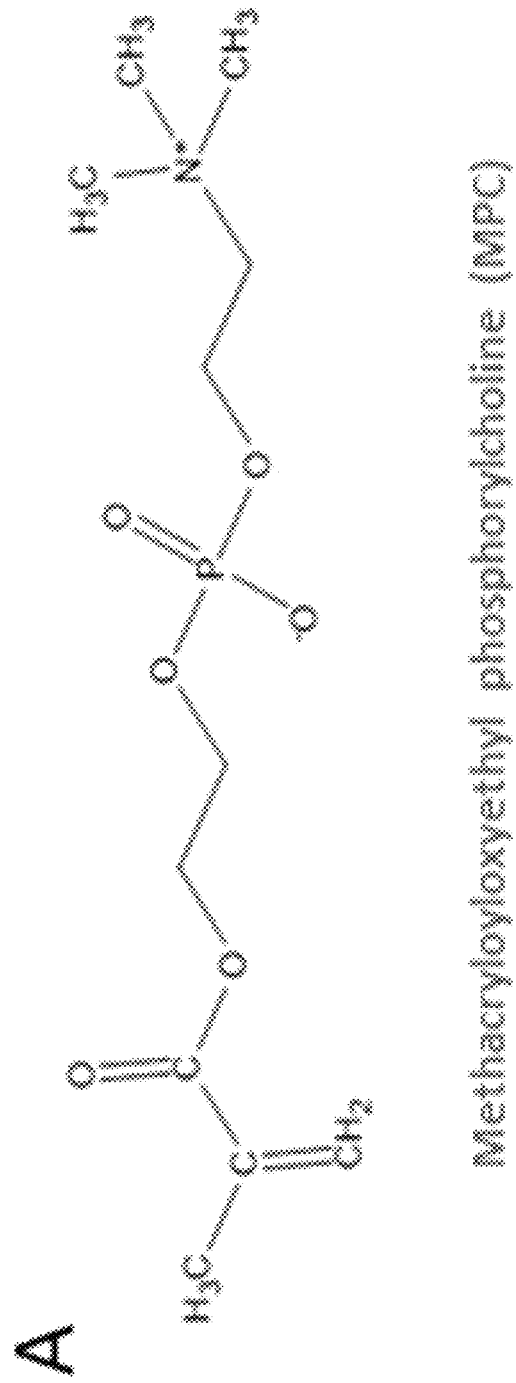
FIGS. 2A-2F depict monomers and block-copolymers generated in different steps to obtain MPC-based nanoparticles (NPs) with optimal dimensions, polyspersion, and suitable for functionalization for targeted applications.
Figure 2B:
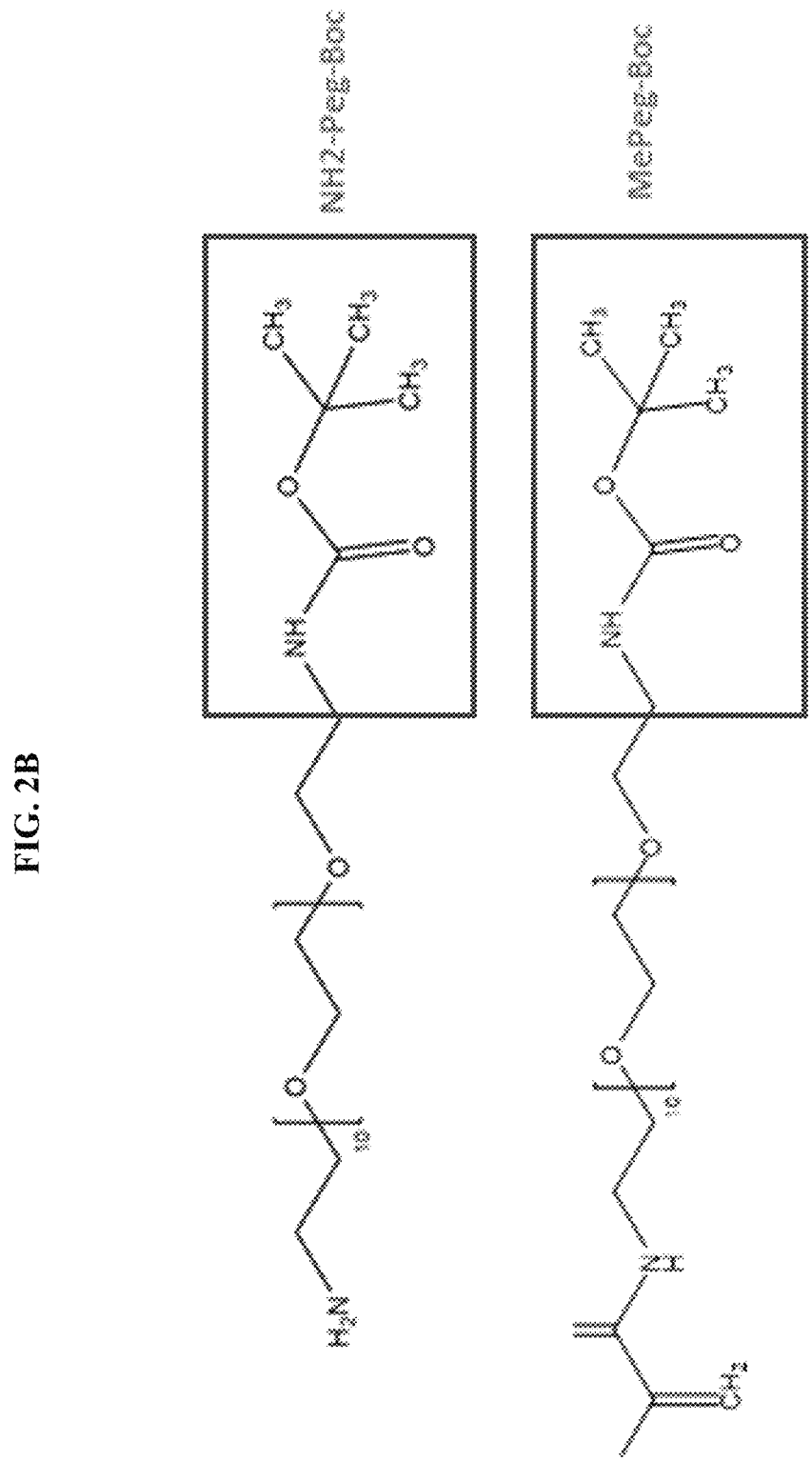
Figure 2D:
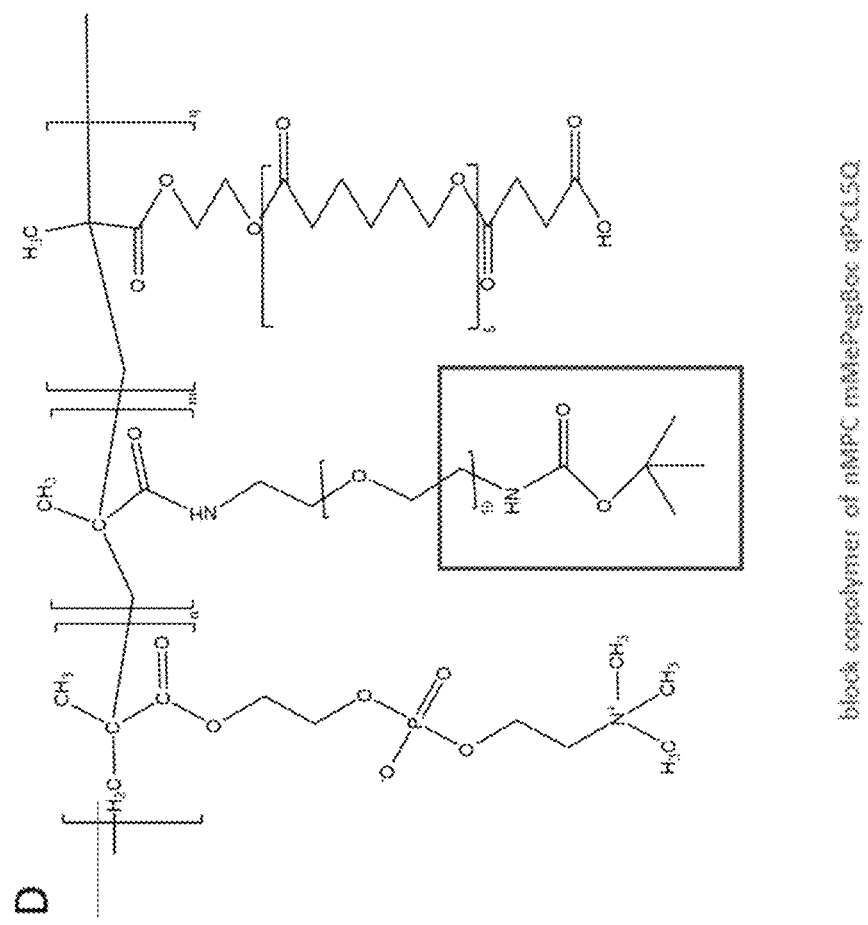
Figure 2C:
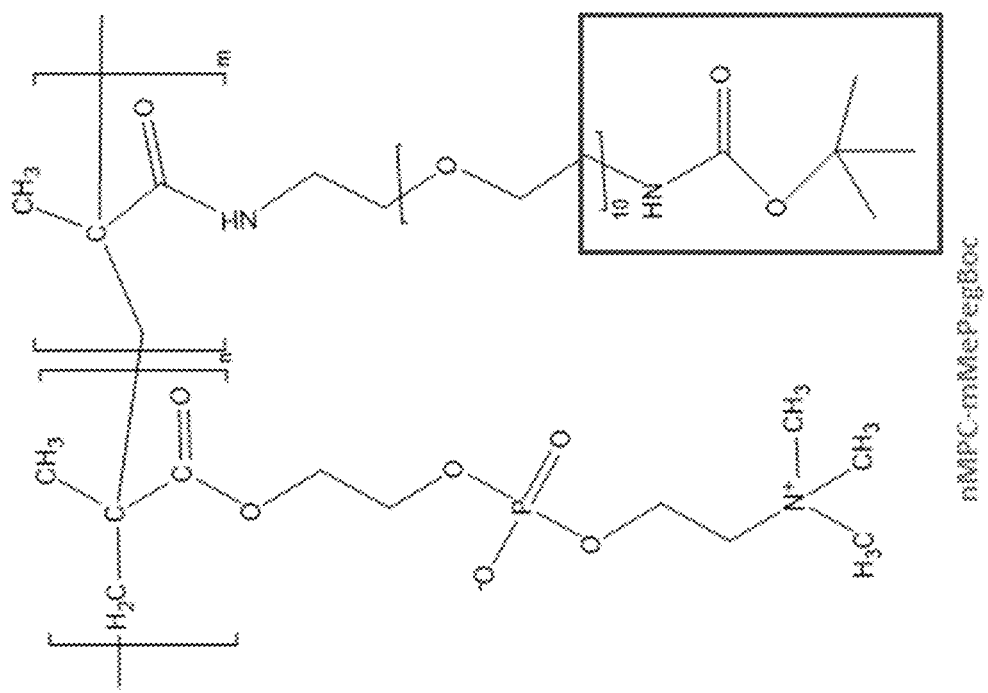
Figures 2E, 2F:
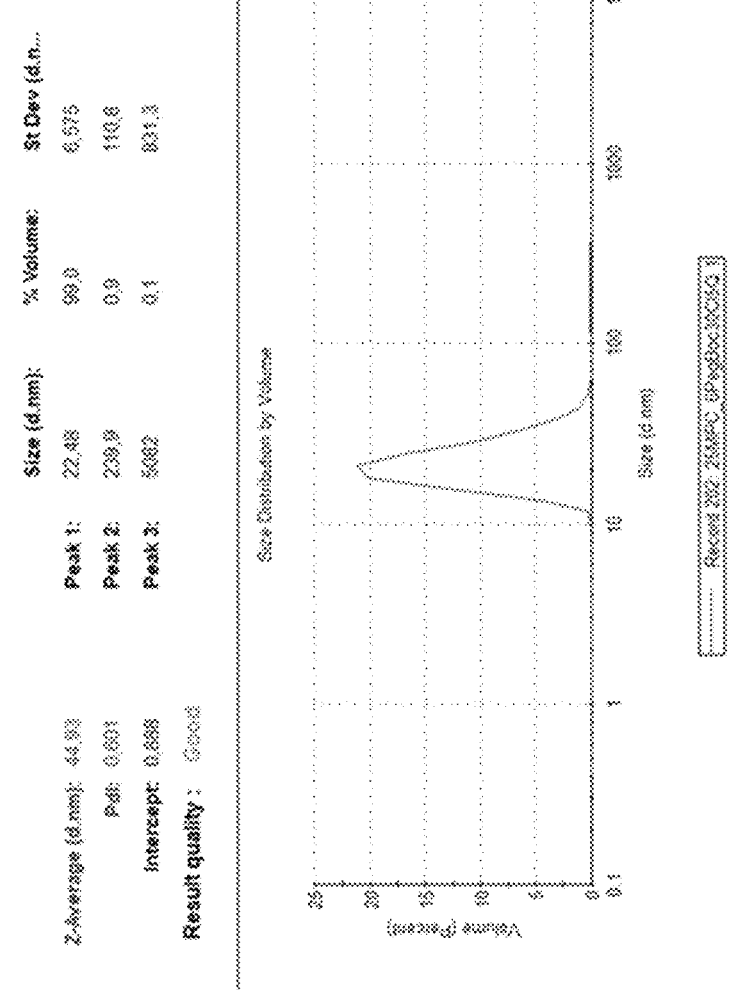

2-Methacryloyloxyethyl phosphorylcholine (MPC) was utilized as a starting monomer (FIG. 2A). MPC contains a phosphorylcholine group mimicking the phospholipid polar groups contained within cell membranes, resulting in high biocompatibility. In addition, a PEGylated monomer was specifically synthesized to covalently bind the precursors of translocator protein (TSPO) ligands already validated in the clinical setting, i.e. PK11195 and PBR28. In particular, the NH2-PEG-Boc (FIG. 2B) or, alternatively the NH2-PEG-N3 (FIG. 2F), precursor was first provided with a methacrylamide group (Me-PEG-Boc, FIG. 2B, or Me-PEG-N3, respectively) and subsequently polymerized together with MPC via RAFT (Reversible addition-fragmentation chain-transfer) polymerization in a ratio of 25:3 and 25:6. The conversion was evaluated by NMR, and the polymer was purified by dialysis and then precipitated in acetone (nMPC-mMePegBoc, FIG. 2C). This polymer was then used like a macro-RAFT agent to produce a block copolymer for the polymerization of a biodegradable hydrophobic monomer (HEMA-polycaprolactone5) modified with a COOH ending group. 25MPC-3MePeg-Boc and 25MPC-6MePegBoc were polymerized through RAFT polymerization with HemaC15Q and Hema-Rhodamine (FIG. 2D). The resulting block copolymer was nanoprecipitated to produce rhodaminated nanoparticles. These NPs (hereafter "NP-MPC") are about 45 nm in diameter and very homogeneous, with narrow polydispersion (FIG. 2E).

Figure 3A:
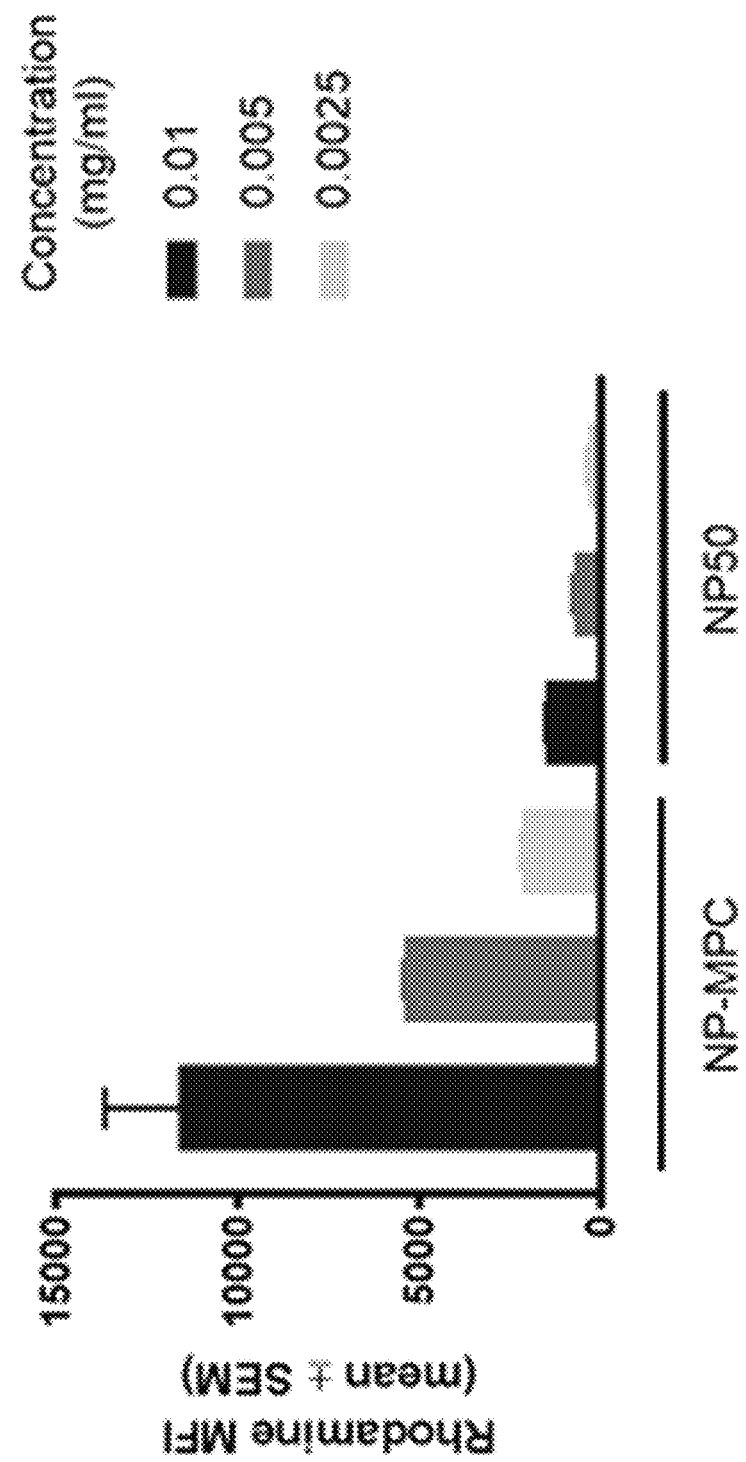
FIGS. 3A-3C depicts uptake of NP-MPC assessed in vitro and in vivo.
Figure 3B:
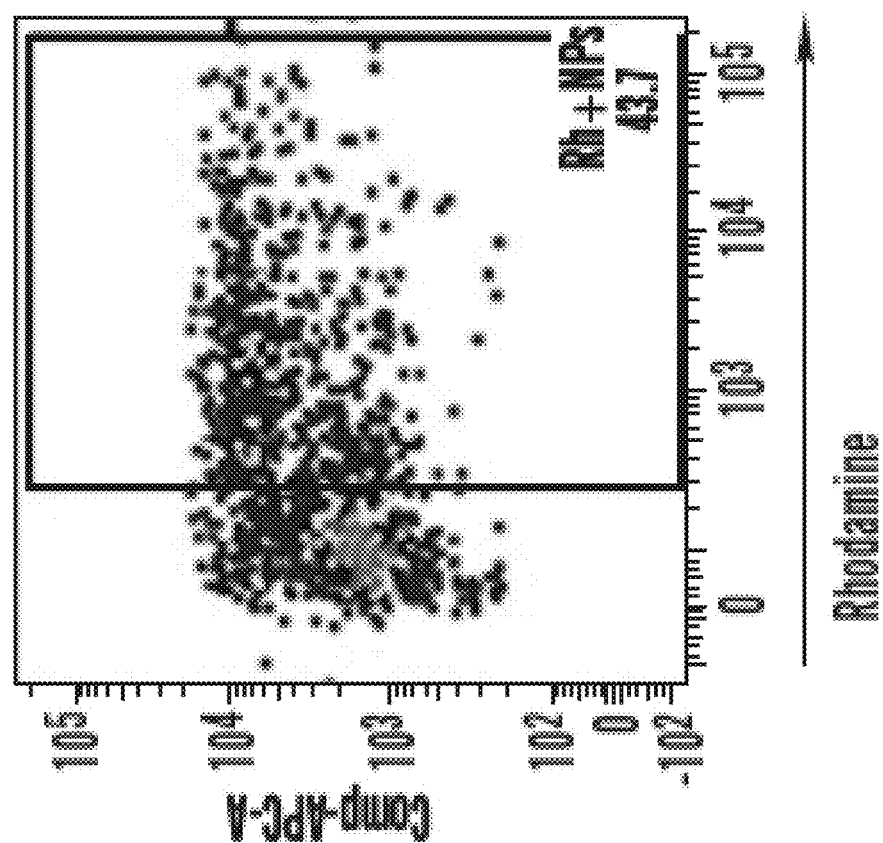
Figure 3B:
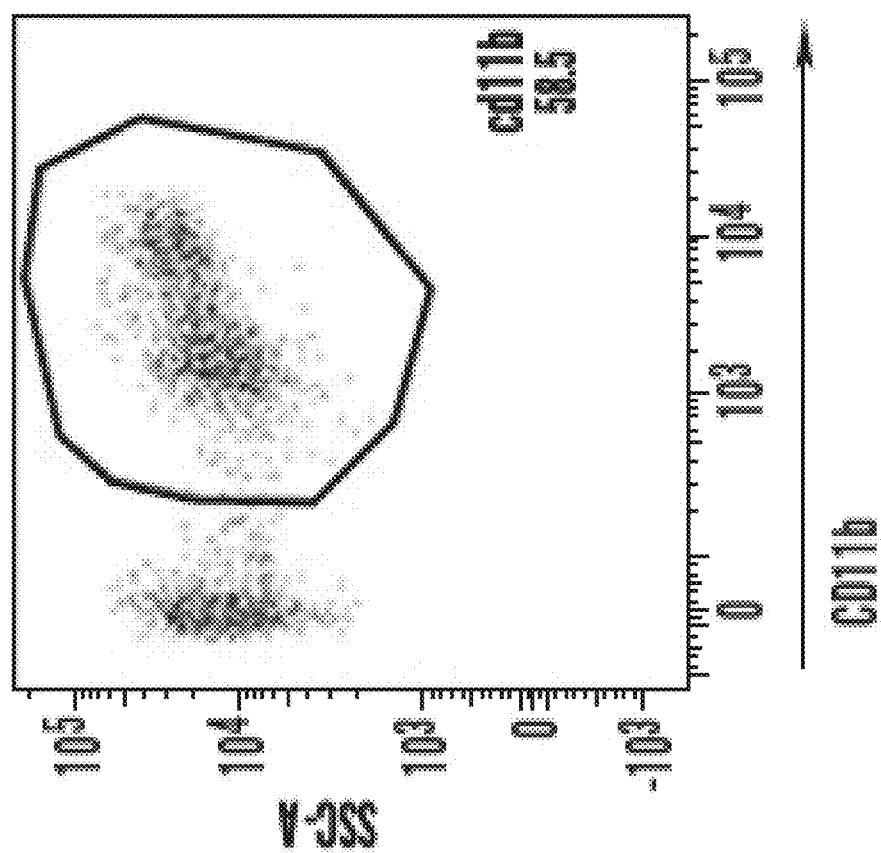
Figure 3C:
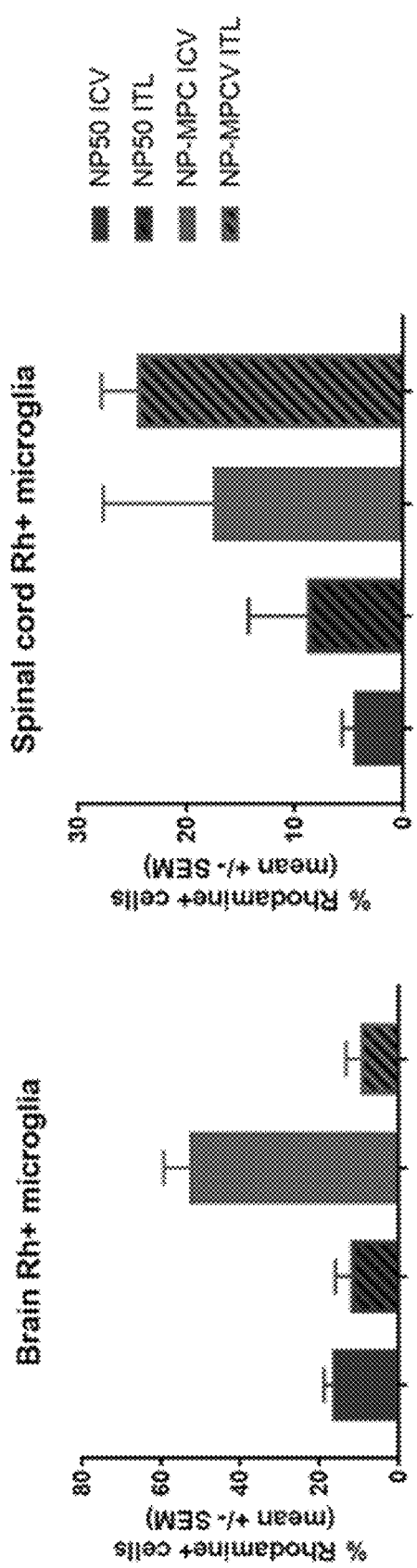

The uptake of NP-MPC was assessed in vitro in BV2 cell lines. NPs were added to cell culture medium at different concentrations for 24 hours; then cells were extensively washed and collected by trypsinization to analyze by flow cytometry the percentage of rhodamine$^+$ cells. A batch of rhodaminated NPs (hereafter called NP50 because their size is 50 nm) was also tested as reference. NP50 is non-functionalized and validated for microglia uptake. As shown in FIG. 3A, the uptake of NP-MPC was more efficient than NP50 at all tested concentrations. Interestingly, the in vitro results were recapitulated in the in vivo setting (FIGS. 3B-3C). Briefly, 5 µl of NPs (either NP-MPC or NP50 at 0.2% w/v in PBS), were administered to 12-15 week-old healthy mice in the cerebrospinal fluid (either intracerebroventricularly (ICV), i.e., in the cerebral lateral ventricles, or intrathecally into the lumbar region (ITL), i.e., in the subarachnoid space at lumbar level). All mice received an intraperitoneal injection of Mannitol 23% 1 hours after administration of NPs to obtain transient blood-brain barrier (BBB) disruption. Mice were then sacrificed 3 days after administration of NPs to analyze biodistribution of NPs by flow cytometry.

Figure 3G:
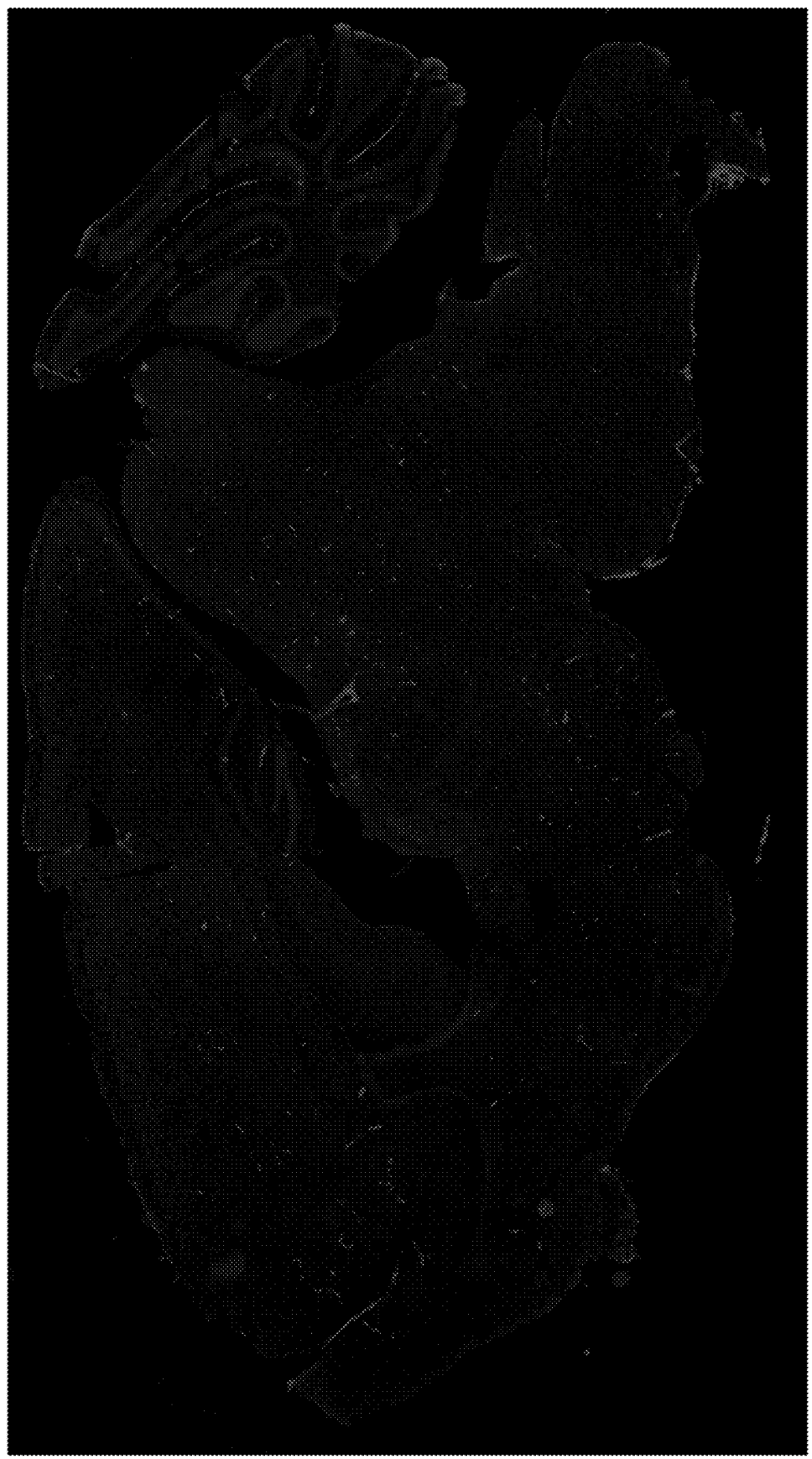
FIG. 3G depicts the brain biodistribution of NP-MPC upon intrathecal injection at lumbar level (ITL).

A striking increase in the percentage of rhodamine$^+$ microglia cells (identified by the CD45$^+$/CD11b$^+$ gating, FIG. 3B) was observed for NP-MPC in the brain (up to about 50% upon ICV injection) and in the spinal cord (up to almost 25% through both routes of administration) (FIG. 3C). The majority of administered NPs is internalized in CD45$^+$ cells (FIG. 3D), of which CD45$^+$/CD11b$^+$ microglia represents more than 90% (FIG. 3E). A few NPs (less than 10% of total) can be internalized in CD45$^-$ cells, mainly astrocytes and oligodendrocytes (FIG. 3F). As shown in FIG. 3G, ITL administration of NPs allows to obtain widespread distribution of NPs throughout the brain parenchyma.

Overall these data support NP-MPC as a suitable NP platform, with dimensions and surface features allowing widespread distribution in the brain and spinal cord, and uptake by microglia cells.

Example 2. Traceability of Nanoparticles (NPs) by Magnetic Resonance Imaging (MRI)

Figure 4B:
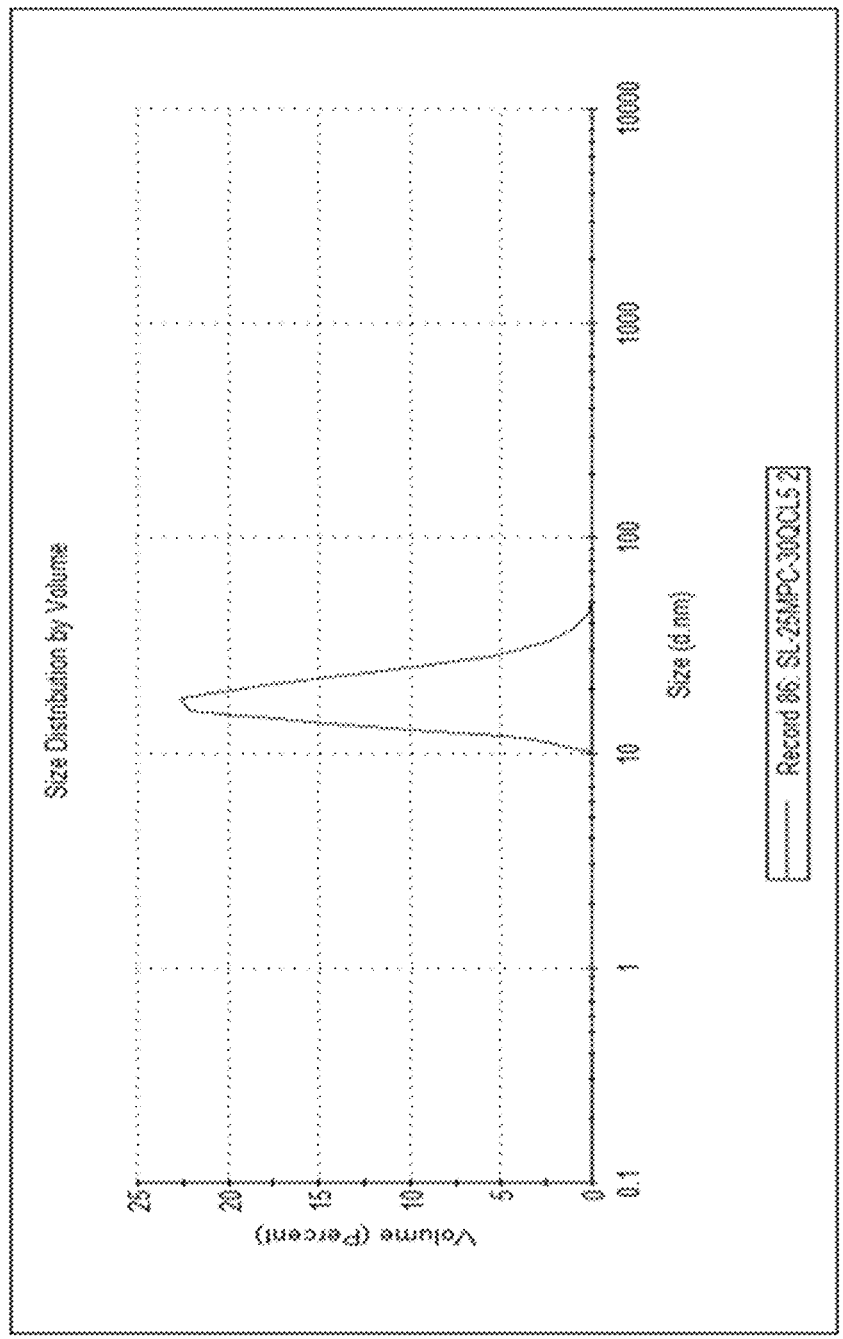
FIG. 4B is a series of graphs illustrating the dynamic light scattering analysis of MPC-NPs before and after loading of iron.
Figure 4B:
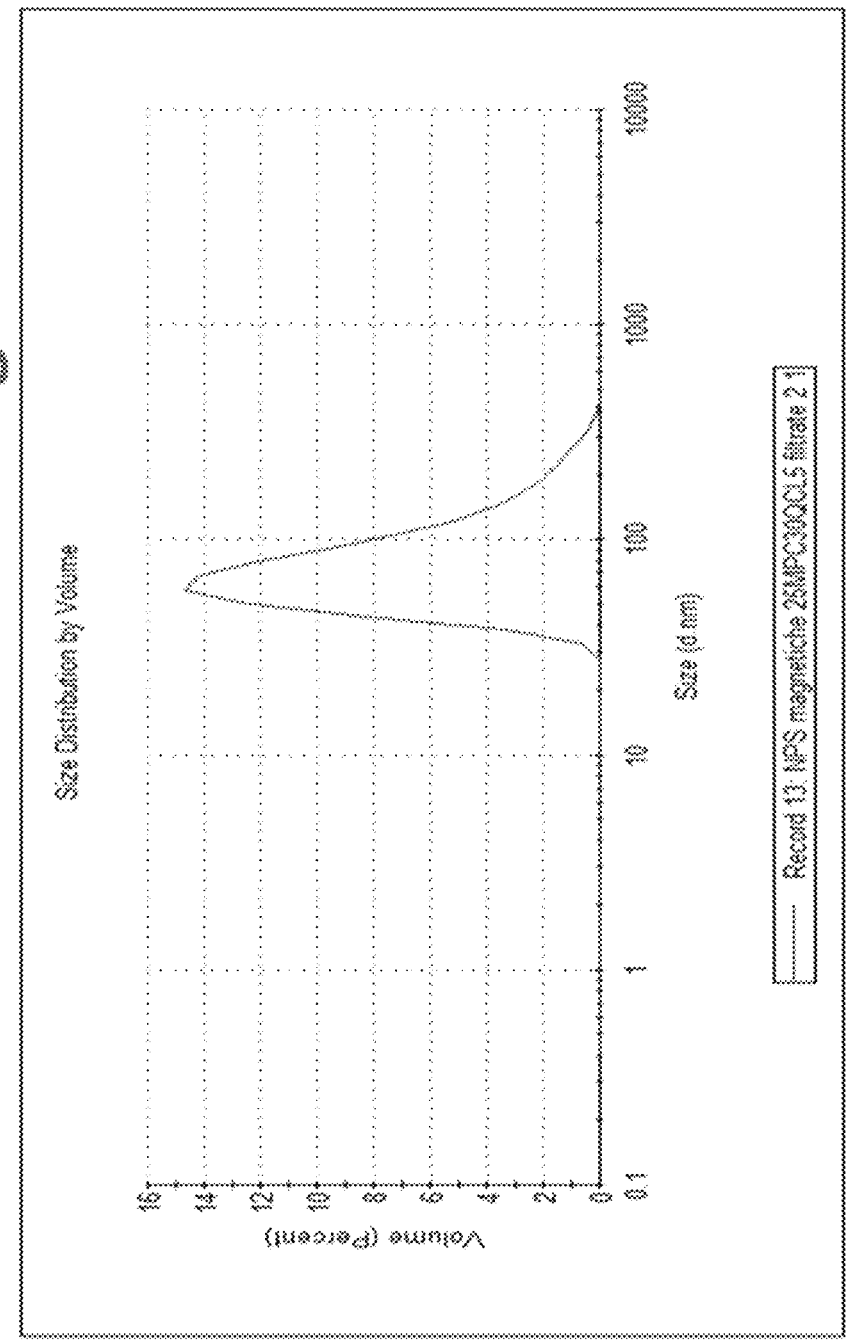

MPC was polymerized through RAFT polymerization. This polymer was then used like a macro-RAFT agent and chain extended with a biodegradable hydrophobic monomer (HEMA-polycaprolactone5) modified with a COOH ending group (FIG. 4A) to obtain a block copolymer suitable for stabilizing superparamagnetic nanoparticles in aqueous environment. 25MPC block-copolymer was polymerized through RAFT polymerization with HemaC15Q and HEMA-Rhodamine, purified, and precipitated in diethyl ether; then it was solubilized in 3 ml of DMSO and nanoprecipitated in 20 ml of water under strong stirring. FeCl$_2$ (43 mg) and FeCl$_3$ (117 mg) were solubilized in 5 mL of distilled water, stirred for 30 minutes, and then combined with the NPs in a round bottom flask under strong stirring after degassing for 30 minutes. NH$_3$ 28% (1.2 ml) was then added dropwise and left under strong stirring for 30 minutes. The resulting magnetic nanoparticles were then neutralized with HCl 0.1 M, dialyzed, filtered (0.4 µm) and analyzed through dynamic light scattering (FIG. 4B).

Different batches were produced (Table 1) by using different molar ratios of iron/polymer or by adopting different formulation chemistries. SPION 1 through 7 are made by employing a PCL-based polymer platform obtained from the RAFT polymerization of PEGMA2000 for the hydrophilic block and HEMA-CL5 for the hydrophobic one. Two different strategies were adopted to coat the SPIONs with this polymer.

1. SPIONs 1, 2 and 3

SPIONs have been synthesized following the co-precipitation method developed by Massart. More specifically, FeCl$_3$ and FeCl$_2$ have been used as the precursors and dissolved in water in a 2:1 mole ratio. Oleic acid was used as the stabilizer in an amount as to obtain a 50% magnetite content over the total nanoparticle weight, dissolved in acetone, and added to the precursor solution. Magnetite precipitation was allowed by the addition of a 28-30% w/w ammonium hydroxide aqueous solution at 80° C. The SPION suspension was stirred at 80° C. for 1 hour in order to let the precipitation and the binding of the oleic acid to occur. Then a 10-fold excess of acetone (with respect to water) was added to precipitate the magnetite, which was collected with a magnet. The SPIONs were washed three times with acetone and then dried at room temperature overnight. The nanoparticles were resuspended in tetrahydrofuran under magnetic stirring. Different percentages of the polymer were added to this organic solution and further precipitated in water under probe sonication for 30 minutes. The tetrahydrofuran was finally removed via dialysis.

2. SPIONs 4, 5, 6 and 7

For SPIONs 4 to 7, polymer was functionalized with carboxyl end groups in order to let its directly use as the stabilizer during the SPION synthesis. The necessary amount of polymer to obtain a 20% magnetite content over the total weight of the nanoparticles was dissolved in DMSO with a concentration of 10% w/w. The organic phase was added dropwise to the aqueous solution of FeCl$_3$ and FeCl$_2$ (with the same 2:1 mole ratio as described previously). After stirring for 30 minutes, the system was heated to 80° C. and ammonium hydroxide was added under vigorous agitation to obtain the magnetite precipitation. The SPIONs were collected with a magnet after the addition of a 10-fold excess of acetone and dialyzed against water for three days.

3. SPIONs 8 and 9

SPIONs 8 and 9 are based on the NP-MPC platform. MPC was polymerized through RAFT polymerization. This polymer was then used like a macro-raft agent to produce a block copolymer for the polymerization of a biodegradable hydrophobic monomer (HEMA-polycaprolactone5) modified with a COOH ending group (FIG. 4A). 25MPC block-copolymer was polymerized through RAFT polymerization with the HemaCl5Q and HEMA-Rhodamine, purified, and then precipitated in diethyl ether. It was then solubilized in DMSO and nanoprecipitated in water under strong stirring. FeCl$_2$ and FeCl$_3$ were solubilized in distilled water and left under stirring for 30 minutes and then combined with the NPs in a round bottom flask under strong stirring after degassing for 30 minutes. 1.2 ml of NH$_3$ 28% was added dropwise and underwent strong stirring for 30 minutes. The resulting magnetic nanoparticles were then neutralized with HCl 0.1 M, dialyzed, filtered (0.4 µm) and analyzed through dynamic light scattering (FIG. 4A). For SPION 9, a new method of production was adopted, consisting of a one-pot procedure. Briefly, the poly(MPC) was synthesized as described previously. After 24 hours of reaction at 65° C., the monomer conversion was evaluated at higher than 99%, so the chain extension with the HEMA-CL5Q could be carried out without intermediate purification steps. In particular, 0.94 g of HEMA-CLSQ (target DP=30), 2 mg of HEMA-Rhodamine and 4 mg of ACVA (macro CTA/ACVA=3) were dissolved in 1 g of ethanol and added to the solution containing the macro CTA. The reaction was left to occur for an additional 24 hours at 65° C. during which the simultaneous chain-extension of the macro CTA with the hydrophobic HEMA-CLSQ and the block copolymer self-assembly occur. Therefore, the traditional post-polymerization processes to obtain NPs from amphiphilic block copolymers, such as nanoprecipitation, emulsion-evaporation (which generally require dilute conditions) were avoided in this case.

Figure 4C:
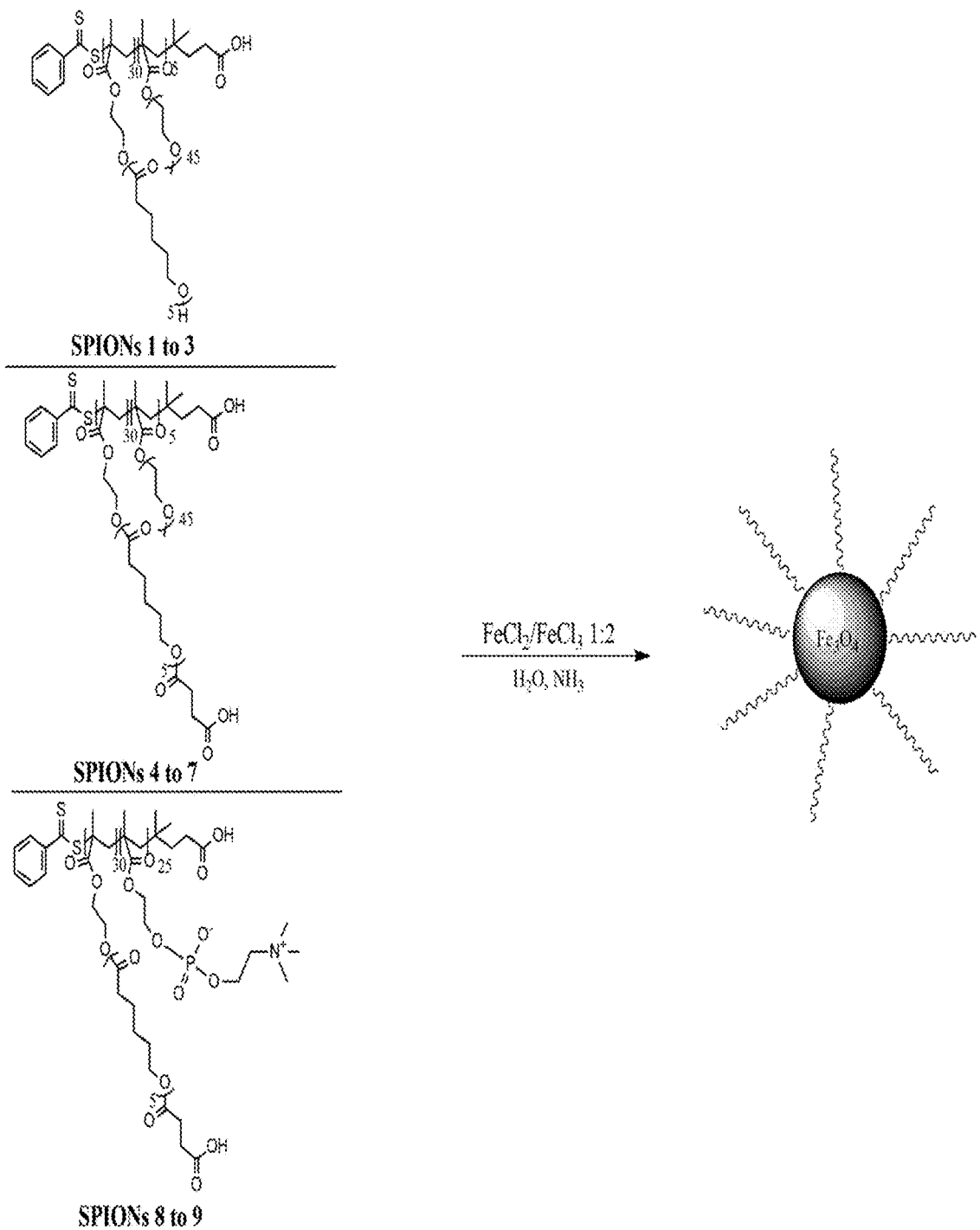
FIG. 4C outlines the main features of the polymers used to prepare SPIONs 1-3, SPIONs 4-7 and SPIONs 8-9.

FIG. 4C outlines the main features of the polymers used to prepare SPIONs 1-3, SPIONs 4-7 and SPIONs 8-9.

TABLE 1

Features of the different paramagnetic nanoparticle batches tested ("PDI" denotes polydispersity index).

| Batch ID | Diameter (nm) | PDI | Loaded compound | Conc. Iron (% w/wNPs) | Fluorescence |
|---|---|---|---|---|---|
| SPION 1 | 145 | 0.28 | Fe3O4 | 2.5 | none |
| SPION 2 | 99 | 0.26 | Fe3O4 | 5 | none |
| SPION 3 | 92 | 0.32 | Fe3O4 | 10 | none |
| SPION 4 | 111 | 0.3 | Fe3O4 | 20 | Rhodamine |
| SPION 5 | 191 | 0.21 | Fe3O4 | 20 | Rhodamine |
| SPION 6 | 105 | 0.28 | Fe3O4 | 15 | Rhodamine |
| SPION 7 | 79 | 0.31 | Fe3O4 | 15 | Rhodamine |
| SPION 8 | 101 | 0.24 | Fe3O4 | 20 | Rhodamine |
| SPION 9 | 121 | 0.31 | Fe3O4 | 20 | Rhodamine |

The efficiency of uptake of the different NPs batches was assessed on BV2 cell lines. Cells were plated on glass coverslips (30,000 cells/well in 24-well plates) and then incubated with different concentration of SPIONs (in the range 0.2-0.05 mg/ml polymer) for 24 hours. The different batches were matched for the amount of total polymer added in culture, irrespectively of the total amount of iron content. After the incubation, the cells were fixed with 4% buffered paraformaldehyde for 20 min at room temperature (RT). Then cells were permeabilized for 15 min at RT with 0.1% Triton in PBS. Total iron content was visualized by Prussian Blue staining (consisting in the incubation for 2 hours at RT with a solution made of 2.5% hydrochloric acid, 2.5% potassium ferrocyanide). Cells were finally counterstained with Nuclear Fast Red and mounted on microscopy slides.

Figure 4D:
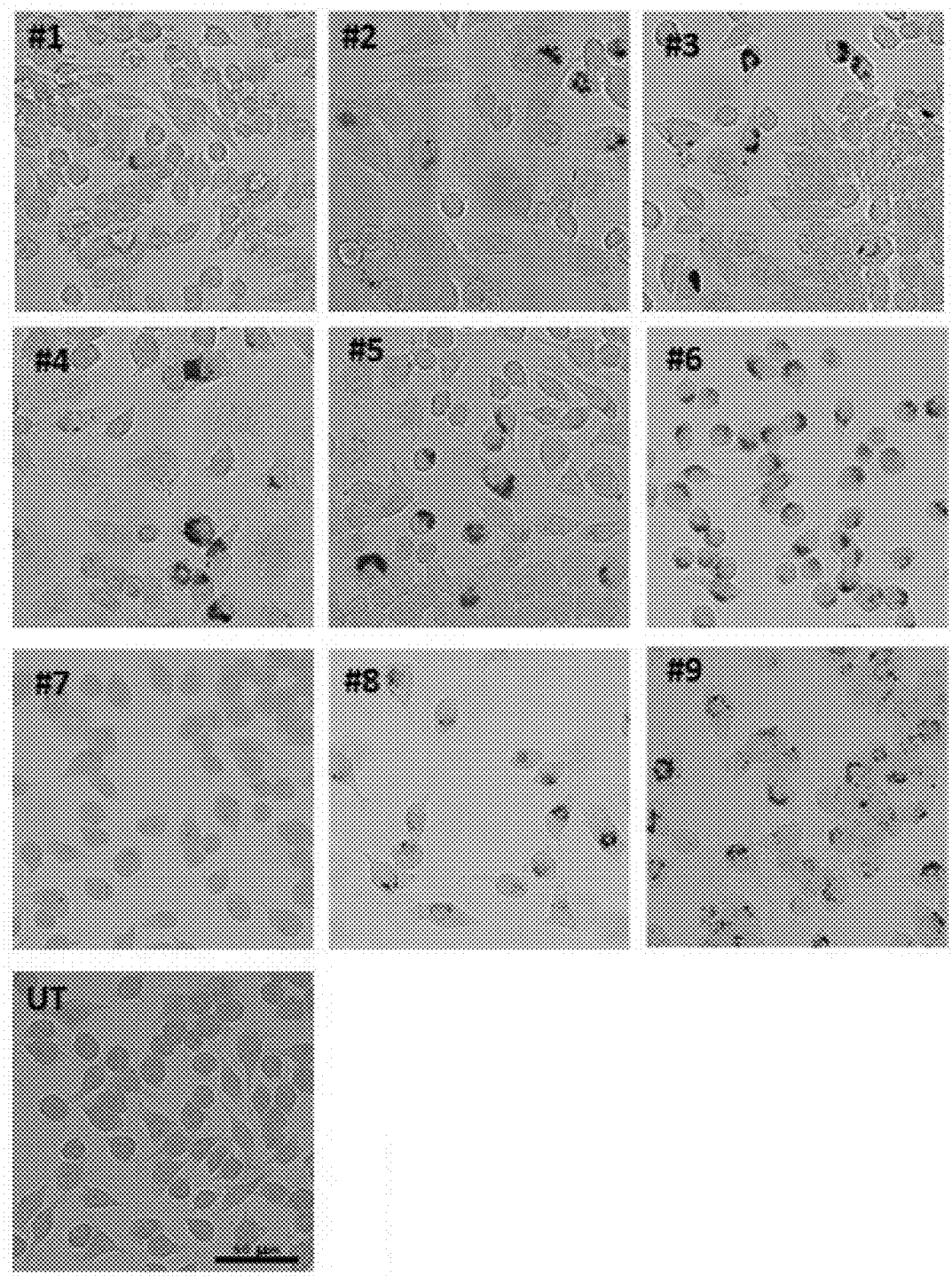
FIG. 4D depicts representative brightfield microscopy microphotographs and corresponding quantification of iron content BV2 cells exposed to different SPION batches (tested at 0.2 mg polymer/ml).
Figure 4E:
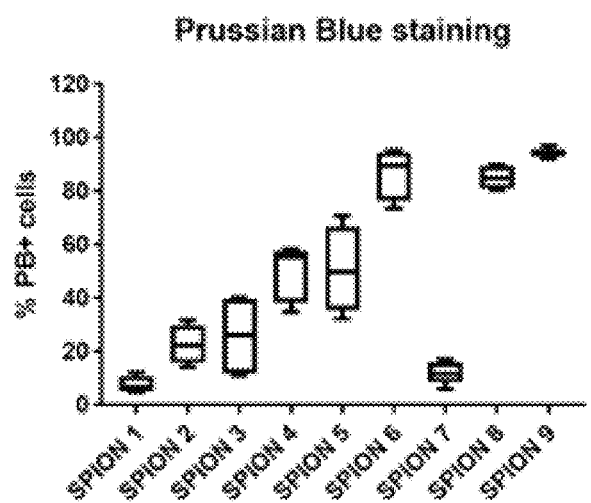
FIG. 4E is a graph quantifying the results observed in FIG. 4D.

For SPION 4 through 9 (rhodaminated NPs), a fraction of the cells was also collected after trypsinization and then analyzed by flow cytometry to evaluate the total percentage of rhodamine positive cells, as measurement of the overall NPs uptake. As shown in FIG. 4D, iron was detected in all the tested conditions. However, the best results in terms of number of cells showing detectable amounts of iron were obtained with SPION 6, 8, and 9 (see FIG. 4E).

Figure 4F:
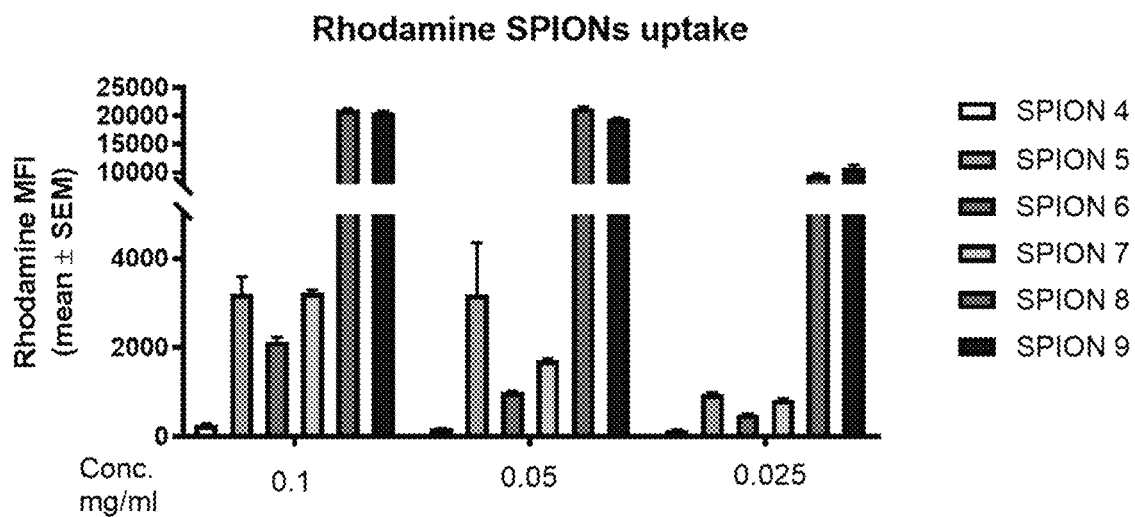
FIG. 4F is a graph depicting rhodamine signal detected by flow cytometry in BV2 cells exposed to different concentrations of fluorescent labelled SPION batches numbered SPION 4 through 9.

For SPION 4 through 9, the efficiency of uptake was verified by flow cytometry, reporting almost 100% of cells that were rhodamine$^+$ at all tested SPION concentrations (0.1, 0.05, and 0.025 mg/ml). Measurement of the mean fluorescence intensity of rhodamine signal highlighted a higher efficiency of uptake for SPION 8 and 9 (FIG. 4F), which was in line with the striking efficiency of uptake previously reported for NP-MPC.

Figure 5A:
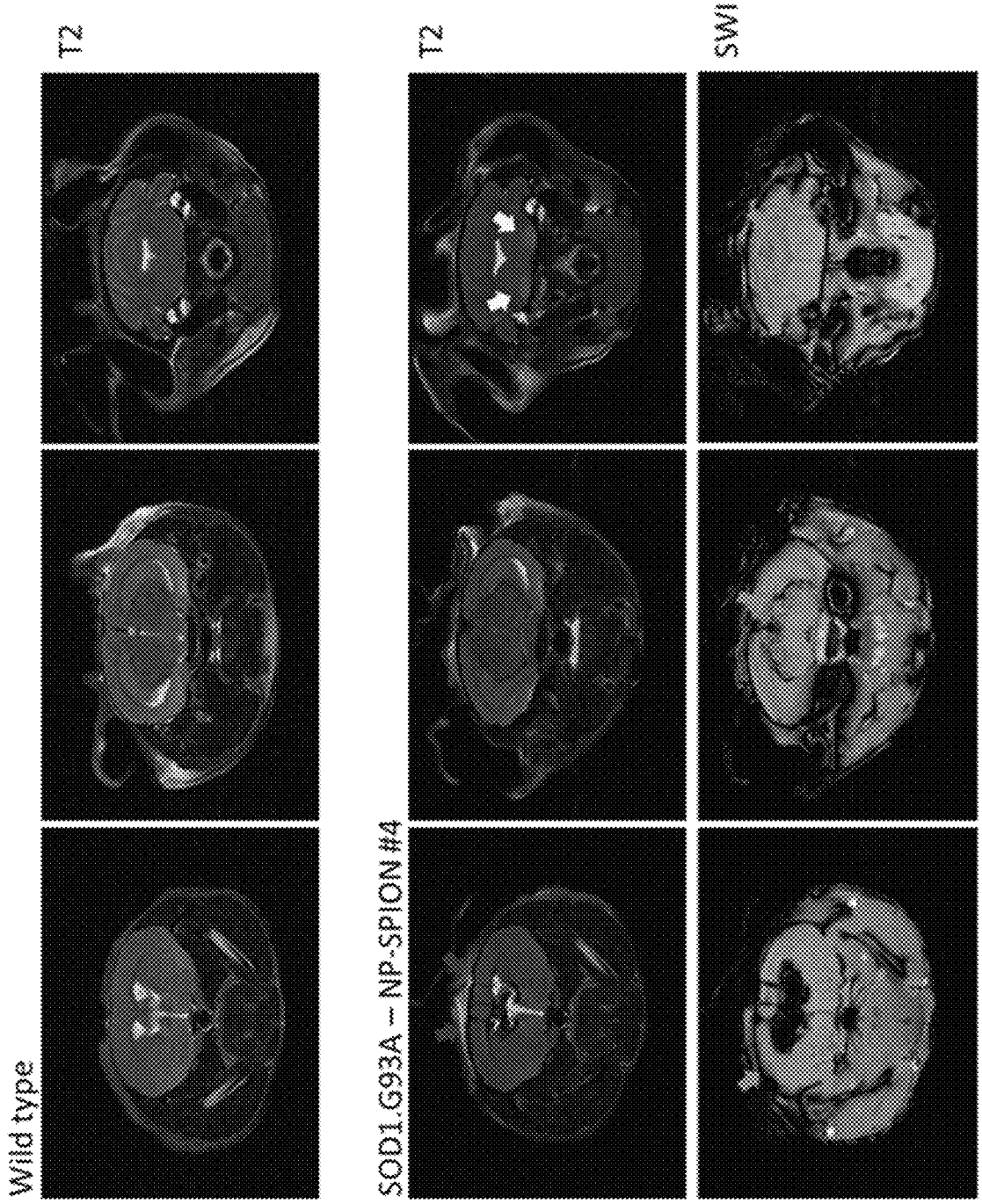
FIGS. 5A-5B depict NP biodistribution in vivo by MM.
Figure 5B:
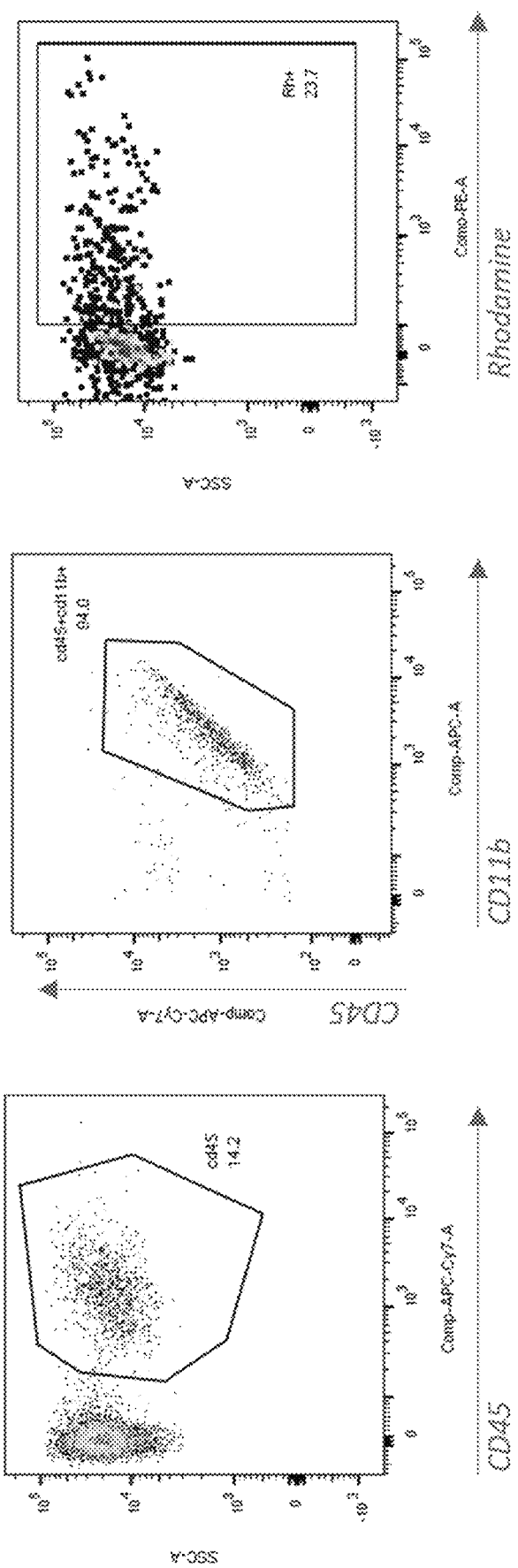

As proof of concept for detecting NPs biodistribution in vivo by MRI, SPION 4 nanoparticles were administered (5 μl total volume) ICV to symptomatic SOD1.G93A or to wild type mice. Three (3) days after administration, mice underwent MRI (T2 anatomical axial and sagittal view, T2 and T2* maps and susceptibility weight imaging, SWI maps). As shown in FIG. 5A (arrows in SWI panels), a massive NP signal was detected in the lateral ventricles and strikingly, positively widespread throughout the cerebral cortex, rostral to caudal. As expected for symptomatic SOD1.G93A mice, T2 images highlighted hyper-intensive signal in the trigeminal (not shown), hypoglossal (not shown) and facial nucleus (yellow arrows in FIG. 5A, arrows in right T2 panel). Cytofluorimetric analysis of rhodaminated NP-SPION biodistribution confirmed uptake by CNS CD45$^+$/CD11b$^+$ microglia cells (FIG. 5B).

Example 3. Traceability of Nanoparticles (NPs) by Positron Emission Tomography (PET)

As described above, NPs-MPC have been designed as an innovative platform allowing multiple functionalization. The goal is to exploit these NPs not only for MM but also for PET imaging. The advantage of PET over MRI is that this technique is highly sensitive and allows precise quantification of the radionuclide in vivo. Thus, PET traceable NPs will be instrumental for monitoring and quantifying neuroinflammation in vivo. Cytofluorimetric analyses and in vivo MM data showed many NPs still detectable in the CNS at 3 days after injection. The levels of NPs are stable up to about 7 days post-injection. Afterwards they are gradually degraded and washed out of the tissue within about 30 days. Thus, for PET, a radioisotope was chosen with a half-life fitting the dynamics of NP biodistribution in vivo. Zirconium$^{89}$ ($^{89}$Zr), with a half-life of 78.4 hours (about 3 days) was identified as the best isotope suited for these studies. The conjugation of Deferoxamine (a chelator) to NP-MPCs was identified as an important step necessary to allow efficient loading of Zirconium$^{89}$ on the NPs. The reaction can be performed in aqueous solution; thus, the loading of the radionuclide on the surface of the preformed NPs is envisaged.

Figure 6A:
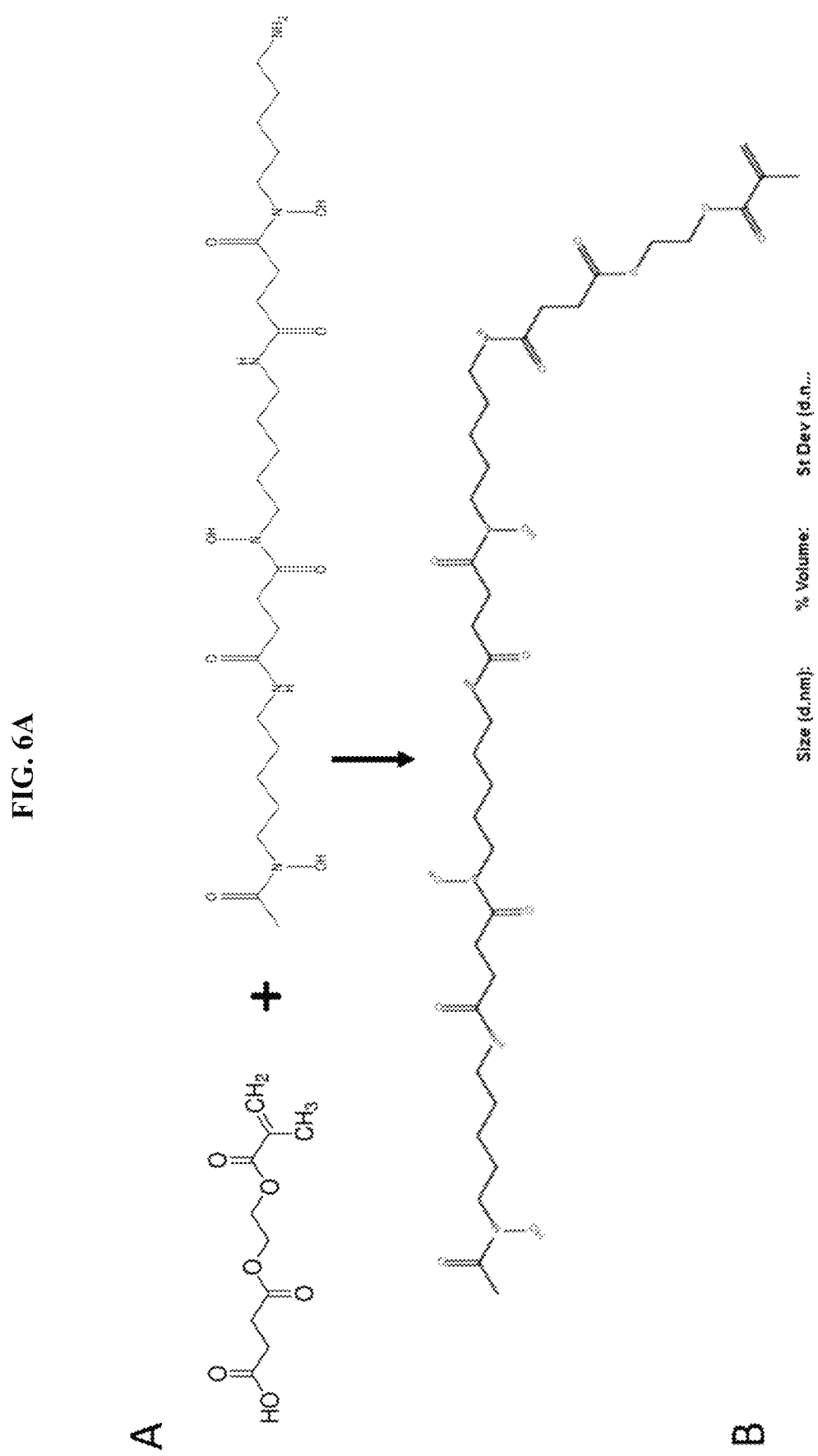
FIG. 6A depicts functionalization of Hema-succinate with deferoxamine (DFO), to form Hema-DFO, a building block used to produce NP-MPC functionalized on the surface with DFO.
Figure 6B:
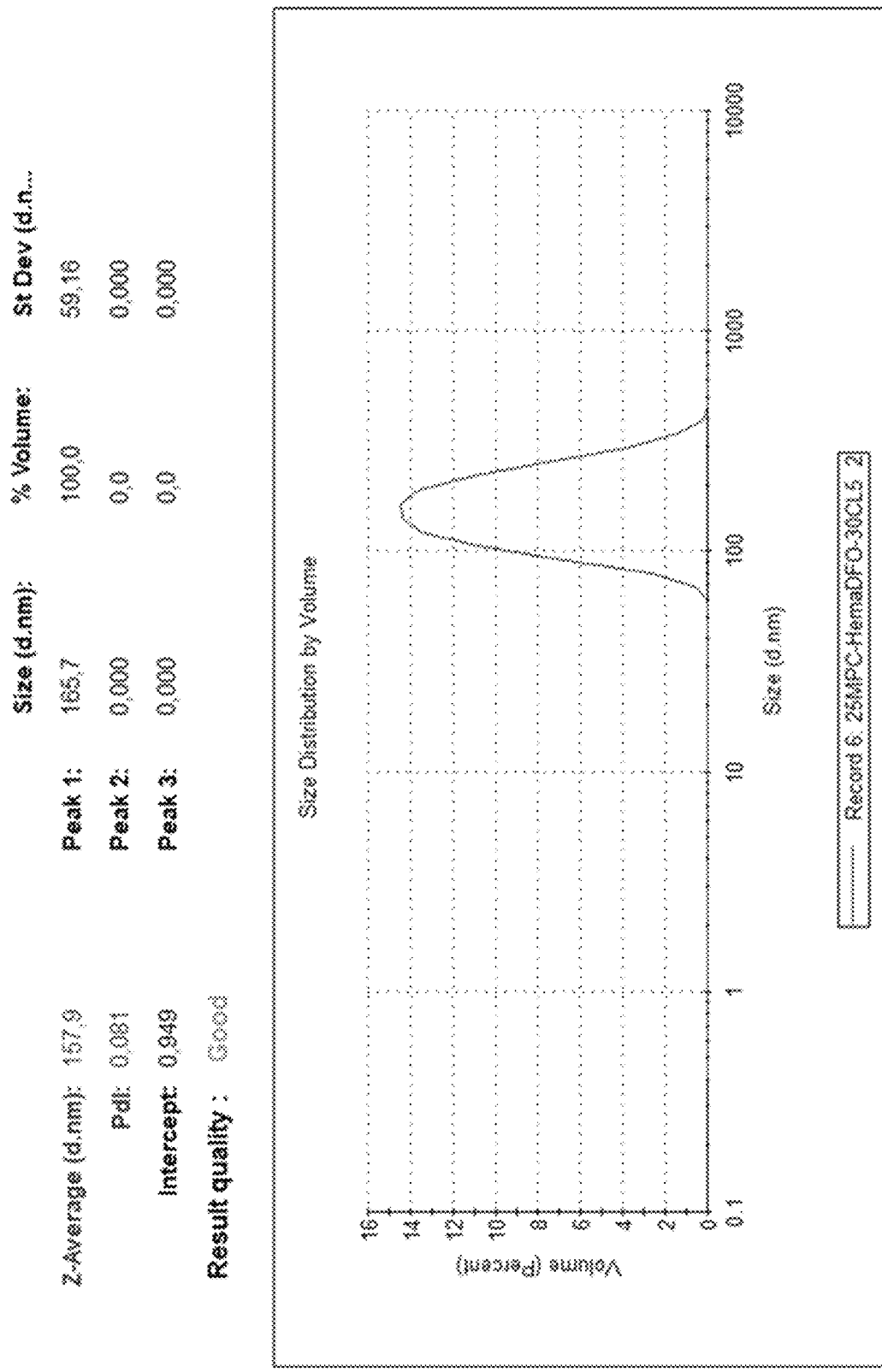
FIG. 6B depicts dynamic light scattering (DLS) analysis of DFO-NPs.

A strategy to conjugate covalently deferoxamine on the surface of NP-MPCs is depicted (shown in FIG. 6A). MPC was polymerized through RAFT polymerization. Mono-2-(Methacryloyloxy)ethyl succinate was functionalized with deferoxamine (DFO) mesylate though steglich esterification. The so called Hema-DFO was then polymerized with 25MPC to create a hydrophilic macro-agent functionalized with DFO. 25MPC-HemaDFO was polymerized through RAFT polymerization with HemaC15 and HemaRhodamine. The block copolymer so created was nanoprecipitated to produce nanoparticles with diameters of about 160 nm (FIG. 6B).

Figures 6C, 6D:
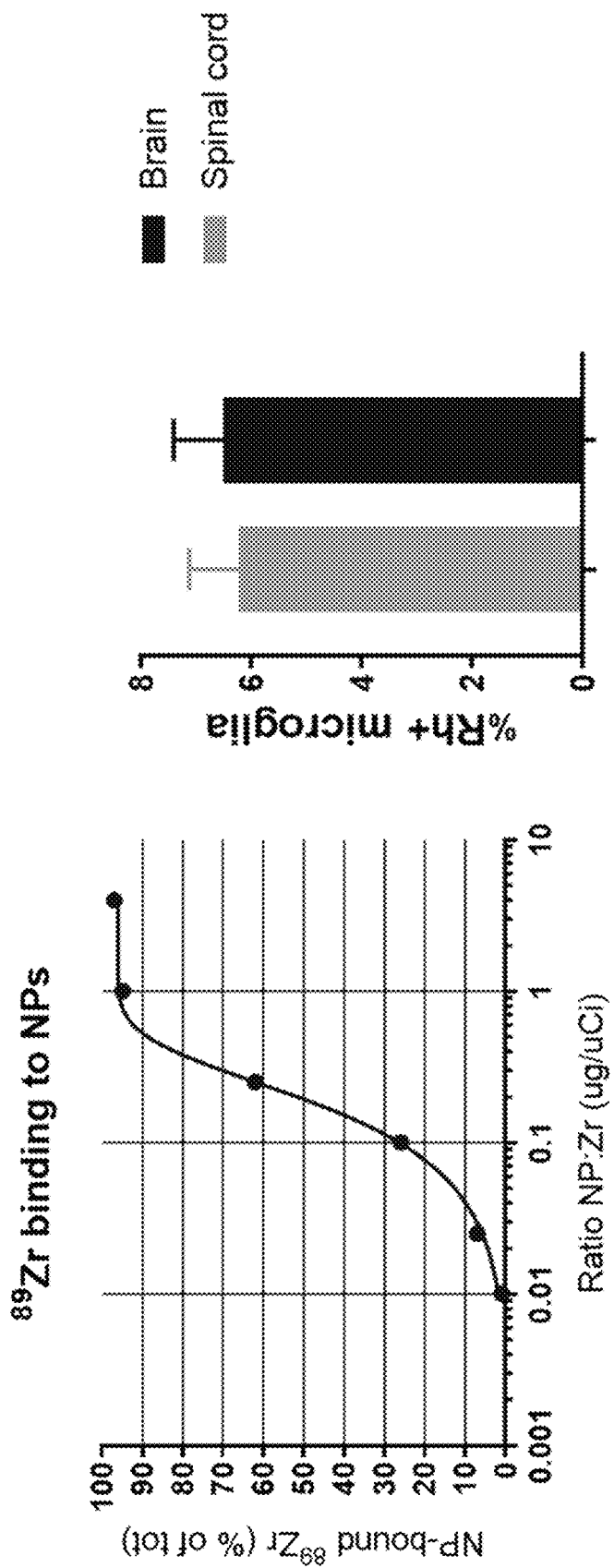
FIG. 6C depicts the binding profile of NP-MPC functionalized with DFO for the radioisotope $^{89}Zr$.
FIG. 6D depicts the internalization of rhodaminated NP-MPC functionalized with DFO (assessed by flow cytometry) in microglia cells from mouse brain and spinal cord.

To determine the extent of nanoparticle (NP) DFO functionalization, the following $^{89}$Zr binding assay was performed: Six concurrent radiolabeling reactions were run using ~100 μCi of $^{89}$Zr oxalate each, and varying quantities of DFO-functionalized nanoparticles (FIG. 6C). After 60 minutes, each crude reaction mixture was analyzed by radio-TLC, where unbound $^{89}$Zr was found to migrate with the 20 mM sodium citrate solvent front while NPs remained at the baseline. Using the previously determined $^{89}$Zr decay-corrected specific activity (Ci/μmol) and the radio-TLC data (% bound vs. unbound), calculation of the DFO:NP functionalization ratio was estimated to be ~4.7:1. Without being bound by theory, the current DFO functionalization ratio allows for an injectable product activity to mass ratio of approximately 100 μCi per 100 of NPs.

As shown in FIG. 6D, NPs functionalized with DFO can also be conjugated covalently to a rhodamine dye, allowing cytofluorimetric analyses or fluorescence microscopy to detect NP internalization and biodistribution to a greater extent than PET. This further supports the suitability of the NP platform presented herein for the generation of multi-traceable compounds.

Figure 7A:
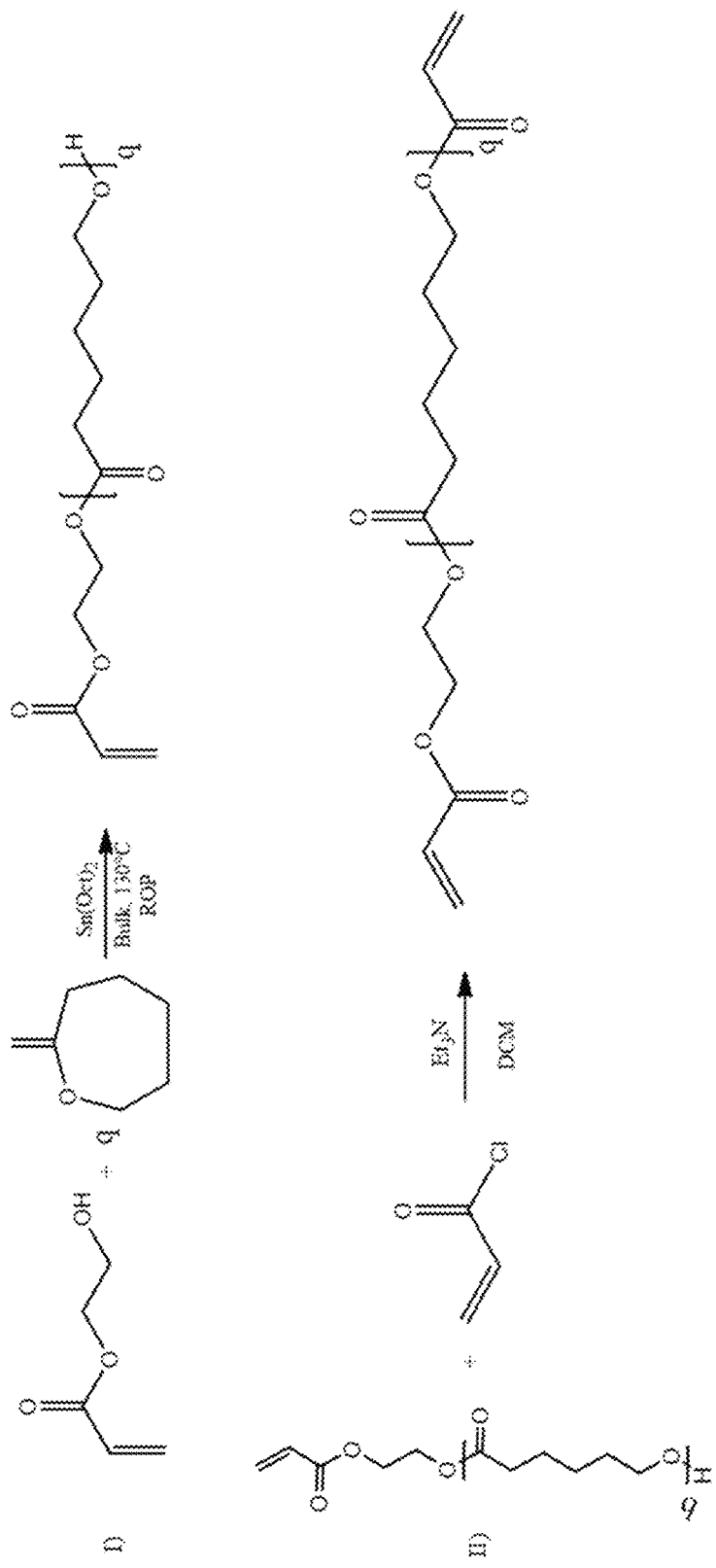
FIG. 7A depicts synthesis of the poly-caprolactone-based diacrylate.

Example 4. Non-Viral Nanoparticle-Mediated Gene Delivery: Preliminary Tests of the Loading Efficiency and Release Profile of Polymers Designed as Carriers for Gene Delivery Poly (β-amino esters) (PBAEs) are a class of polymers particularly promising for gene delivery due to their facile synthesis, transfection efficiency, and degradability. PBAEs are usually produced in two steps that consist of (i) a step growth polymerization (Michael addition) between amines and a diacrylate and (ii) an end-capping of the final polymer with a diamine. The multiple ester bonds present in the polymer backbone can be degraded in the body via hydrolysis. Here, diacrylates in the synthesis of PBAE terpolymers were substituted with PCL-based ones that are expected to be more biocompatible. The PCL-based diacrylates were synthesized via a two-step procedure that consists of (i) a ring opening polymerization of caprolactone (CL) with hydroxyethylacrylate (HEA) as initiator and tin(II)-ethylhexanoate as catalyst and (ii) acylation with acryloyl chloride (FIG. 7A).

Figure 7B:
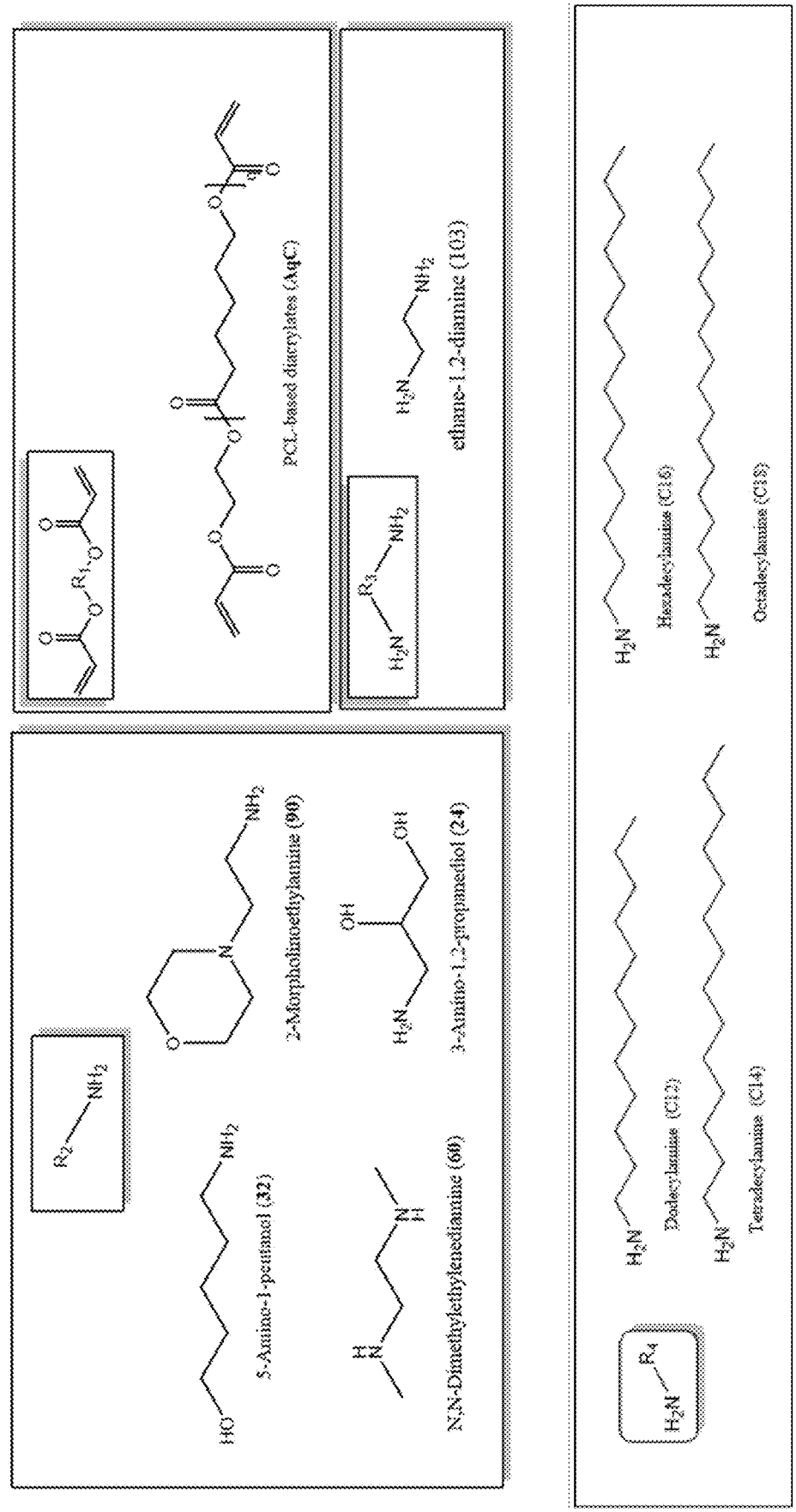
FIG. 7B depicts synthesis of Poly (β-amino ester) (PBAE) terpolymers.
Figure 7B:
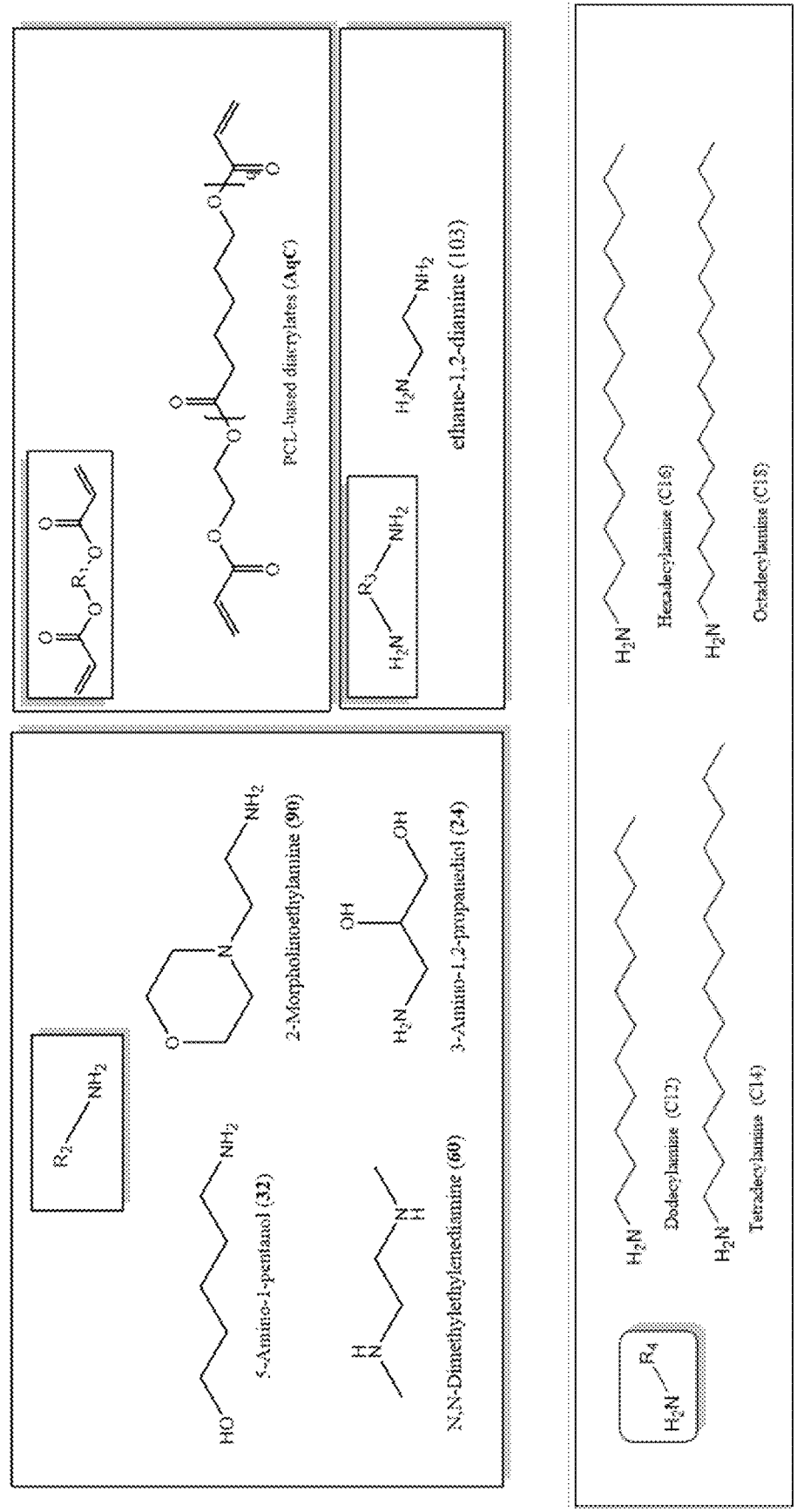

Linear PBAEs incorporating the custom diacrylate with q=3, 5, and 7 were synthesized in a two-step reaction. In the first step, as shown in FIG. 7B, an alkyl amine (dodecyl amine, C12) and different hydrophilic amines (32, 90, 60, 24) were reacted with the custom diacylate AqC at a ratio equal to 1.2:0.5:0.5 (diacrylate: hydrophilic amine:dodecyl amine) to produce a library of acrylate-terminated PBAE terpolymers. The second step is carried out without any intermediate purification and consists in another Michael addition with an excess of the diamine (103) in order to completely consume the remaining double bonds in the mixture. The linear PBAEs are named according to the following nomenclature: diacrylate/hydrophilic amine/lipophilic amine/end-capping amine. As an example, "A3C-60-C12-103" refers to the linear PBAE with a diacrylate with 3 caprolactone units (A3C), the hydrophilic amine 60, the lipophilic amine C12, and the end-capping diamine 103.

Figure 7C:
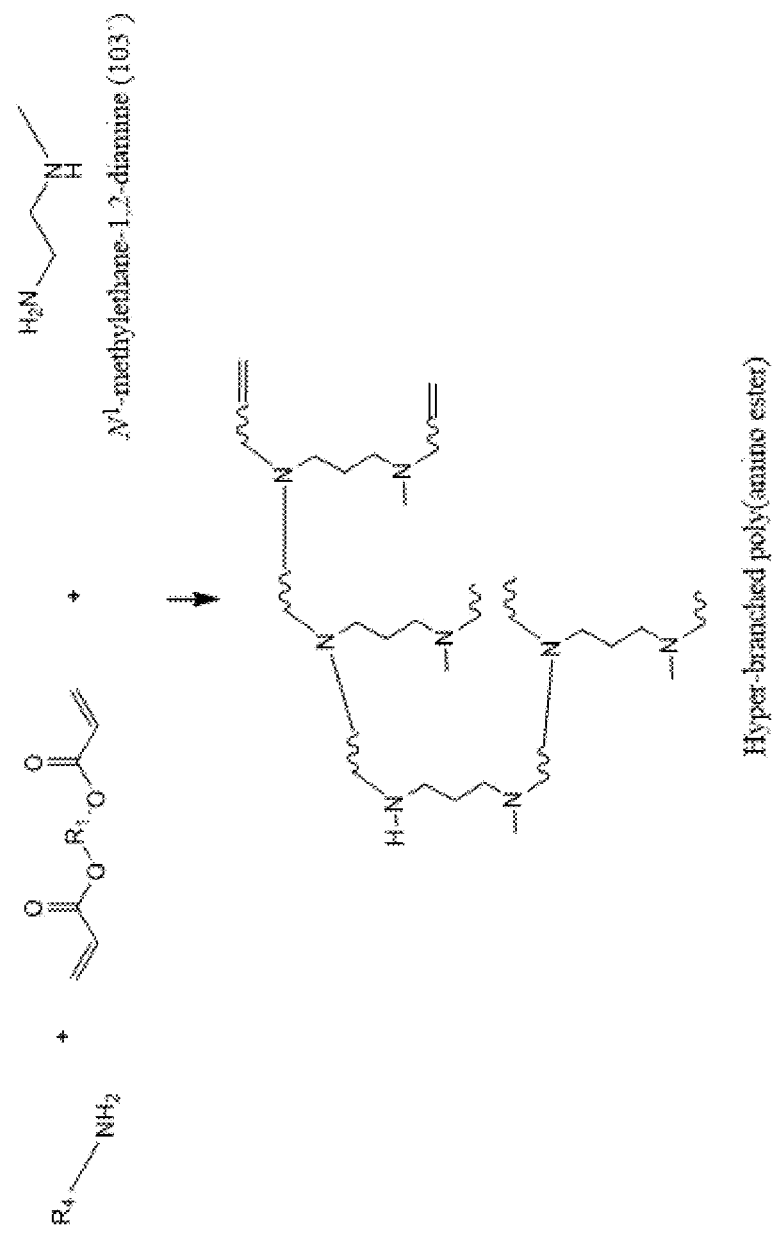
FIG. 7C depicts synthesis of hyperbranched PBAEs.

Hyperbranched PBAEs (FIG. 7C) incorporating the custom diacrylate with q=3 and 5 were synthesized in a three-step reaction. In the first step, different alkyl amines (C12-C18) were reacted with the custom diacrylates at a ratio equal to 1:2 (diacrylate:alkyl amine) for one day. Then N-Methyl-1,3-diaminopropane (103') was poured into the vial and the reaction was left to run for 48 hours in the same conditions. As a last step, 3-diaminopropane (103) was added in order to saturate the residual vinyl bonds available. The hyperbranched PBAEs are named according to the following nomenclature: diacrylate/trifunctional amine/lipophilic amine/end-capping amine. As an example, bA3C-103'-C12-103 is the linear PBAE with the diacrylate with 3 caprolactone units (A3C), the trifunctional amine 103', the lipophilic amine C12, and the end-capping 103.

Figure 8A:
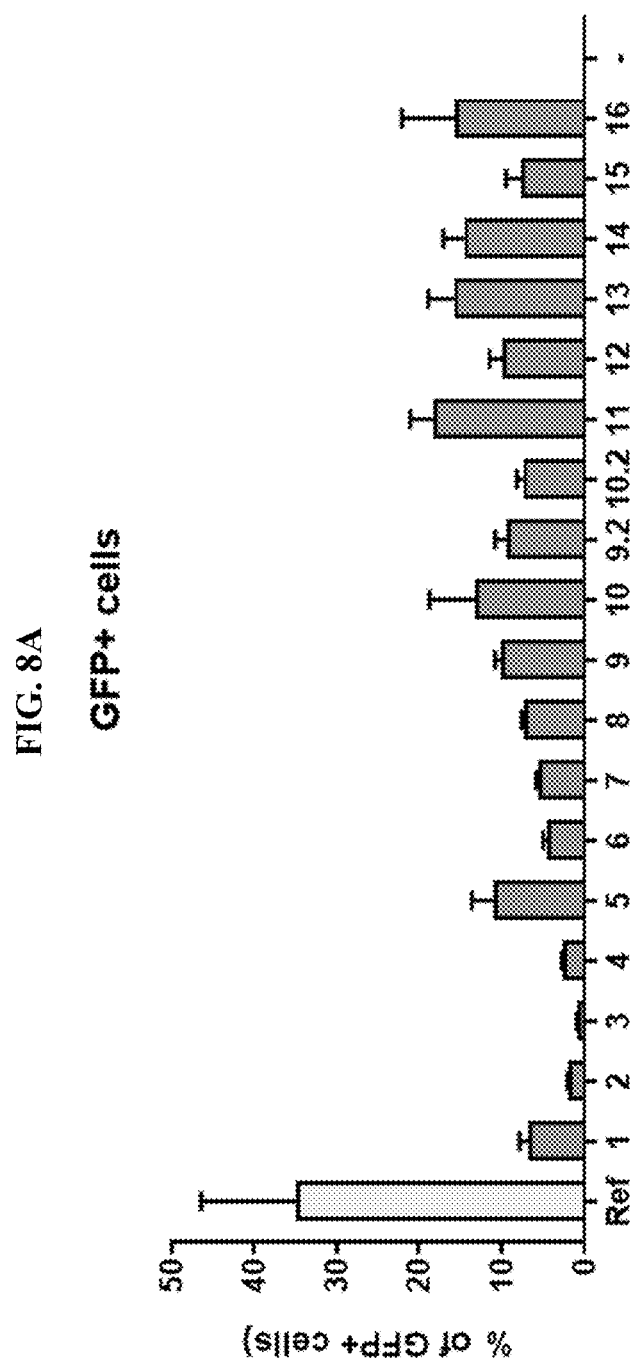
FIG. 8A is a graph depicting the DNA transfection efficiency of different PBAEs (1 to 16) loaded on the zwitterionic block copolymer MPC (expressed as a percentage of cells positive for the fluorescent reporter, in comparison with a reference commercial liposomic mixture "Ref"), assessed in BV2 microglia cell line by flow cytometry 48 hours after treatment.
Figure 8B:
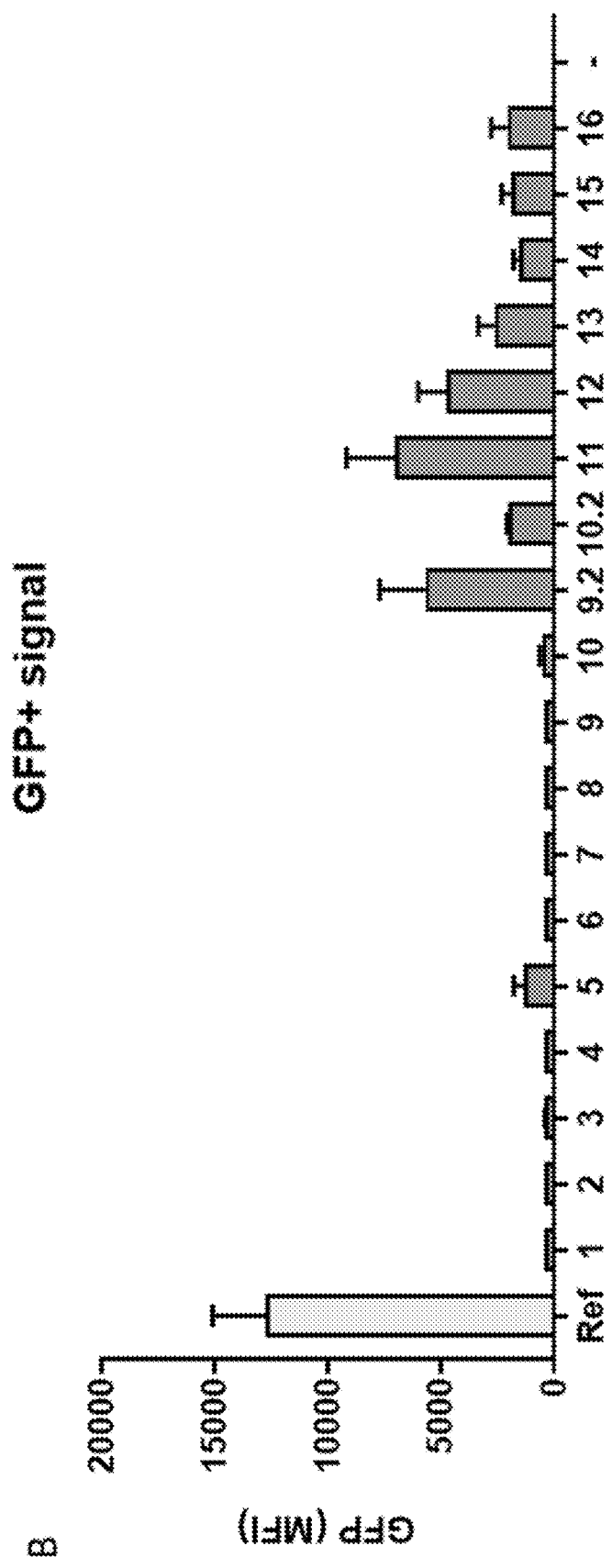
FIG. 8B is a graph depicting cellular DNA transfection efficiency of different PBAEs (1 to 16) loaded on the zwitterionic block copolymer MPC (expressed as intensity of the fluorescent reporter, corresponding to the extent of gene expression, in comparison with a reference commercial liposomic mixture "Ref"), assessed in BV2 microglia cell line by flow cytometry 48 hr after treatment.
Figure 8C:
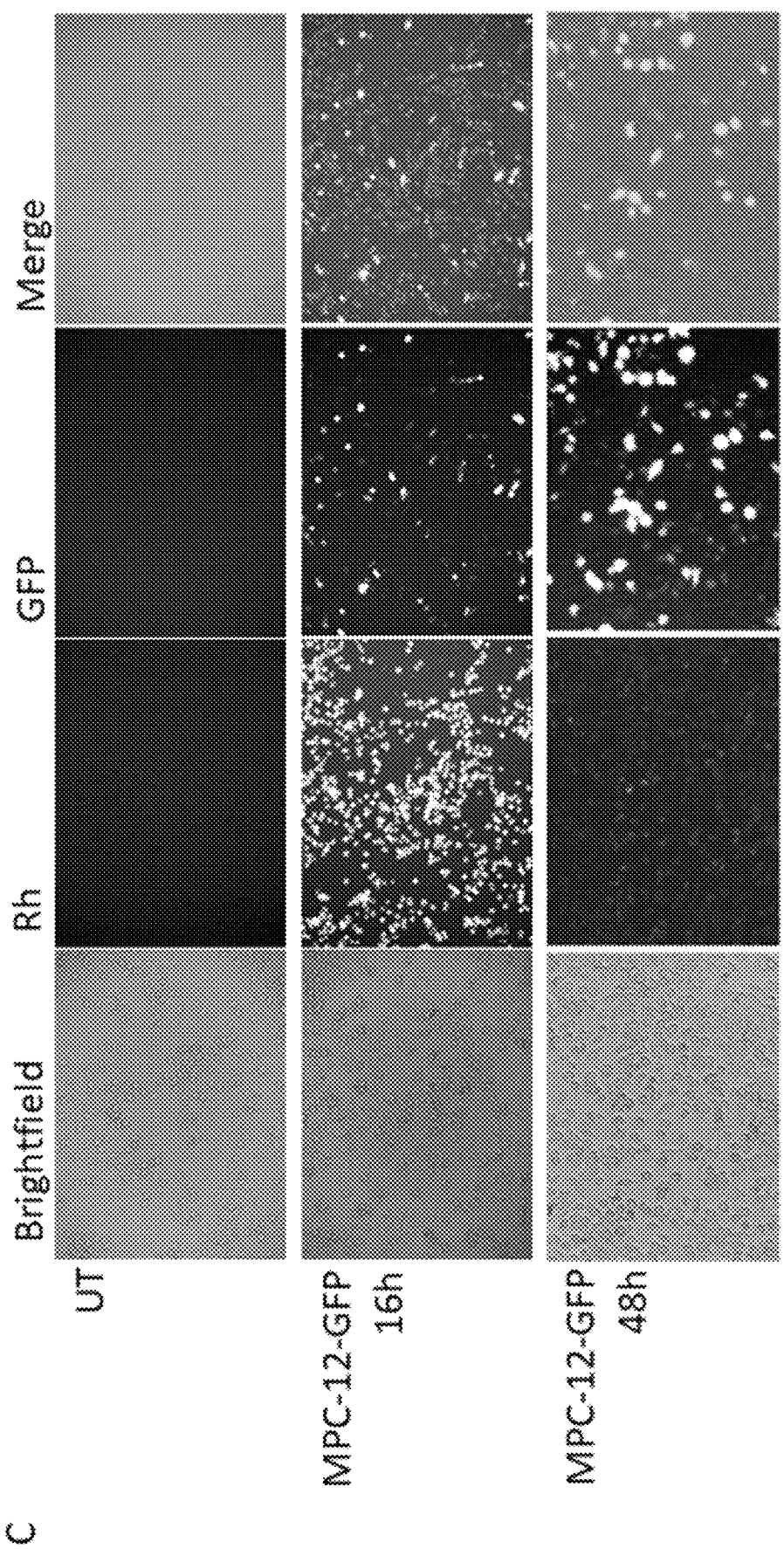
FIG. 8C depicts the distribution of GFP reporter gene in BV2 microglia cell line, assessed 16 hours and 48 hours post-transfection with PBAE polymer 12 complexed with a GFP-expressing plasmidic DNA and encapsulated in the zwitterionic block copolymer MPC. Brightfield shows the morphology of BV2 cells in the plate; Rh shows the rhodamine-positive signal, corresponding to the internalization of rhodaminated MPC NPs; GFP shows the signal of the reporter gene expressed by the plasmid upon internalization in the cells; Merge pictures show the merging of brightfield, Rh and GFP channels.

The polymer solution (PBAE in DMSO at 100 mg/ml) was directly dissolved in 25 mM NaOAc with the block-copolymer MPC (previously described) and mixed with GFP-expressing plasmid DNA to produce NPs. 18 different combinations and molar ratios of PBAE polymers were produced (Table 2). The NPs were then used to transfect BV2 cells, and the fluorescence was assessed by flow cytometry after 48 hours. Transfection of the same amount of plasmid DNA with a commercial liposomic mixture (Fugene, Promega) was used as reference ("Ref" in FIGS. 8A and 8B). As shown in FIG. 8A, GFP+ cells were detected with many of the 18 different formulations, with polymer #5, #10 and #11 through #16 displaying the best results in terms of transfection efficiency (measured as % of cells found positive for GFP), and with the polymers #11 through #16 displaying also the best performance when the extent of expression of the reporter gene was evaluated (FIG. 8B). These results indicate that these novel PBAEs can complex oligonucleotides (such as DNA) and that the complex can be loaded on the new polymeric MPC platform and used to form NPs able to transfer DNA into cells, as shown in FIG. 8C.

TABLE 2

| PBAE terpolymers | | |
|---|---|---|
| Sample | Name | Type |
| 1 | A3C-60-C12-103 | Linear |
| 2 | A3C-24-C12-103 | Linear |
| 3 | A3C-90-C12-103 | Linear |
| 4 | A3C-32-C12-103 | Linear |
| 5 | A5C-60-C12-103 | Linear |
| 6 | A5C-24-C12-103 | Linear |
| 7 | A5C-90-C12-103 | Linear |
| 8 | A5C-32-C12-103 | Linear |
| 9 | bA3C-103'-C12-103 | Branched |
| 10 | bA5C-103'-C12-103 | Branched |
| 9.2 | bA3C-103'-C12-103 | Branched |
| 10.2 | bA5C-103'-C12-103 | Branched |
| 11 | bA3C-103'-C14-103 | Branched |
| 12 | bA3C-103'-C16-103 | Branched |
| 13 | bA3C-103'-C18-103 | Branched |
| 14 | bA5C-103'-C14-103 | Branched |
| 15 | bA5C-103'-C16-103 | Branched |
| 16 | bA5C-103'-C18-103 | Branched |

Example 5. Loading Efficiency and Release Profile of Small Molecules Targeted to Modulation of Microglia Reactivity As described herein, loading and release of diapocynin, a small molecule targeted to inhibition of NADPH-oxidase 2 (NOX2) was demonstrated. NOX2 is a multi-subunit enzyme complex involved in redox stress and induction of pro-inflammatory cytokines, critically involved in the pathogenesis of several neurodegenerative diseases, including Parkinson's disease and ALS. Diapocynin, a covalent dimer of the NOX2-inhibitor apocynin, is the activated metabolite of apocynin produced by myeloperoxidase-mediated oxidation, also capable of inhibiting the expression of NOX2 mRNA and cytokines release. Without being bound by theory, administration of diapocynin removes the necessity for peroxidase involvement, which might limit diapocynin formation in vivo.

Diapocynin has a pKa of 7.4, so at physiological pH only half of the hydroxyl groups are protonated, thus causing an overall negative charge of the compound that enhances its solubility in water. For this reason, MPC-BCL3 NPs were used, composed of block copolymer complexed with a lipophilic cationic polymer (A3C32-C12-103, also called BCL3). Thus, the cationic polymer is expected to complex with diapocynin at physiological conditions to increase its loading efficiency.

Figure 15A:
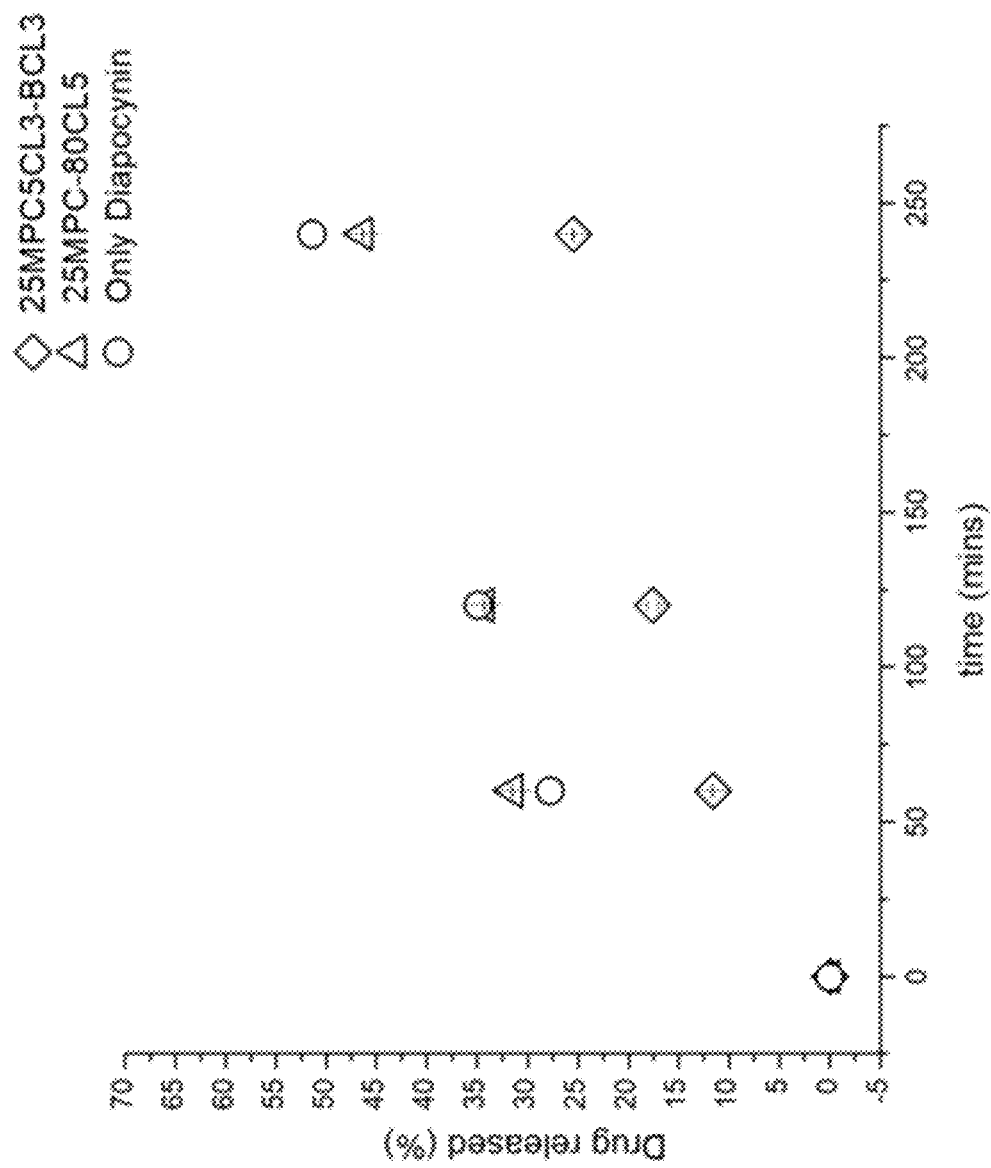
FIG. 15A is a graph depicting the relative release profile of 25MPC5CL3-BCL3 and 25MPC80CL5 NPs loaded with Diapocynin.

As shown in FIG. 15A, the loading efficiency, measured at t=0 and expressed as the amount of drug entrapped in the NP core compared to that loaded in the process, was 86.8%. Without being bound by theory, this indicates that the positively charged polymer allows a higher loading efficiency. Furthermore, the presence of the cationic polymer also slowed the kinetics of release of the drug compared with other NPs. In fact, after 4 hours only 25% of the drug had been released by 25MPC5CL3-BCL3 NPs compared with 50% release by the other NPs.

Figure 15C:
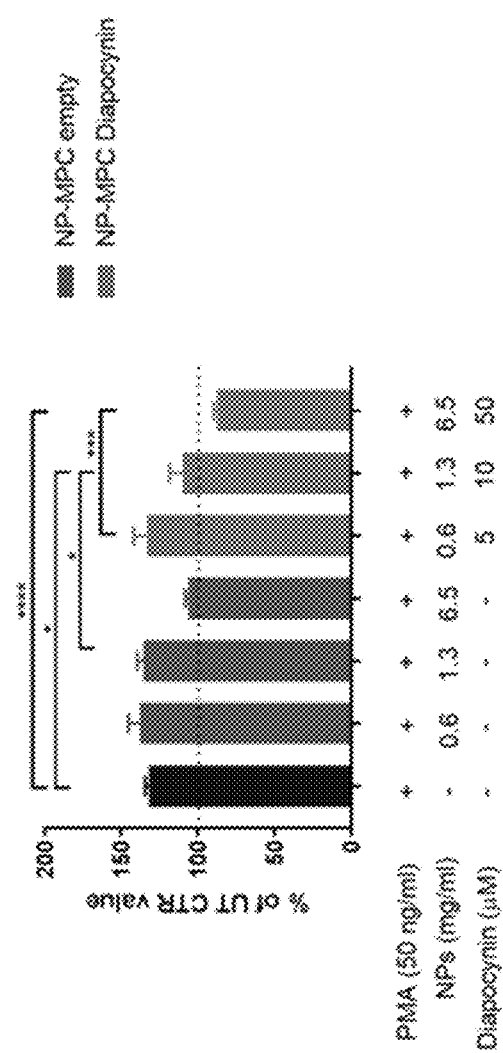
FIG. 15C depicts the inhibitory effects of dyapocinin encapsulated in MPC-NPs on PMA-induced ROS production in BV2 cells. *=$p<0.05$; *=$p<0.001$; **=$p<0.00001$; ANOVA followed by Tukey's post-hoc test.
Figure 15B:
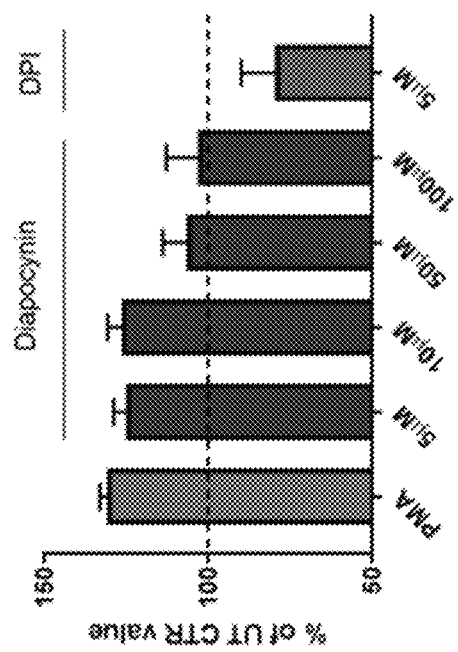
FIG. 15B depicts the inhibitory effect of dyapocinin on reactive oxygen species (ROS) production induced in BV2 cells by exposure to phorbol-ester myristate acetate (PMA). The effect of the exposure on diphenylene iodonium (DPI) is shown as reference compound.
Figure 16A:
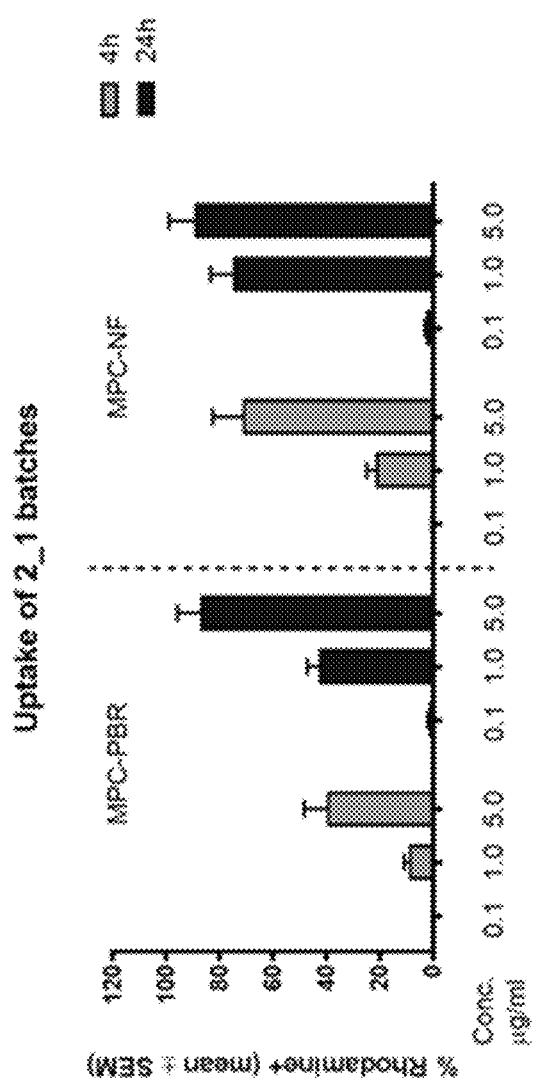
FIGS. 16A-16D depict flow cytometric evaluation of the uptake of NP-MPC functionalized with PBR-28 precursor (MPC-PBR) and non-functionalized (MPC-NF) after 4 hours or 24 hours of incubation in BV2 cells.
Figure 16B:
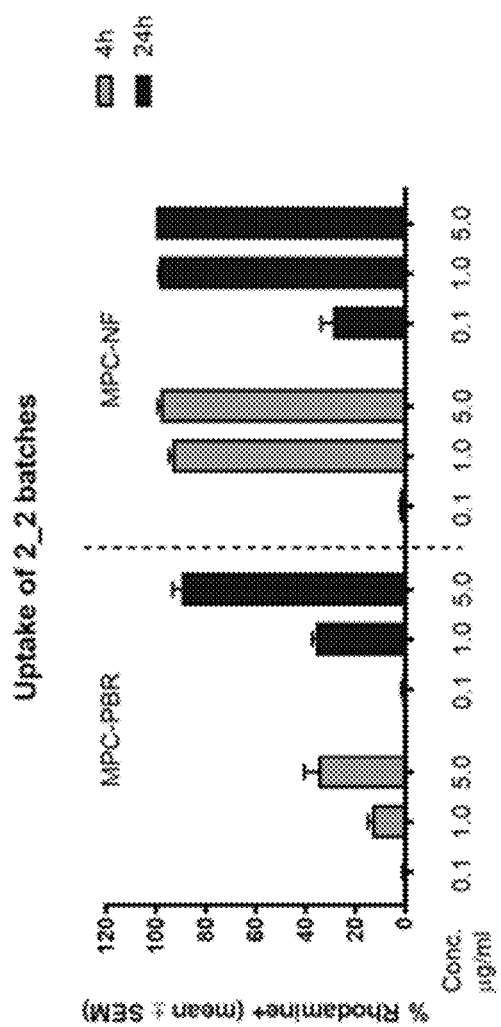
Figure 16C:
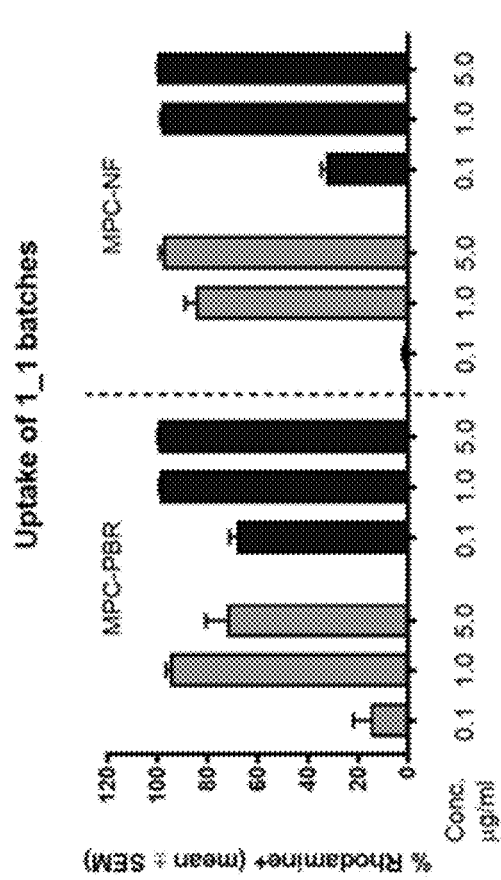
Figure 16D:
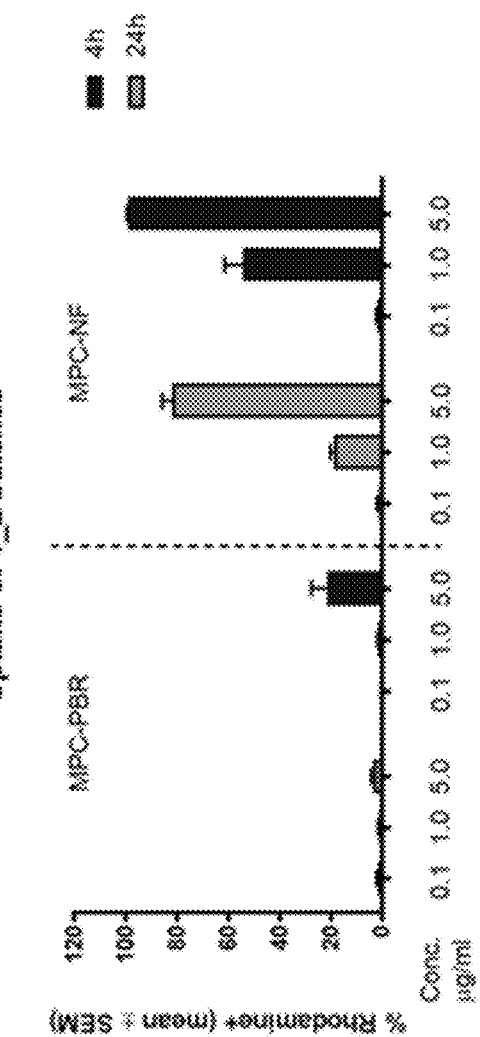
Figure 16F:
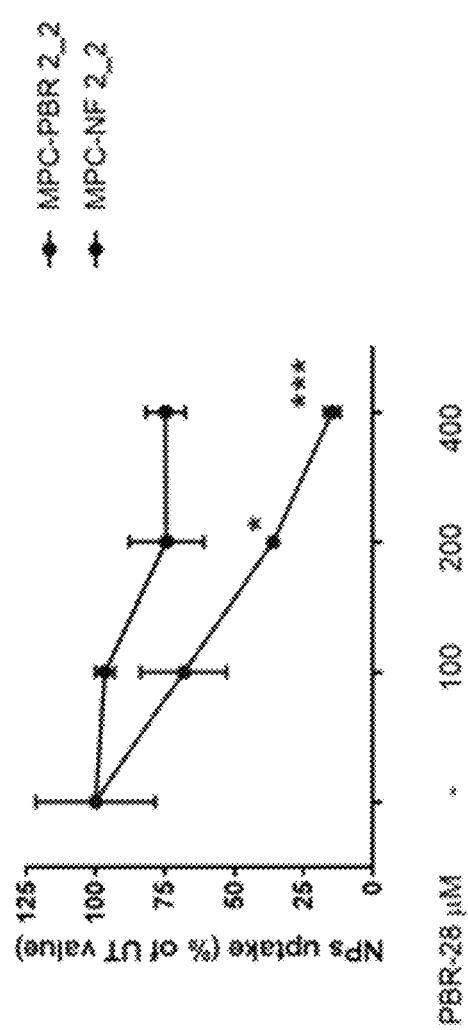
FIGS. 16E-16H depict a competition assay: flow cytometric evaluation of the uptake of MPC-PBR or MPC-NF in BV2 cells after incubation for 4 hours in the presence of increasing concentrations of the free ligand PBR-28.
Figure 16E:
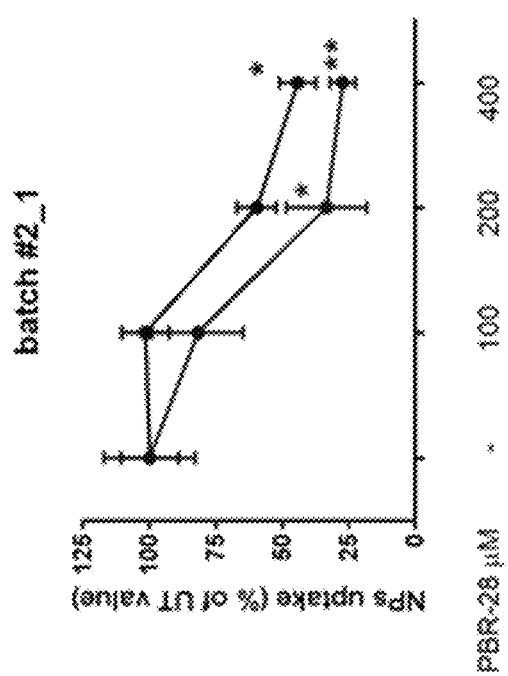
Figure 16H:
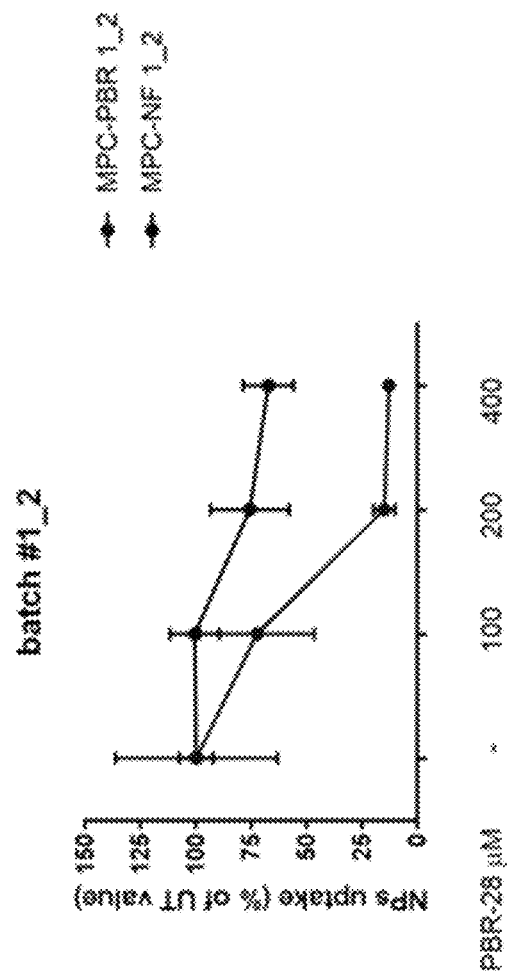
Figure 16G:
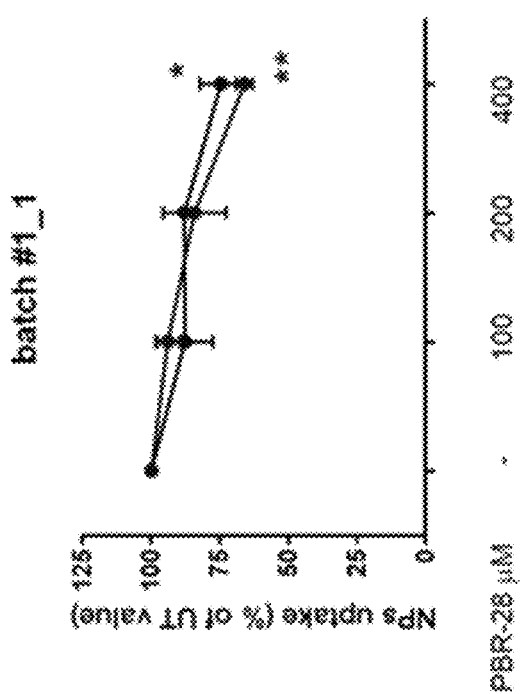

The WST-1 assay allows to measure the ROS produced by cell cultures. As shown in FIG. 15B, upon stimulation of BV2 microglia cell line with phorbol ester myristate acetate (PMA) 50 ng/ml for 6 hours, the WST-1 is capable of highlighting a 30-40% increase of ROS production as compared to untreated (UT) control. This effect is likely mediated by PMA-induced activation of NADPH-oxidase (NOX2), as co-incubation of cells with diphenylene iodonium (DPI), a well-known irreversible inhibitor of NOX2, is able to counteract the induction of ROS in the cultures. Diapocynin (added to the cell culture medium) is able to inhibit the PMA-induced increase of ROS at concentrations ≥50 μM. As shown in FIG. 15C, encapsulation of diapocynin in MPC-NPs does not interfere, but rather increases, the efficacy of the drug to inhibit PMA-induced ROS release, resulting efficacious already at a nominal concentration of 10 μM.

Example 6. Synthesis of Polymer Conjugates for Targeting the TSPO Receptor

Instrumental for proper surface functionalization of nanoparticles (NPs) is the identification of a precursor of the selected TSPO ligands that allows covalent attachment to the polymers without disrupting the binding properties of the original compounds.

Figure 18:
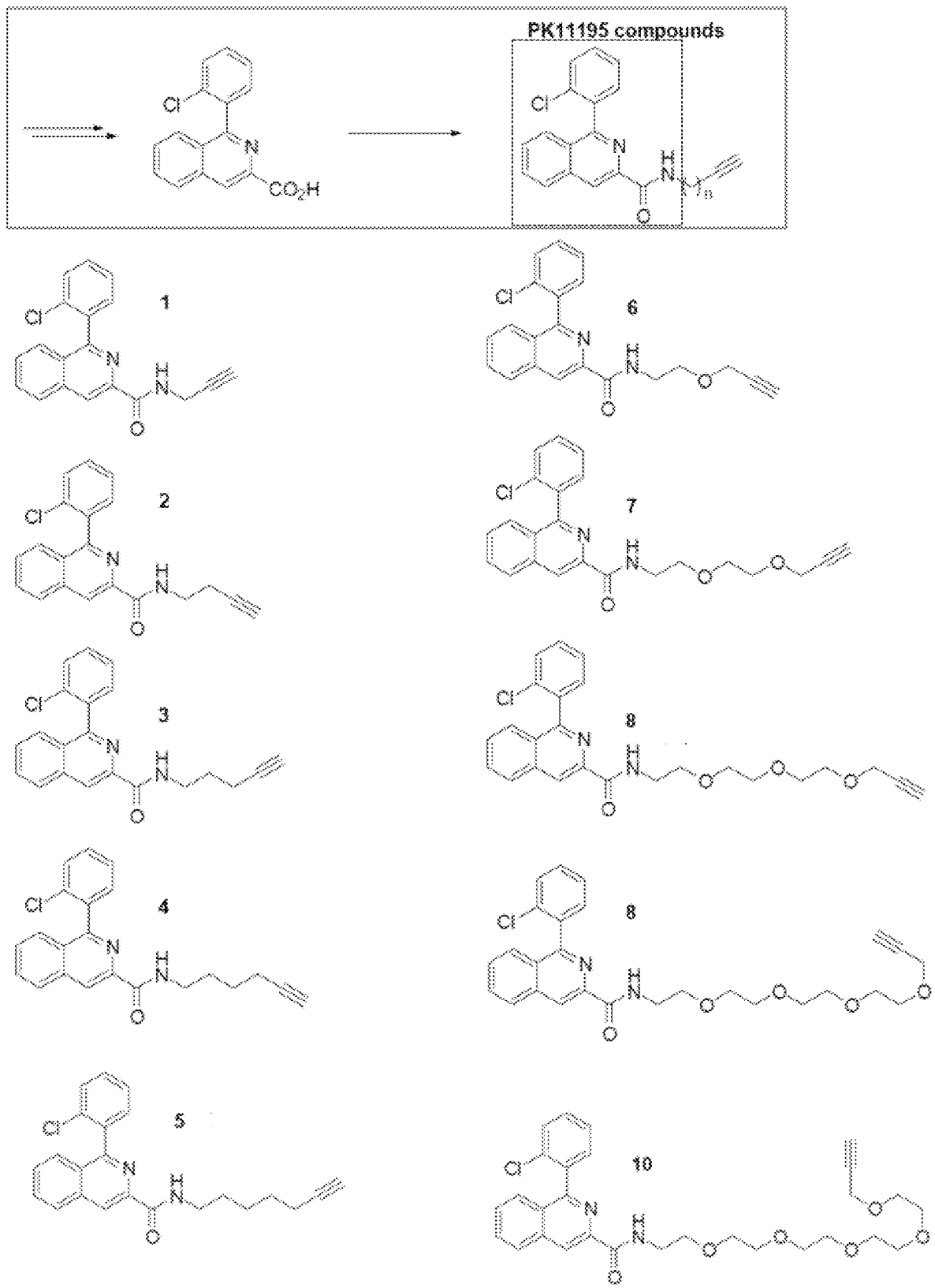
FIG. 18 depicts ten different PK11195 precursors, carrying an alkine group at variable distance from the site of interaction with the receptor, highlighted by the dashed box.
Figure 19:
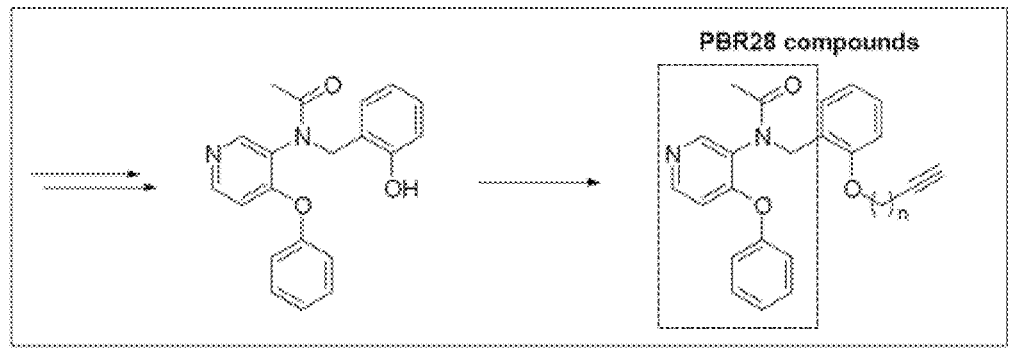
FIG. 19 depicts seven different PBR28 precursors, carrying an alkine group at variable distance from the site of interaction with the receptor, highlighted by the dashed box.
Figure 19:
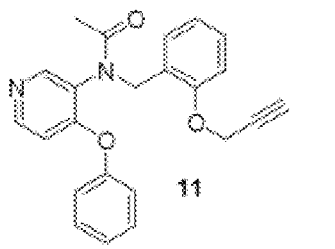
Figure 19:
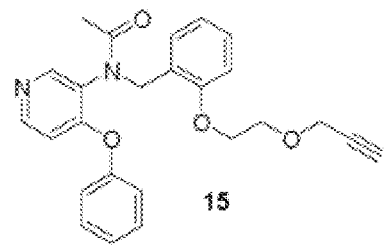
Figure 19:
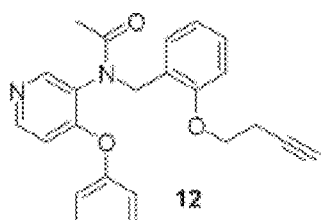
Figure 19:
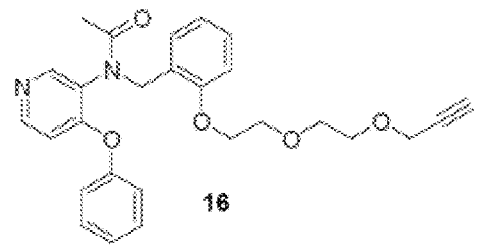
Figure 19:
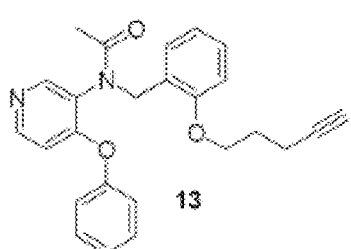
Figure 19:
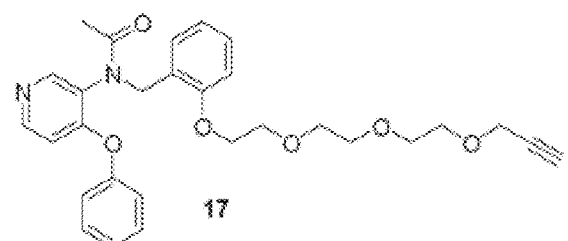
Figure 19:
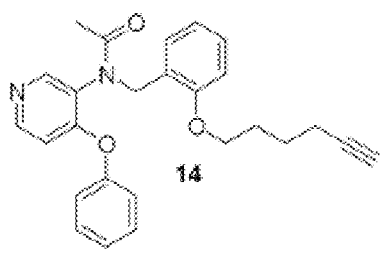

FIGS. 18 and 19 identify additional candidate TSPO-ligand precursors carrying an alkyne reactive group and suitable for NP functionalization through click-chemistry. Without being bound by theory, these compounds were designed based on the concept that the ligand should be a certain distance between the NP surface (where the conjugation of the NP with the ligand takes place) and the site of ligand-receptor interaction, to prevent possible steric hindrance affecting the binding to the receptor.

Figure 9A:
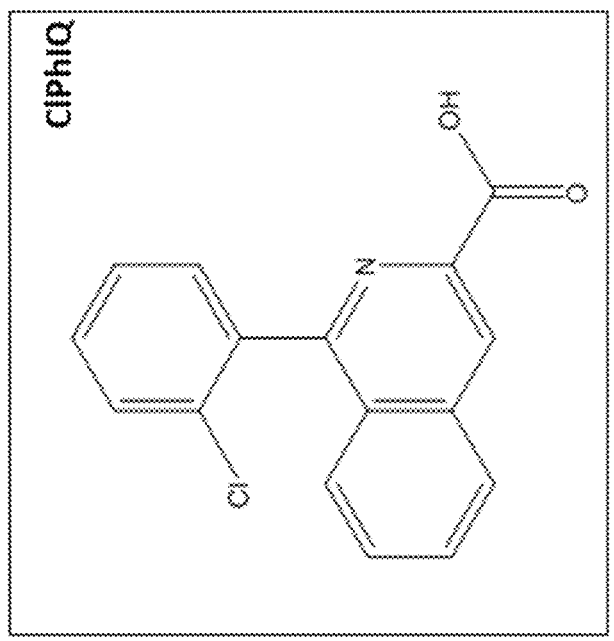
FIG. 9A depicts the molecular formula of the TSPO ligand PK11195 and its precursor 1-(2-chlorophenyl)isoquinoline-3-carboxylic acid (ClPhIQ).
Figure 9A:
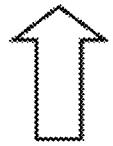
Figure 9A:
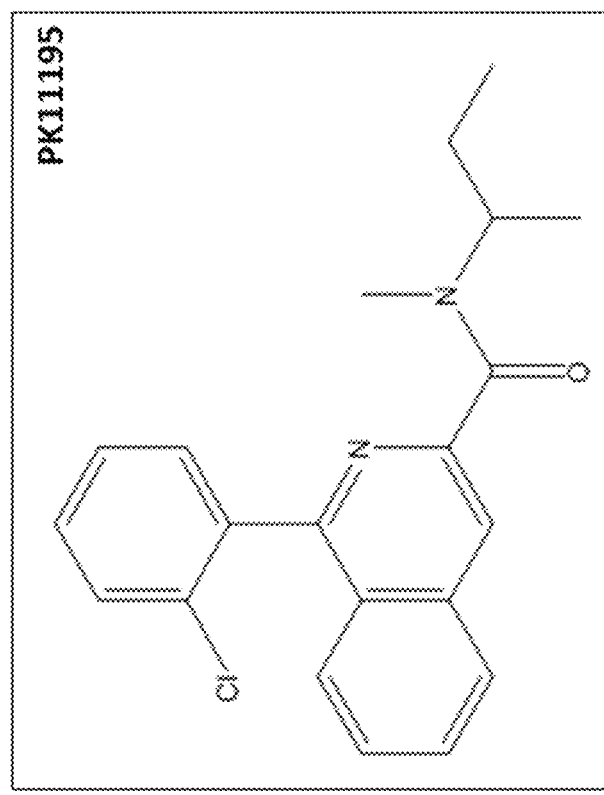
Figure 9B:
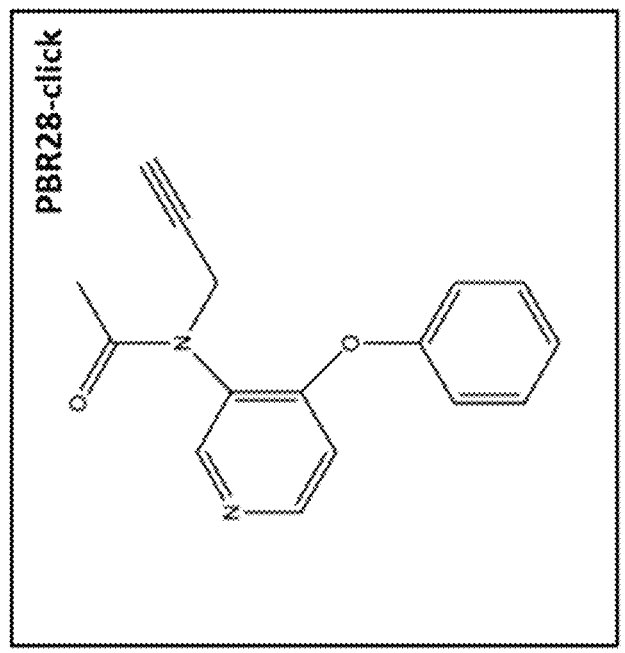
FIG. 9B depicts the molecular formula of the TSPO ligand PBR28 and the precursor (PBR28-click reactant).
Figure 9B:
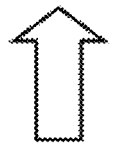
Figure 9B:
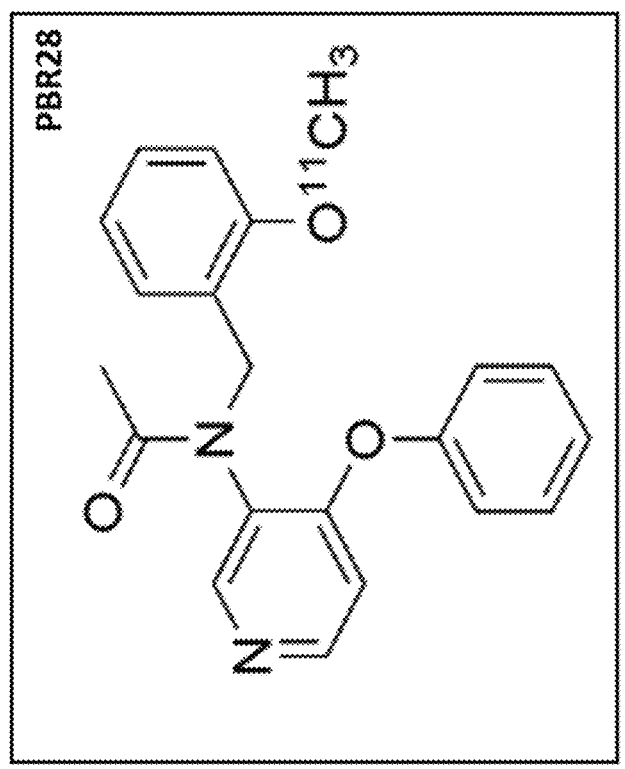

As described hereinbelow, results were obtained with two TSPO-ligand precursors as proof of concept: i) 1-(2-chlorophenyl)isoquinoline-3-carboxylic acid (ClPhIQ), a commercially available PK11195 precursor; and ii) the PBR28 precursor PBR-click (synthesized ex novo) (FIGS. 9A, 9B).

Example 7. Synthesis and Characterization of Polymer-PK11195 Conjugates

Figure 10B:
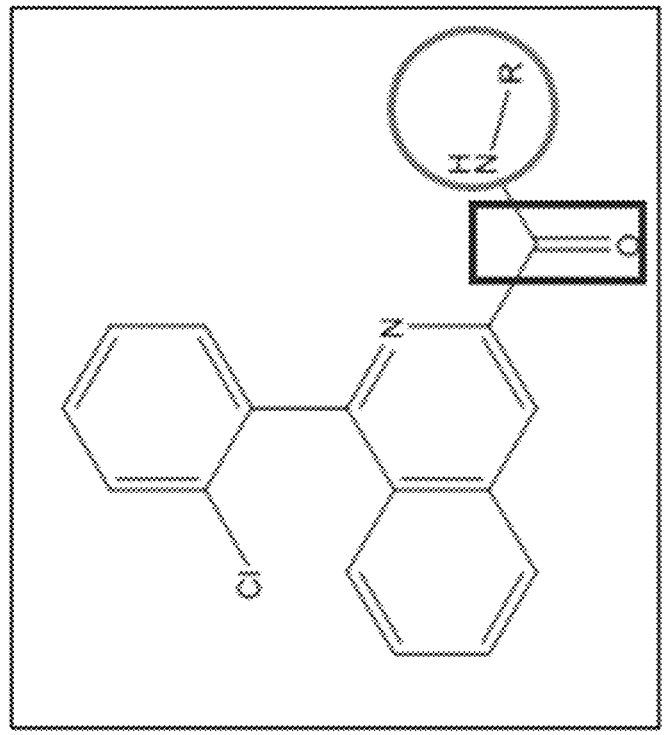
FIG. 10B is a schematic structure of the final polymer, carrying both TSPO-selective ligands and fluorescent dyes. The molar ratios of ligand/dye and the length of the side chains (arrow) can be modified, allowing the ability to explore different nanomaterial configurations.
Figure 10A:
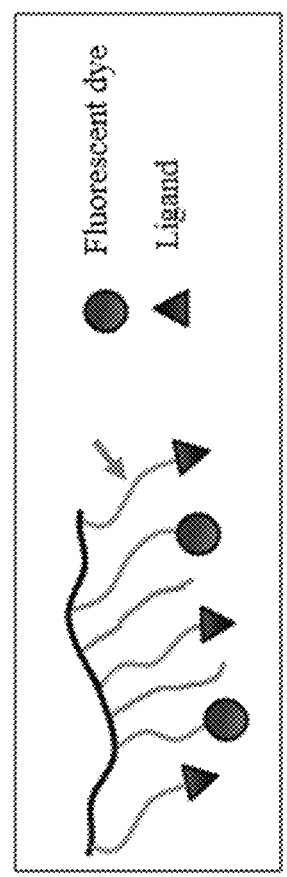
FIG. 10A depicts 1-(2-chlorophenyl)isoquinoline-3-carboxylic acid bound with primary amine. The circle highlights the bond with one of the primary amines present on the terminal branches of the nanoparticles. The box highlights the carbonyl group, present also in the formula of PK11195, which is involved in important interactions with the TSPO receptor binding pocket.

Polyethylene glycol (PEG) was utilized as the starting monomer for the synthesis of desired final branched polymers. PEG's hydrophilicity was exploited to enhance the water solubility of ligands. PEGMA-$NH_2$ terminated, a monomer based on PEG and having a free and accessible reactive group (—$NH_2$) at one end of the PEGMA, was produced via RAFT (Reversible addition—fragmentation chain-transfer) polymerization in order to obtain a high molecular weight branched polymer with terminal reactive amino-groups. Starting from the PK11195 precursor ClPhIQ, a 1-(2-chlorophenyl)isoquinoline-3-carboxylic acid derivative was generated that is bound to one of the primary amines of the synthesized polymers (FIG. 10A). This bond produces a carbonyl group (FIG. 10A) super-imposable to the carbonyl group present in the original PK11195 and known to be involved in long-range electrostatic interactions with translocator protein (TSPO) receptor.

One peculiar feature of the synthetized functionalized polymers is that they have a comb-like structure, suitable for binding at the same time the targeting moiety (1-(2-chlorophenyl)isoquinoline-3-carboxylic acid, working as a TSPO-ligand) and other tracer compounds, such as fluorescent-labeled chains (FITC or rhodamine), or radioligands for PET imaging. This allows the tracking of the compounds by fluorescent microscopy/flow cytometry or spectrofluorimetry. By controlling the stoichiometry of the reactions performed to attach the ligands or fluorescent dyes to the comb-like polymer, it is possible to obtain different nanoparticles carrying variable molar ratios of ligand/dye. FIG. 10B shows a schematic representation of the final comb-like polymer; the H-NMR characterization of the functionalized polymer is shown at FIG. 10C.

Figure 10C:
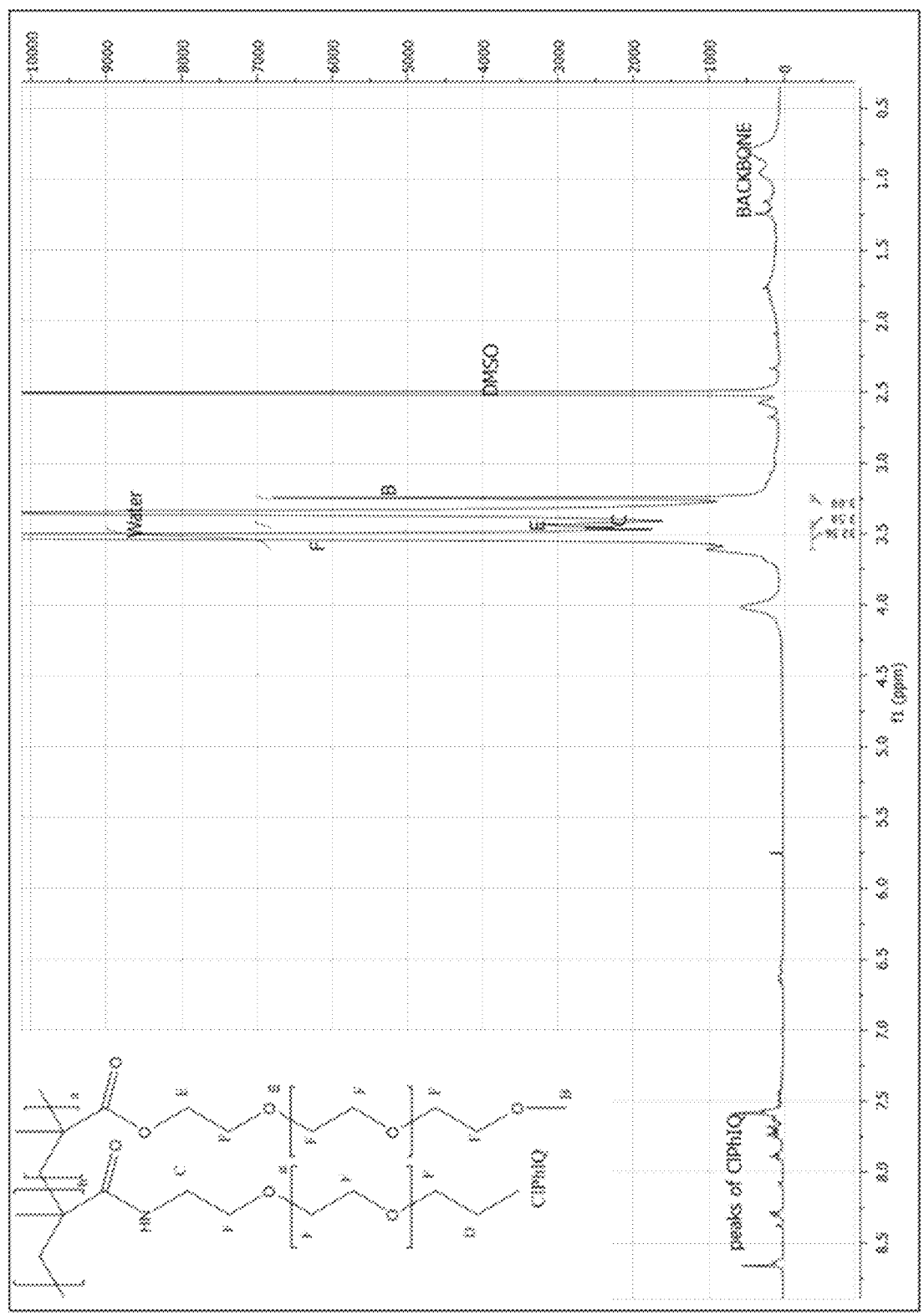
FIG. 10C depicts H-NMR analysis of a ClPhIQ-polymer conjugate used to confirm the loading of ClPhIQ on the comb-like nanoparticles.
Figure 11A:
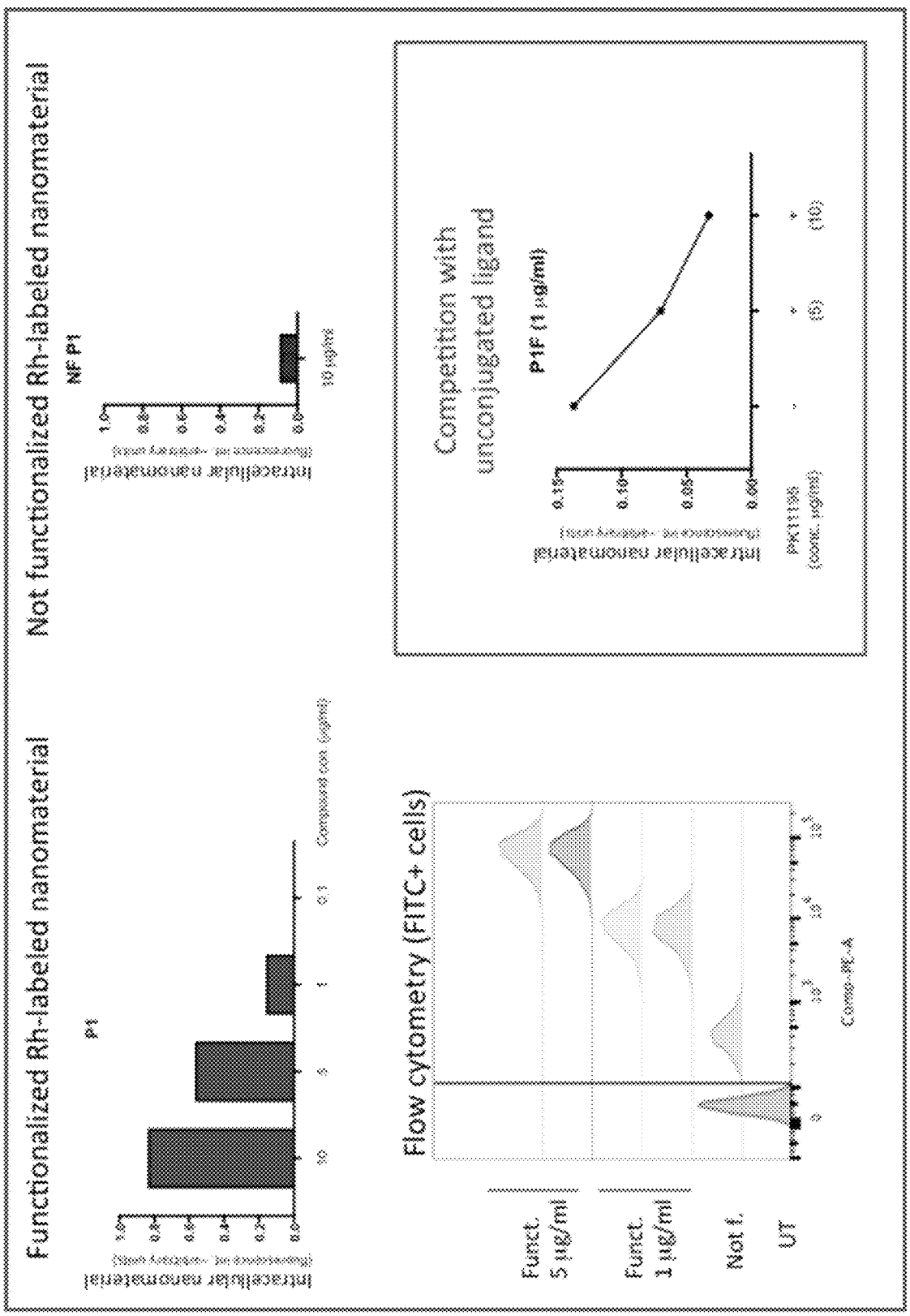
FIG. 11A depicts assays to test the uptake of the PK11195 functionalized polymers P1F and the corresponding non-functionalized counterpart NF-P1 in BV2 microglia cell line.
Figure 11B:
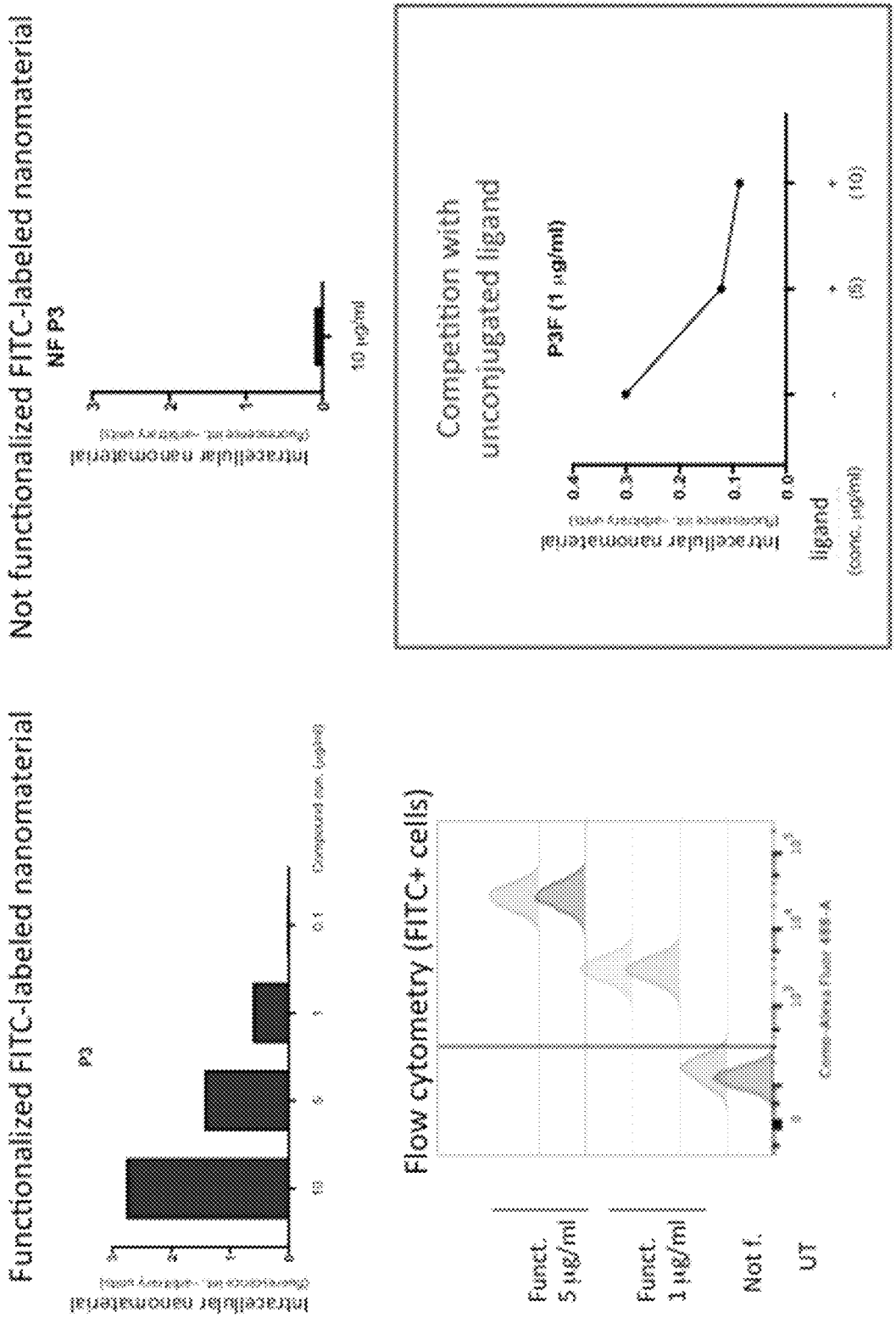
FIG. 11B depicts assays to test the uptake of the PK11195 functionalized polymers P3F and the corresponding non-functionalized counterpart NF-P3 in BV2 microglia cell line.
Figure 11C:
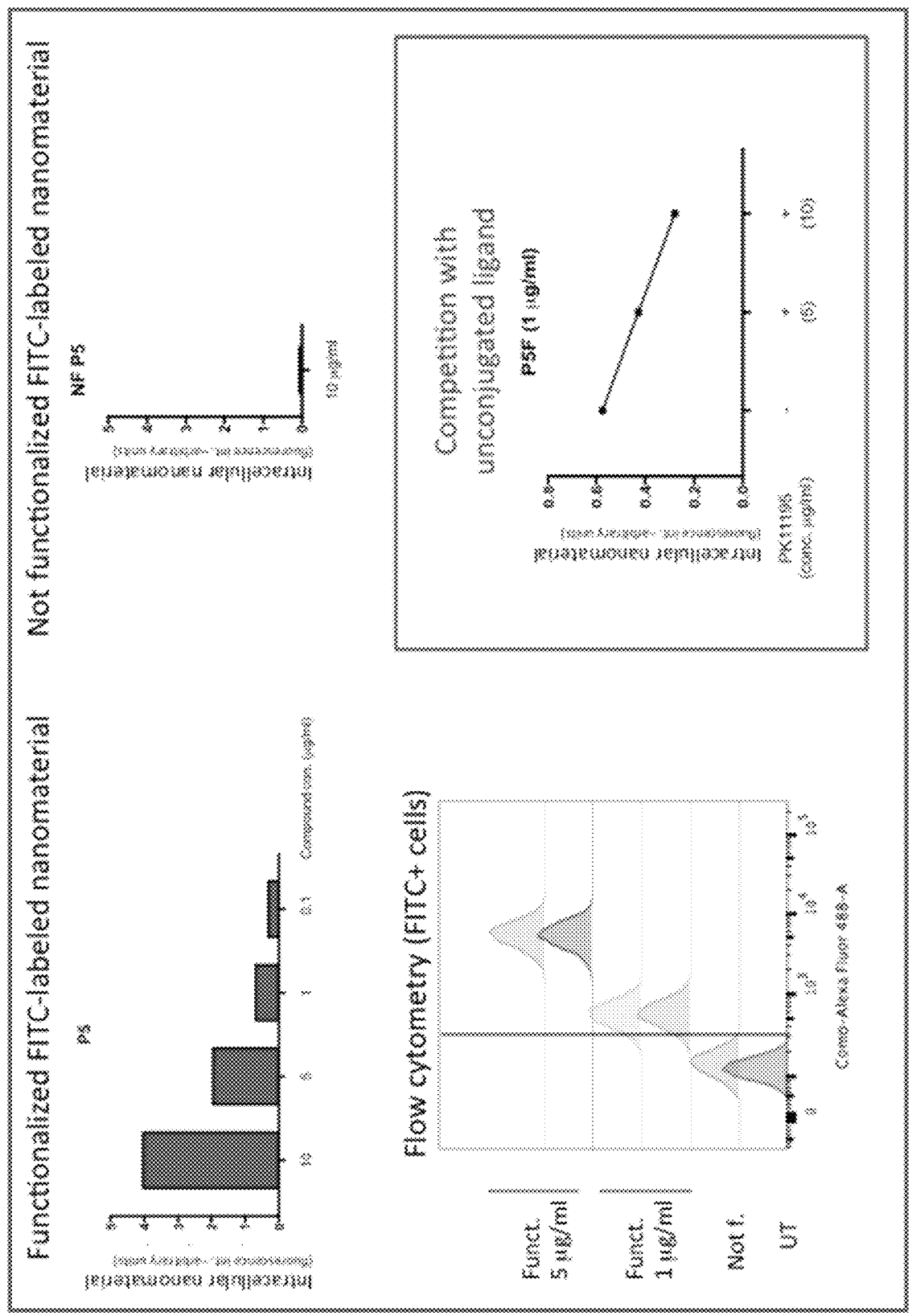
FIG. 11C depicts assays to test the uptake of the PK11195 functionalized polymers P5F and the corresponding non-functionalized counterpart NF-P5 in BV2 microglia cell line.
Figure 11D:
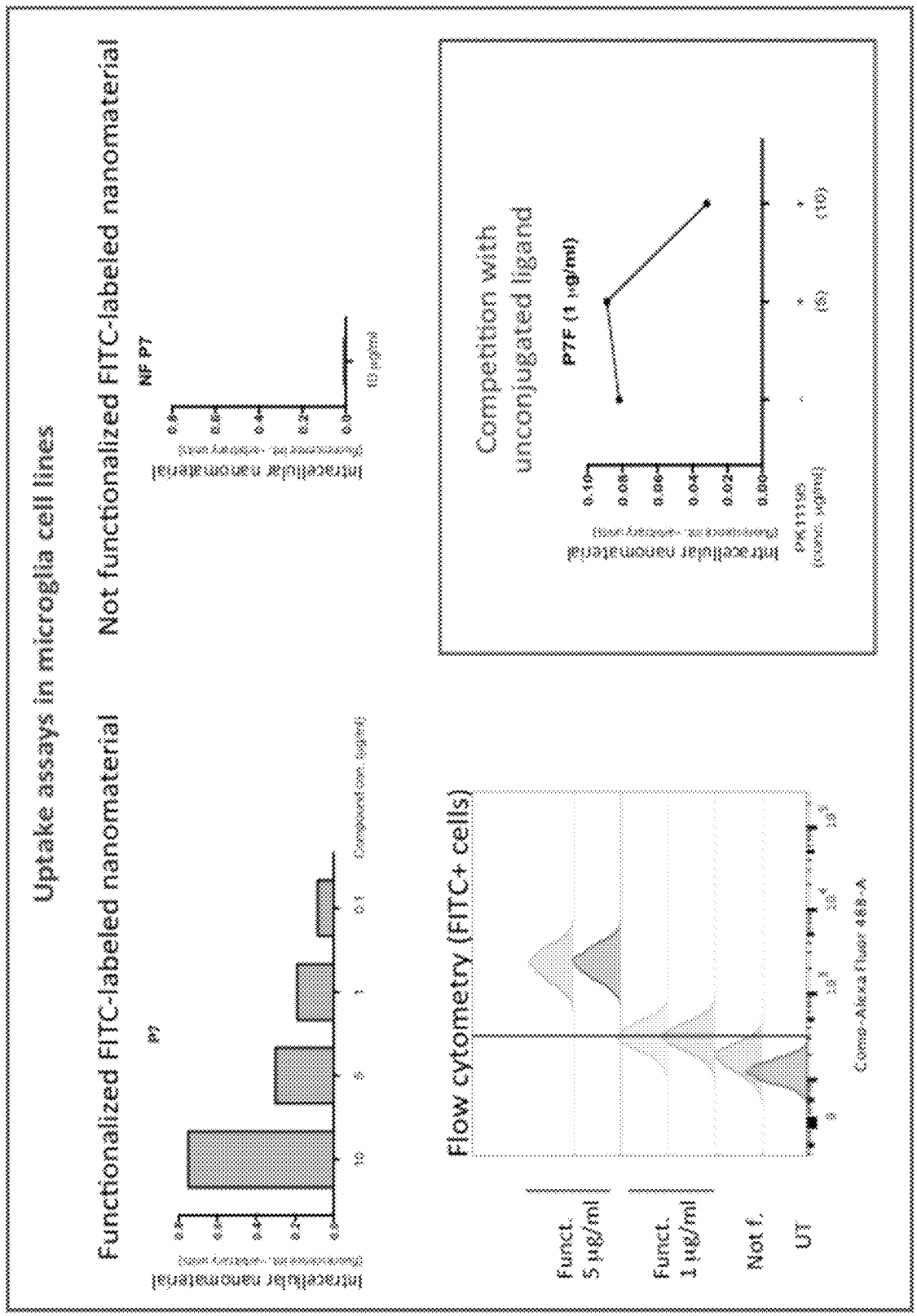
FIG. 11D depicts assays to test the uptake of the PK11195 functionalized polymers P7F and the corresponding non-functionalized counterpart NF-P7 in BV2 microglia cell line. For FIGS. 11A to 11D, the top graphs illustrate the presence of functionalized and nonfunctionalized labeled nanoparticles (P1, P3, P5, and P7) with cells to which the NPs were administered as measured by fluorescence. The bottom left graph shows flow cytometry results for cells treated with different concentrations of functionalized nanoparticles, non-functionalized nanoparticles, and untreated cells. The bottom right panel is a graph depicting the results from competition assays between the functionalized polymer and unconjugated ligand.

As shown in FIG. 10C, the ring hydrogens of ClPhIQ give resonance signals in the range of 7.5-8.67 ppm. These signals are also visible after dialysis purification. These results confirm that the targeting agent is properly bound with the polymer through an amide covalent bond.

The molecular weight of the polymer can be varied by changing the molar ratio between the monomers adopted and the RAFT agent. The length of the PEG side chains can be modified as well as the molar ratio of ligand and the polymer. Without being bound by theory, all these parameters can potentially influence the binding of the polymer-TSPO ligand conjugate. For this reason, materials with different features were produced (see Table 3). Ligand-dependent uptake was tested by different assays on BV2 microglia cell line, to identify the formulation allowing best selectivity of uptake.

TABLE 3

Chemical characteristics of produced polymers and results of in vitro assays performed to validate the selectivity of uptake.

| Sample ID | Functionalization with TSPO ligand | Fluorescent tag | Mw polymer (theoretical) | Mw polymer (GPC) | PDI (GPC) | Mw PEG side chain |
|---|---|---|---|---|---|---|
| P1 NF | NO | RhB (0.15% w/w) | 13 kDa | 15.3 kDa | 1.56 | 600 Da |
| P3 NF | NO | FITC (7.6% w/w) | 25 kDa | 19.7 kDa | 1.53 | 600 Da |
| P5 NF | NO | FITC (6.1% w/w) | 13 kDa | 14.2 kDa | 1.62 | 600 Da |
| P7 NF | NO | FITC (6.1% w/w) | 13 kDa | 16.1 kDa | 1.66 | 300 Da |
| P1 F | ClPhIQ (10.8% w/w) | RhB (0.15% w/w) | 13 kDa | 16.2 kDa | 1.71 | 600 Da |

TABLE 3-continued

Chemical characteristics of produced polymers and results of in vitro assays performed to validate the selectivity of uptake.

| | | | | | | |
|---|---|---|---|---|---|---|
| P3 F | ClPhlQ (4.5% w/w) | FITC (7.6% w/w) | 25 kDa | 21.1 kDa | 1.65 | 600 Da |
| P5 F | ClPhlQ (8.6% w/w) | FITC (14.1% w/w) | 13 kDa | 16.2 kDa | 1.69 | 600 Da |
| P7 F | ClPhlQ (10.4% w/w) | FITC (6.1% w/w) | 13 kDa | 18.9 kDa | 1.73 | 300 Da |

Assays on BV2 microglia cell line

| Sample ID | Uptake | Competition with the uptake of free ligand (PK11195) | Uptake is responsive to LPS pre-stimulation |
|---|---|---|---|
| P1 NF | NO (up to the concentration of 10 µg/ml, which is the maximal concentration tested for the corresponding functionalized polymers) | Not tested | NO |
| P3 NF | | | |
| P5 NF | | | |
| P7 NF | | | |
| P1 F | Yes | Yes | NO |
| P3 F | Yes | Yes | Yes |
| P5 F | Yes | Yes | Yes |
| P7 F | Yes | Yes | NO |

("Mw" denotes molecular weight; "GPC" denotes gel permeation chromatography, and "PDI" denotes polydispersity index.)

Figure 12B:
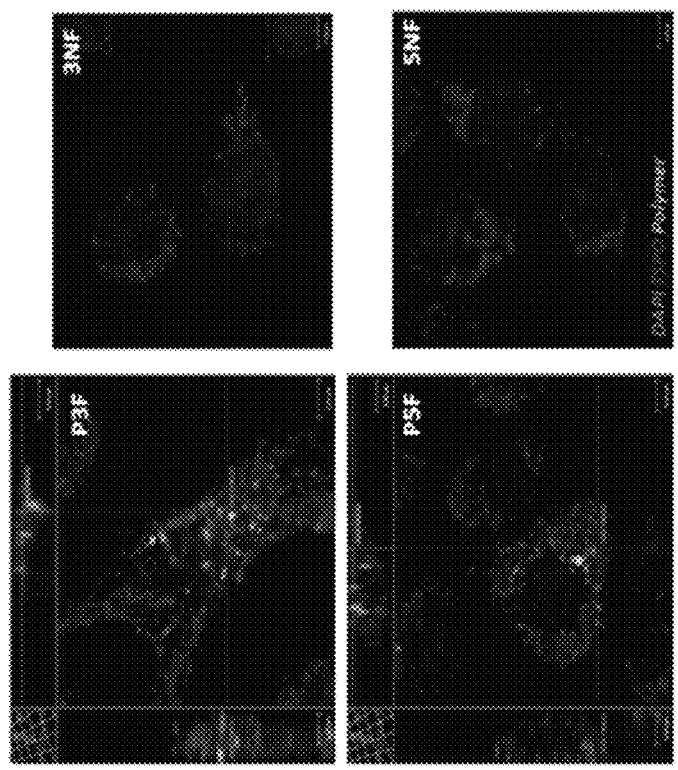
FIG. 12B depicts representative laser scanning confocal microphotographs of FITC$^+$ functionalized (P3F, P5F) and the corresponding non-functionalized (3NF, 5NF) polymers (gray), TSPO (light gray) and DAPI nuclear staining (dark gray) in BV2 cells. No FITC$^+$ signal was detected in the cells exposed to the non-functionalized polymers, whereas BV2 cells treated with P3F or P5F display prominent FITC$^+$ punctate signal in the cytoplasm, which was partially co-localized with TSPO staining.
Figure 12A:
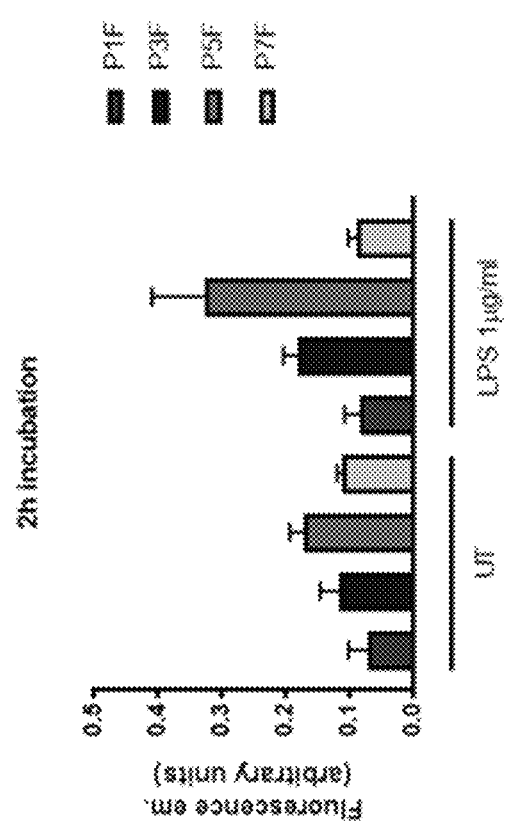
FIG. 12A is a graph showing uptake of the functionalized polymers P1F, P3F, P5F, and P7F in BV2 cell line exposed to LPS stimulation (1 µg/ml).

Compounds P1F, P3F, P5F, and P7F were added at different concentrations (in the range of 0.1-10 µg/ml) to the cell culture medium for 24 hours. Cells were collected and analyzed by spectrofluorimetry and flow cytometry to verify the uptake of the fluorescent labeled nanoparticles. Specificity of uptake was verified by: i) comparison with cells incubated with the respective fluorescent labeled non-functionalized polymers (namely P1-NF, P2-NF, P3-NF, and P4-NF, tested at 10 µg/ml); and ii) establishing a competitive pharmacological assay by co-incubating the functionalized polymers (tested at 1 µg/ml) with high concentrations (5 or 10 µg/ml) of the free unconjugated TSPO ligand PK11195 for 24 hours. As shown in FIGS. 11A-11D and summarized in Table 3, all of the four functionalized polymers displayed a good pharmacological profile. In terms of efficiency of the uptake, the level of uptake increased proportionally with the polymer concentration. Moreover, the uptake of the functionalized polymers was selective, as co-incubation of the conjugated polymers with increasing concentrations of the free ligand was able to disrupt the uptake, with P1F, P5F and P7F displaying the best profiles. Further testing in BV2 cells stimulated by lipopolysaccharide (LPS), to upregulate TSPO expression, confirmed that polymers P3F and P5F displayed the most promising uptake profile (FIG. 12A and Table 3). Without being bound by theory, their uptake appeared to be modulated by the level of engagement of the TSPO receptor. As shown in FIG. 12B, laser scanning confocal microscopy highlighted the presence of the FITC-labeled functionalized polymers (i.e., P3F or P5F) within the cytoplasm of BV2 cells and not the non-functionalized ones (P3-NF and P5-NF). The FITC$^+$ signal was punctate and only partially co-localized with TSPO staining. Without being bound by theory, this indicates the accumulation of polymers in vesicle-like structures in close proximity to TSPO$^+$ compartment. As shown in FIG. 12C, cells treated with different concentrations of PCL-PK11195 were distinct from cells treated with drug alone or untreated, and represented decreasing percentage of a parent population of cells with increasing PCL-PK11195 dosage.

Figure 13A:
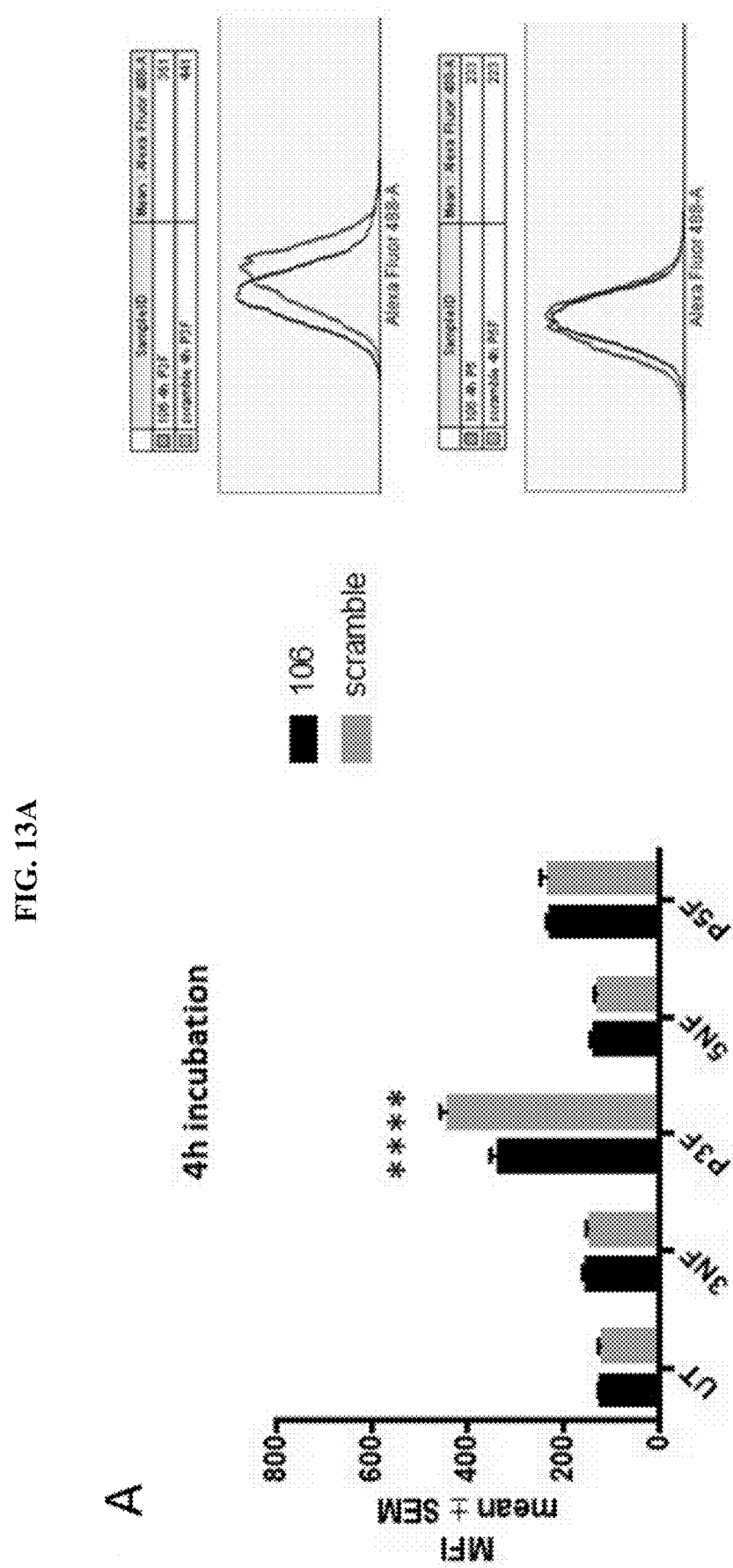
FIGS. 13A-13B depict flow cytometric evaluation of the uptake of polymers P3 and P5 (functionalized and non-functionalized) on BV2 cells lines expressing physiological levels (#scramble cell line) or about 20% of normal levels (#106 cell line) of TSPO.
Figure 13B:
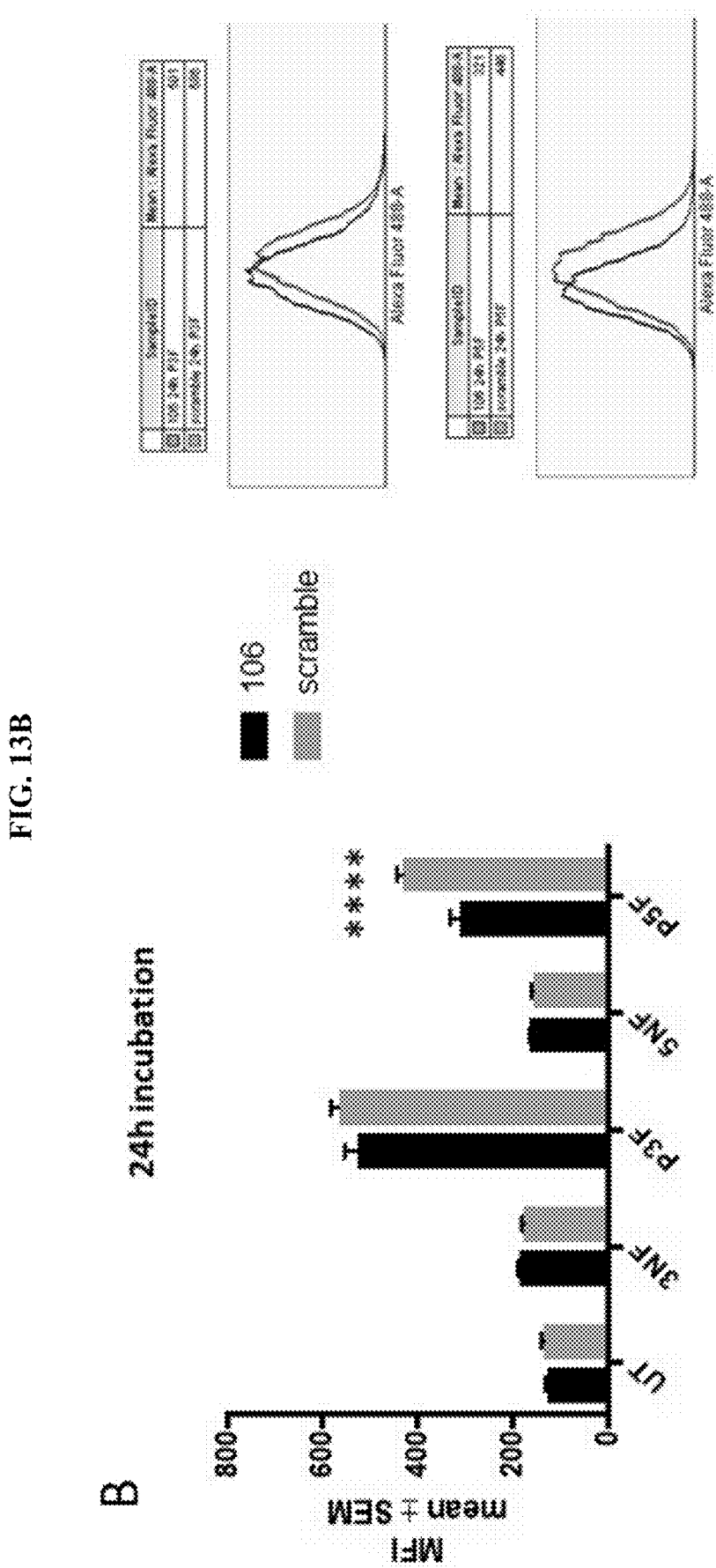

To further validate P3F and P5F in terms of selectivity for TSPO, their uptake was tested in the BV2 #106 cell line, which expresses only 20% of normal levels of TSPO due to infection with a lentiviral vector expressing a shRNA targeted to murine TSPO. BV2 #scramble (derived from infection with a lentiviral vector expressing a scrambled shRNA) was used as control. Briefly, 30,000 cells/well were plated in 48 wells plates one day before the experiment. Then, conjugated polymers P3F and P5F (1 µg/ml) were added to the cell culture medium. At 4 hours or 24 hours after treatment, the medium was aspirated, and cells were washed extensively with phosphate buffered saline (PBS) and collected by trypsinization for flow cytometric analysis of polymer uptake (detected by gating for FITC$^+$ cells), as shown in FIGS. 13A-13B. A significant reduction in the uptake of P3F (about 20%) and P5F (about 30%) was observed in the BV2 #106 cell line. No uptake was confirmed for the corresponding non-functionalized polymers (i.e., 3NF and 5NF) in both cell lines. Without being bound by theory, the incomplete abrogation of P3F and P5F uptake in the #106 cell line was expected, as the residual levels of TSPO expressed in #106 cells can still account for uptake of the polymers. Interestingly, for P3F the uptake was inhibited mainly at 4 hours of incubation; in contrast, the uptake of P5F was significantly inhibited only after 24 hours of incubation.

Without being bound by theory, differences in the affinity of P3F and P5F for TSPO receptor and/or in the dynamics of intracellular uptake may explain the discrepancies observed between the two polymers at different incubation time on the cells. Thus, a strategy was designed to assess the affinity of the polymers for TSPO.

Example 8. Assessment of Binding of PK11195-Conjugated Polymers to TSPO Receptor by Microscale Thermophoresis (MST)

Microscale thermophoresis (MST) is a technique that detects changes in the hydration shell of molecules in solutions, by measuring the movement of biomolecules along microscale temperature gradients created by very low-power infrared-lasers within thin glass capillaries filled with analyte. The solvation entropy and the hydration shell of the molecules is the driving force of this phenomenon. Any changes of the hydration shell, due to modification of the structure of the biomolecules and/or interaction with a binding partner, affects the thermophoretic movement and is used to determine binding affinities. The advantage of this technique is that the measurement can be performed in close-to-native, immobilization-free conditions. Without being bound by theory, this is very important when dealing with transmembrane receptors (such as TSPO) or bulky molecules (such as polymeric nanoparticles) whose functionality may be affected by immobilization on a flat surface (a step required by other techniques such as surface plasmon resonance).

Figure 14A:
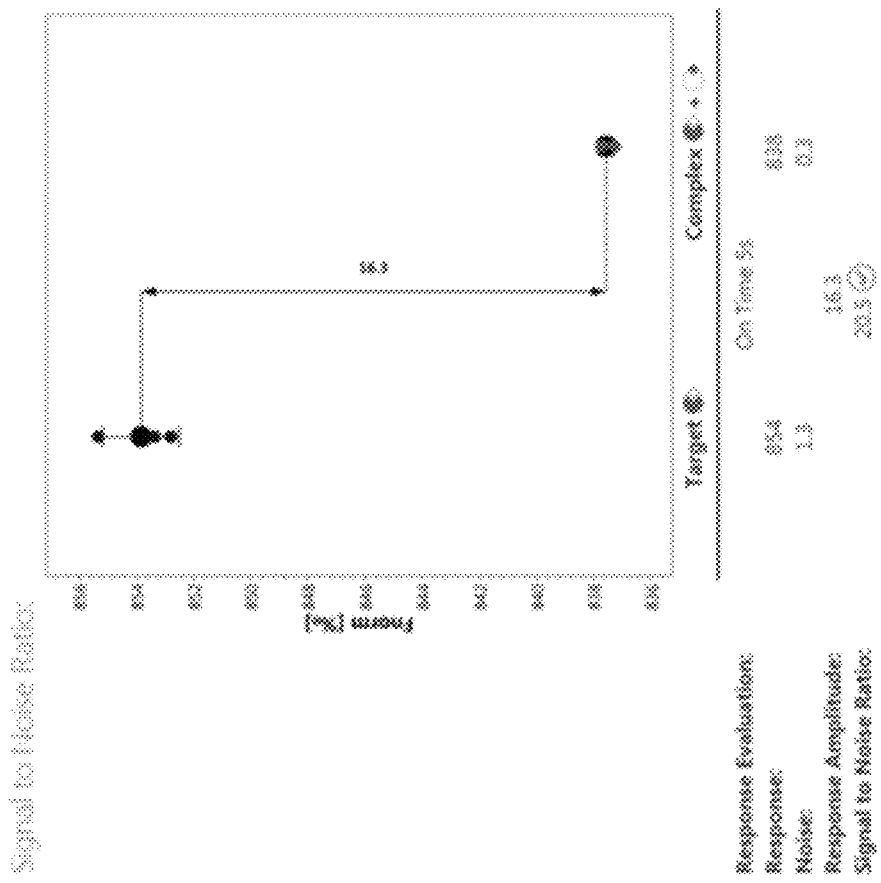
FIGS. 14A-14E depict binding as assessed by microscale thermophoresis (MST).
Figure 14B:
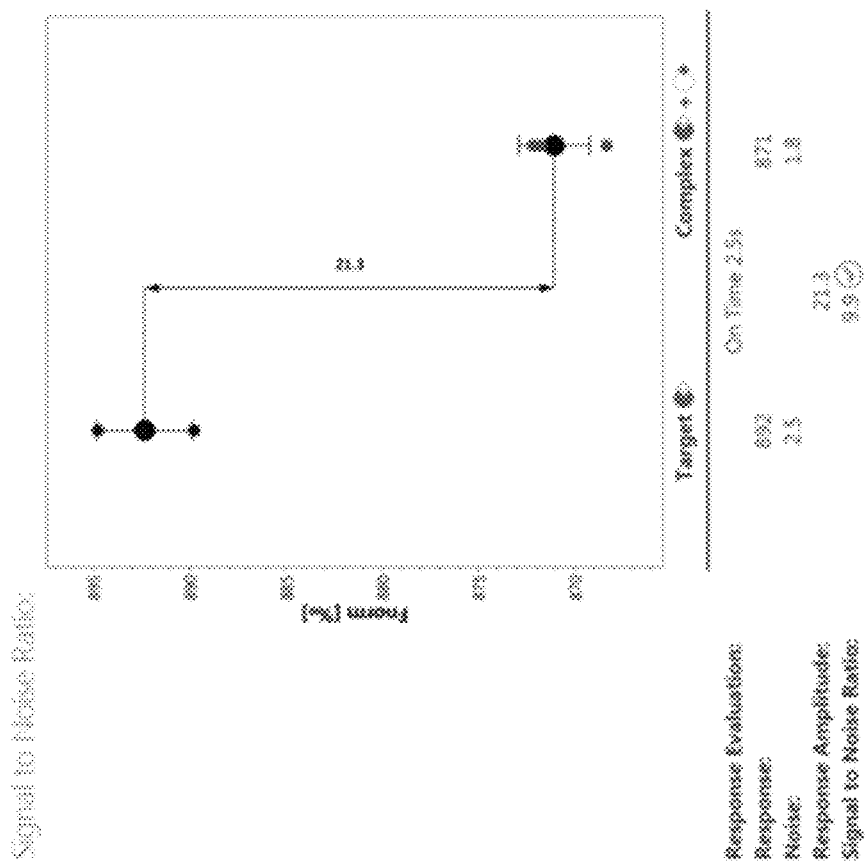
Figure 14C:
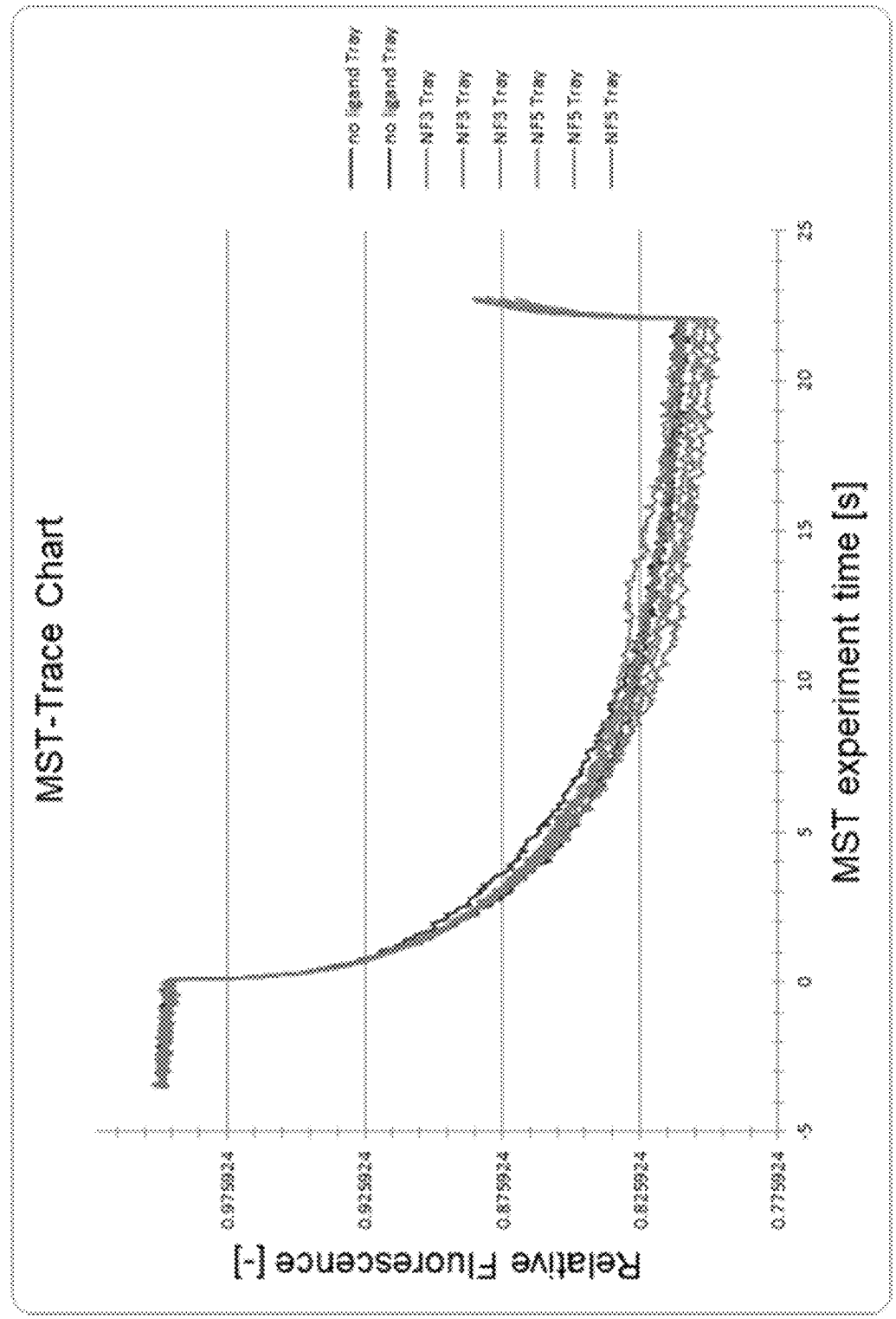
Figure 14D:
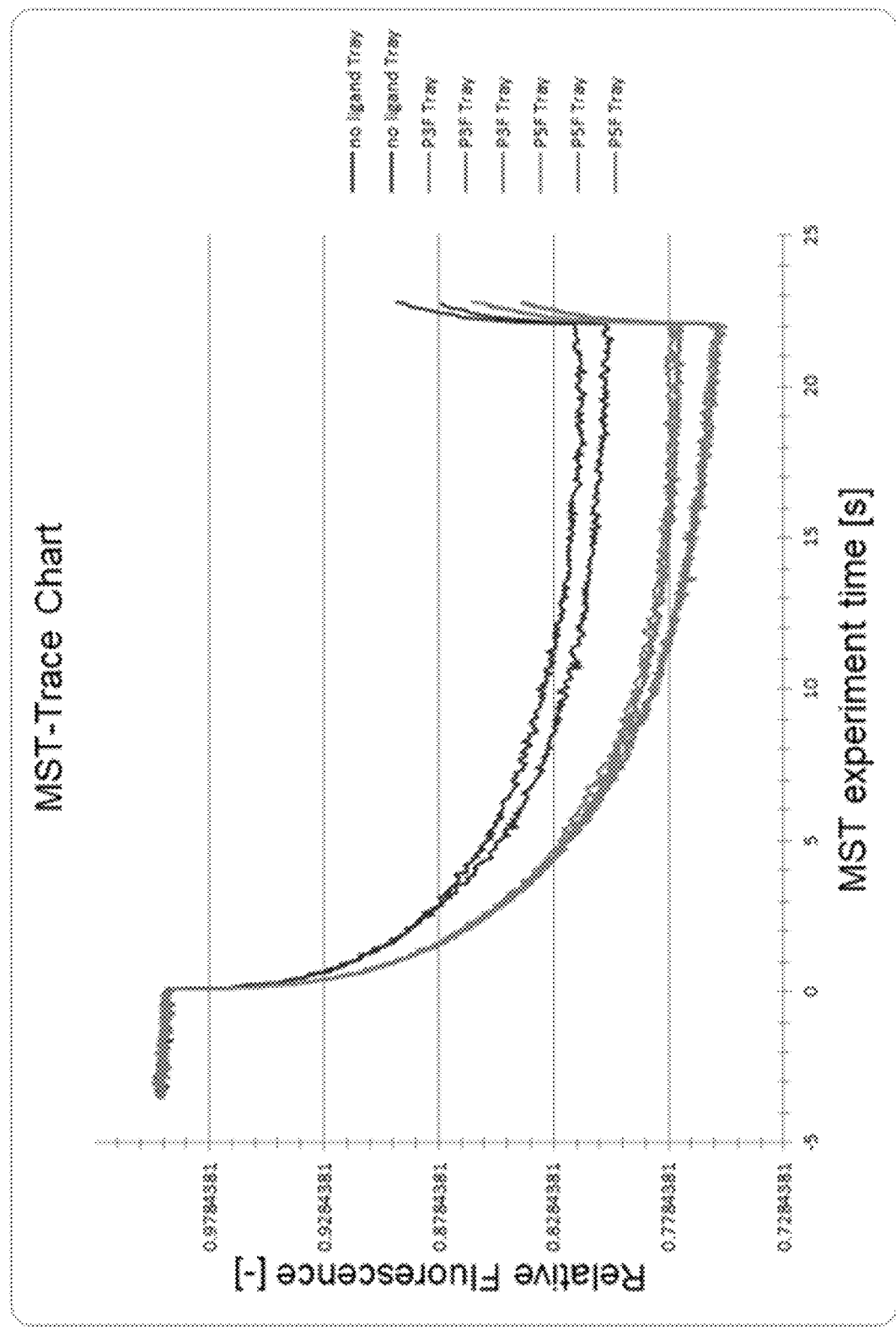
Figure 14E:
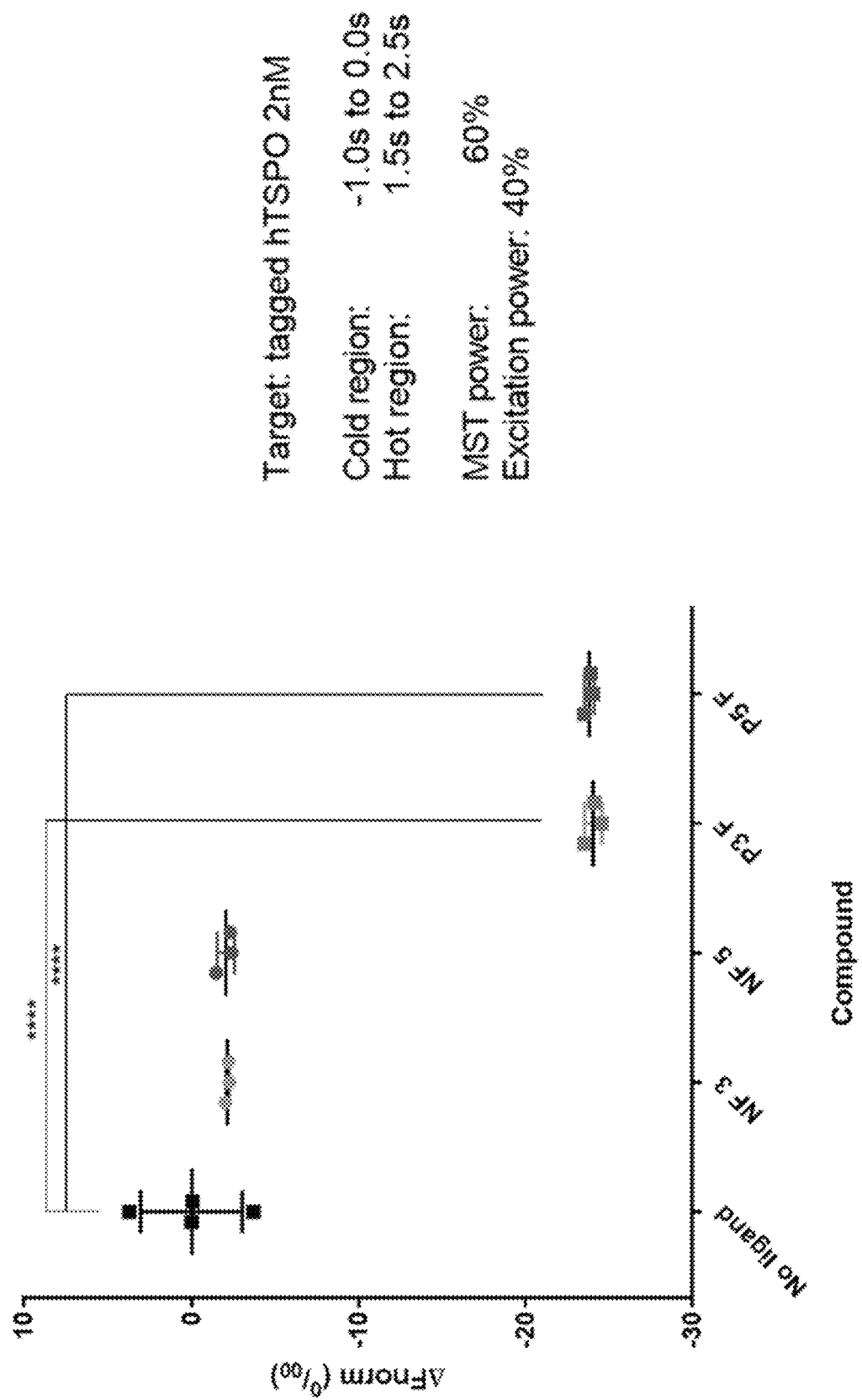

The tests were performed by using isolated human recombinant TSPO (purchased from LSBio). The lyophilized protein was resuspended in Tris buffer and stored at −80° C. as per manufacturer instructions. Labelling with a deep-red fluorophore was performed by using the Monolith labeling kit-RED from Nanothemper. Briefly, 200 nM of hTSPO was resuspended in Tris/Sarkosyl 0.1% buffer and then mixed with a solution containing anti-His red-fluorophore at 100 nM concentration. After incubation for 30 minutes at RT, the mixture was centrifuged at 15000 g for 10 minutes at 4° C., to pellet any aggregate or precipitate. For the assay, 5 nM red-tagged hTSPO was resuspended in TBS/DPC (12-dodecyl-phosphocoline) buffer and incubated with the free ligand PK11195 (tested at 250 µM) or PK11195-conjugated polymers P3F or P5F (tested at 500 µM). MST was then performed to assess binding. Non-functionalized polymers NFP3 and NFP5 were also tested to validate the specificity of interaction with TSPO. Binding of Ro5-4864 (500 µM), another TSPO selective ligand, was used as a quality check to demonstrate the capability of the MST assay to assess binding for TSPO. As shown in FIGS. 14A-14B, a significant change in the MST profile of tagged hTSPO was detected in the presence of PK11195 or Ro5-4864. Without being bound by theory, this confirms the ability to exploit this technique to monitor binding of specific ligands to the isolated receptor. Interestingly, the MST assay performed on hTSPO in the presence of the PK11195 functionalized polymers P3F and P5F (FIG. 14D) or the non-functionalized counterparts (FIG. 14C) highlighted binding of the functionalized polymers to the receptor, as evidenced by the significant change in the MST profile (FIG. 14E). This confirms that the covalent conjugation of polymers with a TSPO-selective ligand did not affect binding with the receptor.

Example 9. Synthesis and Characterization of MPC-PBR28 Conjugates

25MPC-4MePEG-N3 and 25MPC-8MePegN3 (FIG. 2) were polymerized through RAFT polymerization with the HemaC15 and HemaRhodamine. The compounds were dissolved in Methanol and heated to 65° for 24 hours under stirring after degassing. The block copolymer was then precipitated in diethyl ether. The Copper(I)-catalyzed Azide-Alkyne Cycloaddition (CuAAC) reaction was used to couple the copolymer with a modified PBR-28 alkyne precursor (FIG. 9B) to realize functionalized copolymers. Fourier-transform infrared spectroscopy (FTIR) was used to monitor the disappearance of the peak referred to N3 group from the sample as confirmation of the conjugation of the PBR-precursor to the polymer. The block copolymer so created was then nanoprecipitated to produce nanoparticles. Different batches were produced, with different PBR-ligand to NP molar ratios, as outlined in Table 4. In detail: i) NP-MPC batches with 6 units of PegN3 per MPC polymer (batches number #2_x, where x is a number between 1 and 2) will display more sites available for functionalization with PBR-click, as compared to NP-MPC batches carrying only 4 units of PegN3 per MPC polymer (batches number #1_x, where x is a number comprised between 1 and 2); ii) NP-MPC batches with 30 units of HemaCL5 per MPC polymer (batches number #x_1, where x is a number comprised between 1 and 2) will have a core that is less lipophilic than the NP-MPC batches with 60 units of HemaCL5 per MPC polymer (batches number #x_2, where x is a number comprised between 1 and 2).

TABLE 4

Chemical characteristics of produced MPC-PBR batches.

| Batch ID | Diameter (nm) | MPC (units/polymer) | PegN3 (units/polymer) | HemaCL5 (units/polymer) | Functionalization |
|---|---|---|---|---|---|
| MPC-PBR 2_1 | 100 | 25 | 6 | 30 | PBR-click |
| MPC-PBR 2_2 | 100 | 25 | 6 | 60 | PBR-click |
| MPC-PBR 1_1 | 100 | 25 | 4 | 30 | PBR-click |
| MPC-PBR 1_2 | 100 | 25 | 4 | 60 | PBR-click |
| MPC-NF 2_1 | 100 | 25 | 6 | 30 | none |
| MPC-NF 2_2 | 100 | 25 | 6 | 60 | none |
| MPC-NF 1_1 | 100 | 25 | 4 | 30 | none |
| MPC-NF 1_2 | 100 | 25 | 4 | 60 | none |

Figure 17A:
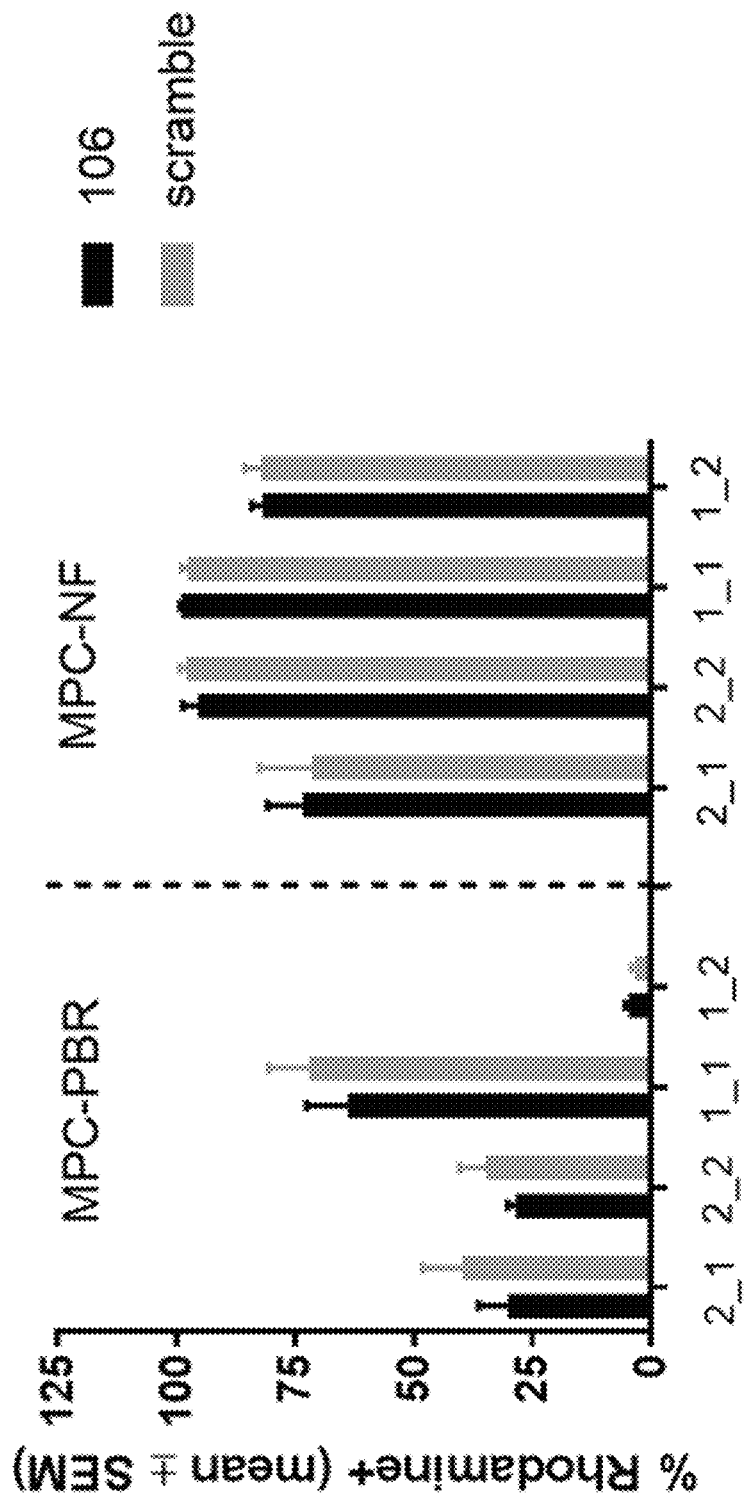
FIGS. 17A-17B depict flow cytometric evaluation of the uptake of NP-MPC, either functionalized with PBR-28 precursor (MPC-PBR) or not (MPC-NF) on BV2 cells lines expressing physiological levels (#scramble cell line) or about 20% of normal levels (#106 cell line) of TSPO.
Figure 17B:
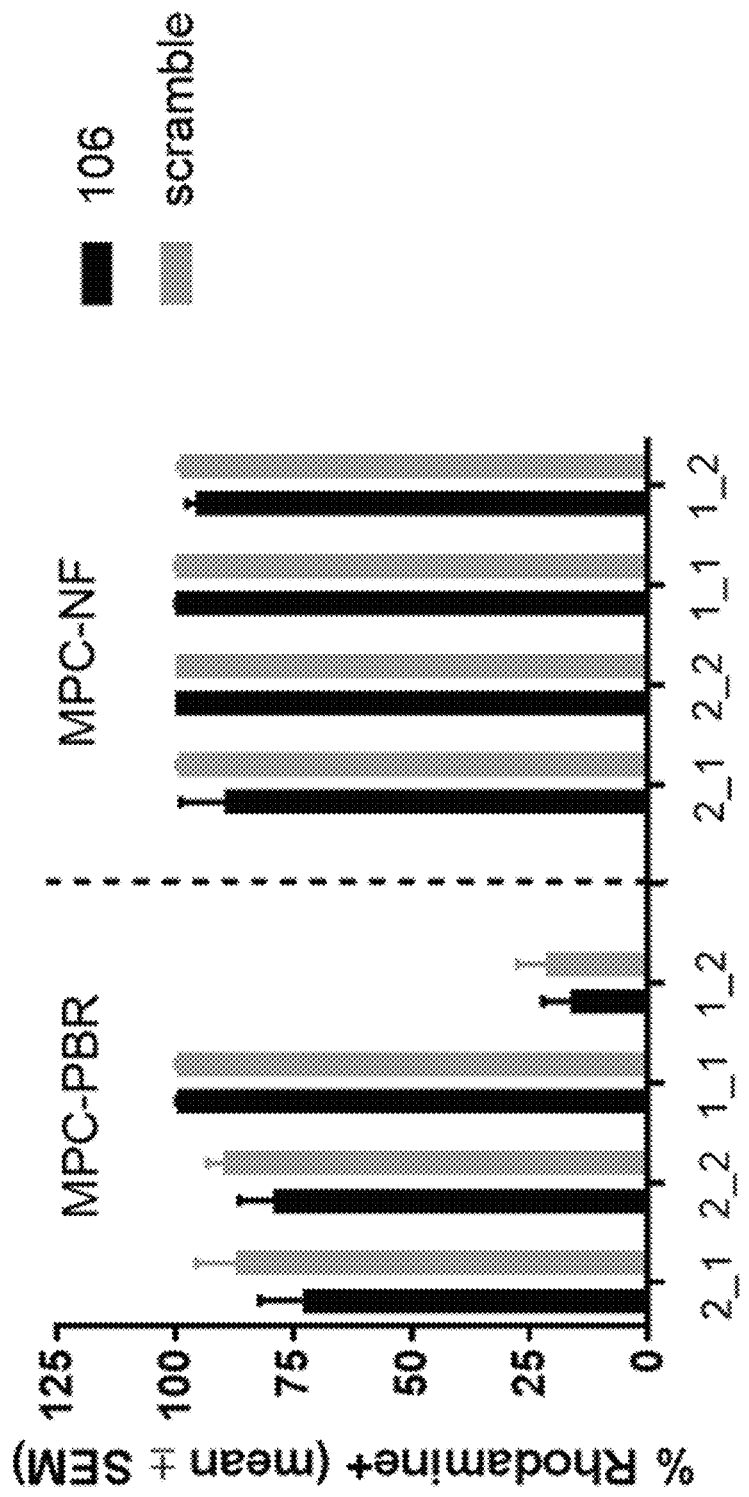

Ligand-dependent uptake was tested on BV2 microglia cell line to identify the formulation allowing best selectivity of uptake. NP-MPC, either functionalized with PBR-28 click precursor (MPC-PBR) or non-functionalized (MPC-NF), were added at different concentrations (in the range of 0.1-5.0 µg/ml) to the cell culture medium for 4 hours or 24 hours. Cells were collected and analyzed by flow cytometry to verify the uptake of the fluorescent labeled NPs. In line with what was observed for other non-functionalized NP-MPC (see FIG. 3A), a dose- and time-dependent increase of the uptake of both functionalized and non-functionalized NPs was observed (FIGS. 16A-16D). To verify whether the uptake of PBR-functionalized NPs is mediated by TSPO-receptor, the uptake of functionalized (MPC-PBR) versus non-functionalized (MPC-NF) NPs was compared in the context of a competitive pharmacological assay by co-incubating the functionalized NPs (tested at 5 µg/ml) with increasing concentrations (100, 200, and 400 µM) of free unconjugated TSPO ligand PBR28 for 4 hours. As shown in FIGS. 16E-16H, the uptake of all four MPC-PBR formulations was disrupted by co-incubation with increasing concentrations of the free ligand, with #2_2 displaying the best profile in terms of dose-response and selectivity, in comparison to the corresponding non-functionalized NP formulations. To further validate the selectivity for TSPO, uptake was tested in the BV2 #106 cell line (expressing only 20% of normal levels of TSPO), as previously described. Functionalized and non-functionalized NPs (5 µg/ml) were added to the cell culture medium and the uptake was analyzed by flow cytometry at 4 hours or 24 hours after treatment. As shown in FIGS. 17A-17B, a tendency to a reduction of the uptake was confirmed for NP-MPC functionalized batches #2_1 and #2_2 both at 4 hours and 24 hours of incubation in the BV2 #106 cell line. In contrast, no change in the uptake of any of the non-functionalized batches was detected. This supports an important role for the surface functionalization with PBR-click to allow the TSPO-dependent uptake of NPs batches #2_1 and #2_2.

Figure 20A:
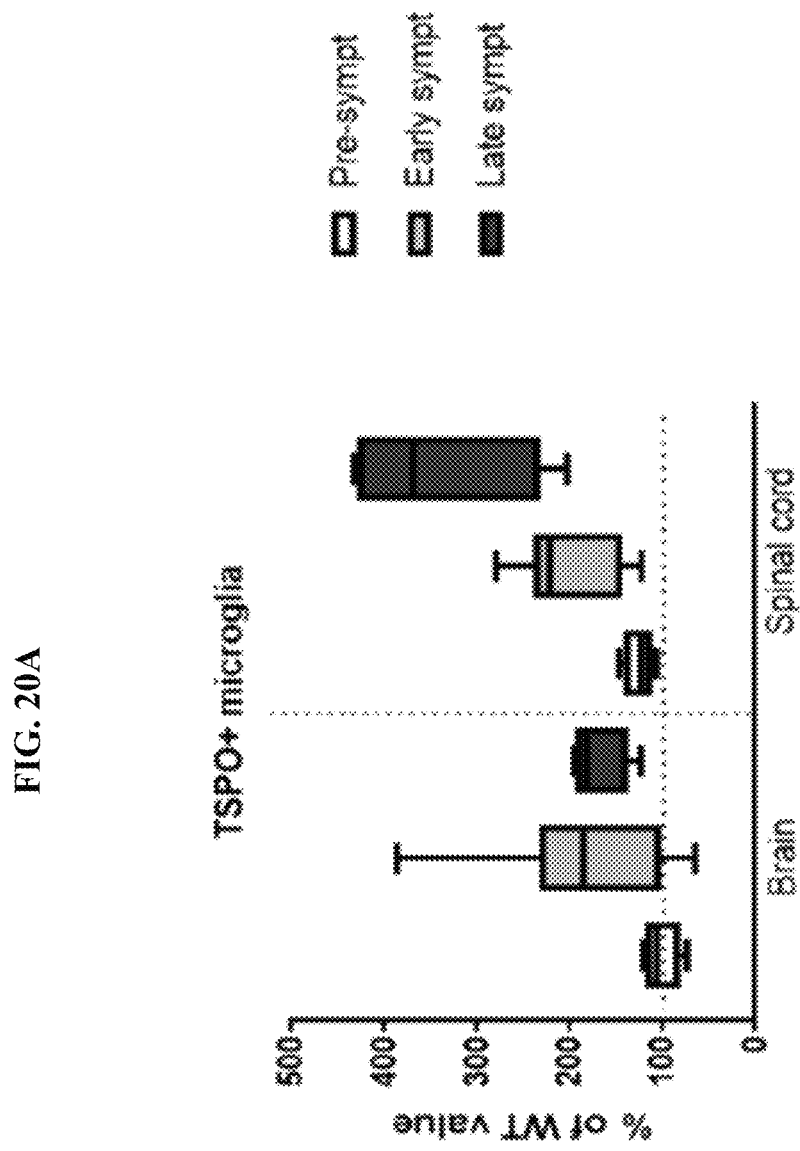
FIG. 20A depicts the progressive increase of the percentage of microglia cells stained positive for TSPO detected by flow cytometry in the brain and spinal cord of SOD1.G93A mouse model of ALS as the disease worsens.
Figure 20B:
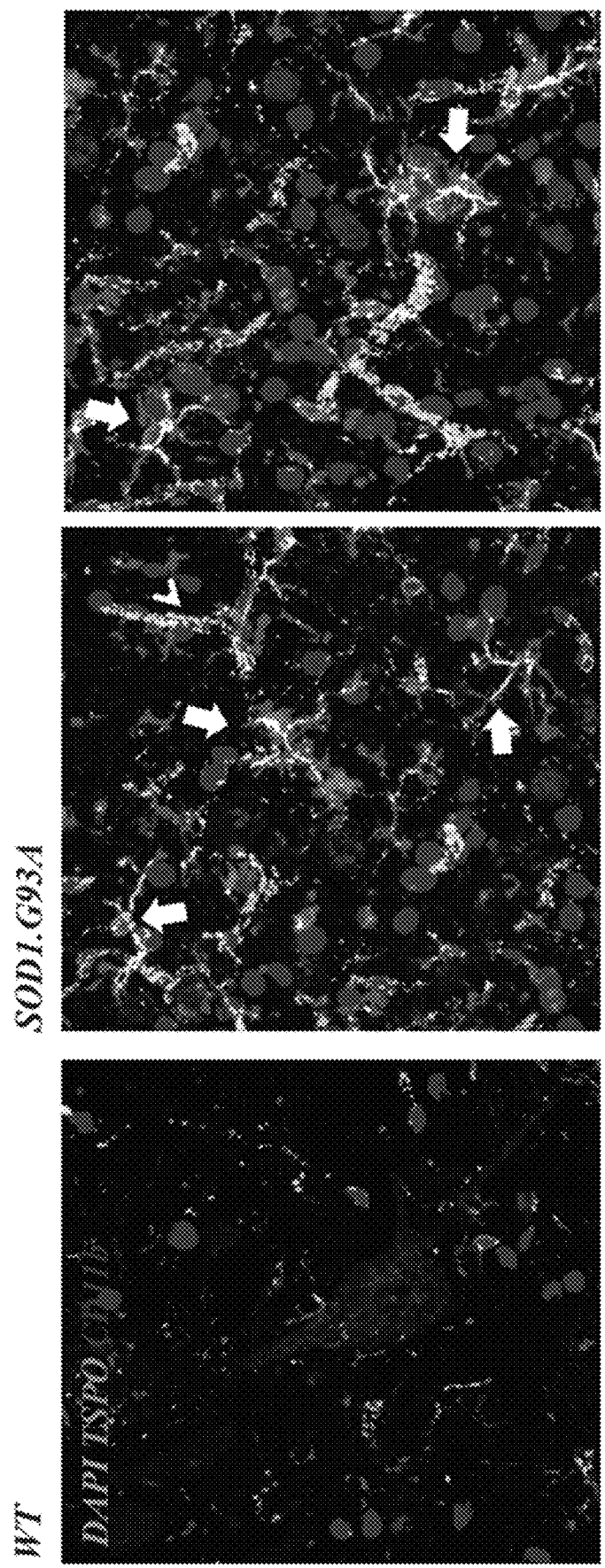
FIG. 20B depicts representative laser scanning confocal microscope images of reactive CD11$^+$ microglia cells showing increased staining for TSPO in the lumbar spinal cord of symptomatic SOD1.G93A mouse model of ALS (arrows in FIG. 20B).
Figure 20C:
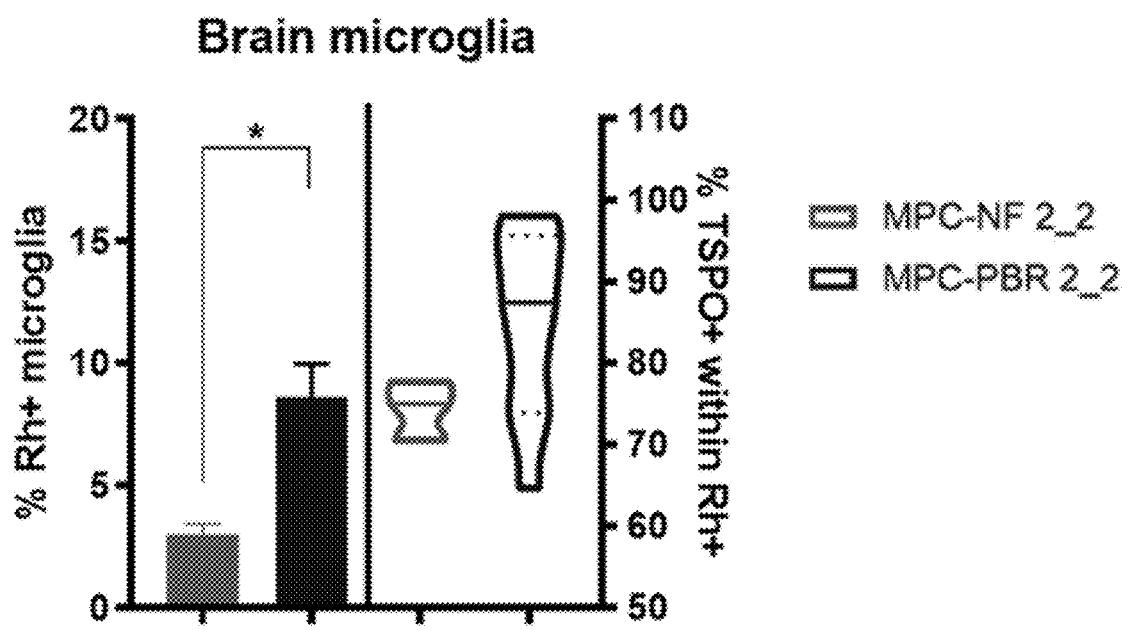
FIG. 20C depicts the extent of internalization of MPC-PBR 2_2 (MPC-NPs functionalized with a PBR28 precursor) or the corresponding not functionalized NPs, namely MPC-NF 2_2, in microglia cells retrieved from the brain of SOD1.G93A mouse model of ALS 3 days after NPs administration at lumbar level. The percentage of cells positive for TSPO (receptor for PBR28) within the rhodamine positive fraction is also depicted. *=p<0.05; Mann-Whitney test.
Figure 20D:
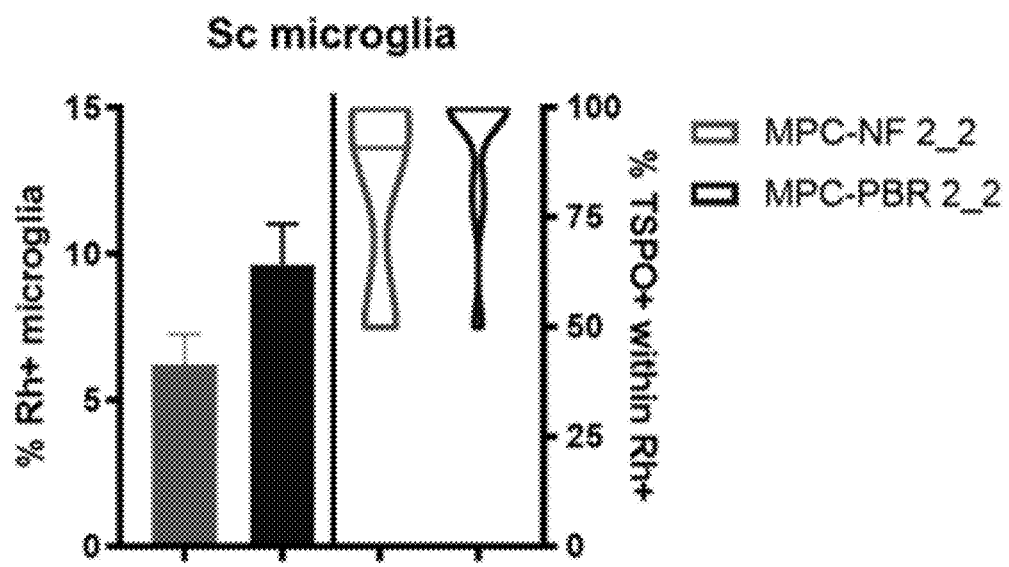
FIG. 20D depicts the extent of internalization of MPC-PBR 2_2 or MPC-NF 2_2 in microglia cells retrieved from the spinal cord of SOD1.G93A mouse model of ALS 3 days after NPs administration at lumbar level. The percentage of cells positive for TSPO within the rhodamine positive fraction is also depicted.

The functionalized MPC-PBR 2_2 and the corresponding not-functionalized MPC-NF 2_2 NPs were administered to symptomatic transgenic SOD1.G93A mice (a widely used mouse model of ALS) at the symptomatic stage of the disease (when TSPO is significantly upregulated in microglia cells throughout the brain and spinal cord, FIGS. 20A, 20B). As shown in FIGS. 20C and 20D, a higher uptake of the functionalized MPC-PBR 2_2 NPs is reported in brain and spinal cord. The majority of cells internalizing the NPs are TSPO$^+$, consistent with the increased targeting of TSPO$^+$ cells by functionalized MPC-NPs.

Overall, these experiments support the NP platform hereby described, which was designed to allow functionalization with receptor-targeted ligands, as a tool to achieve selective cellular uptake and multiple drug release.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents, publications, and accession numbers mentioned in this specification are herein incorporated by reference to the same extent as if each independent patent, publication, and accession number was specifically and individually indicated to be incorporated by reference.

What is claimed is:

1. A functionalized polymer comprising a first monomer: 2-Methacryloyloxyethyl phosphorylcholine (MPC), and a second monomer: methacrylate/amide polyethylene glycol (PEG) comprising an amine or azide covalently linked with a translocator protein (TSPO) ligand precursor having the structure:

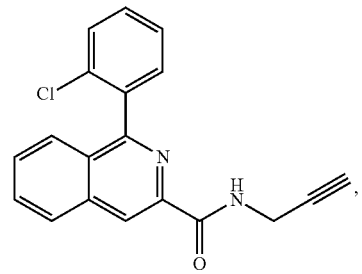

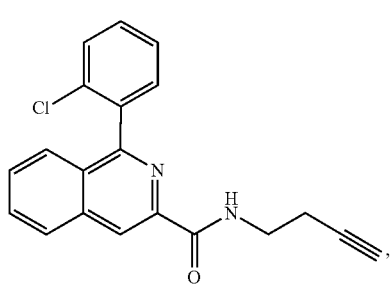

-continued

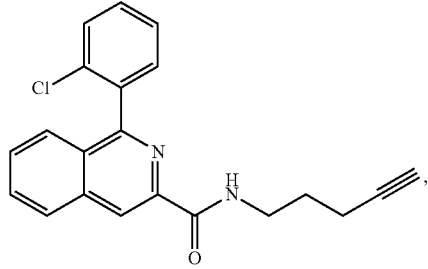

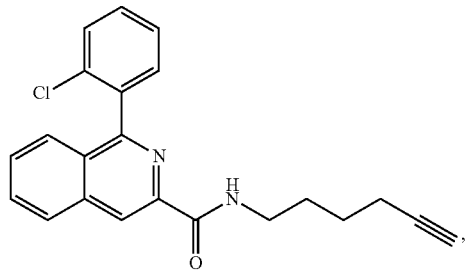

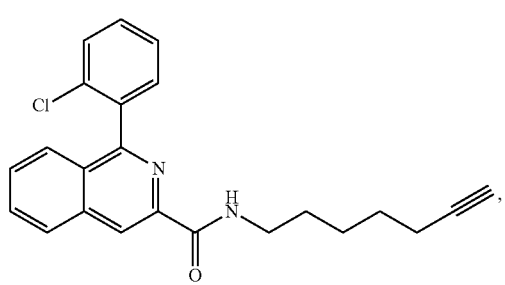

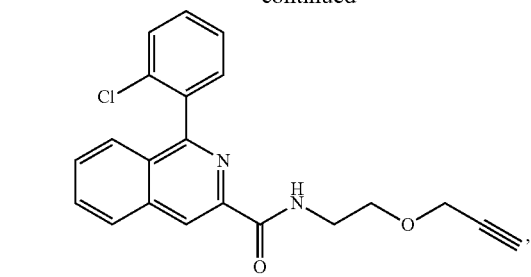
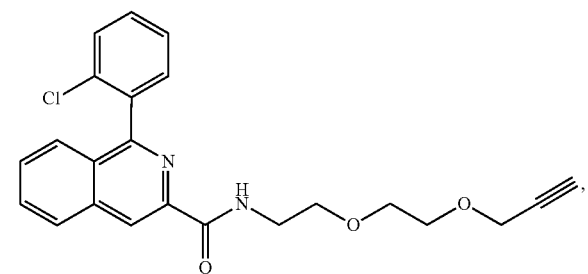
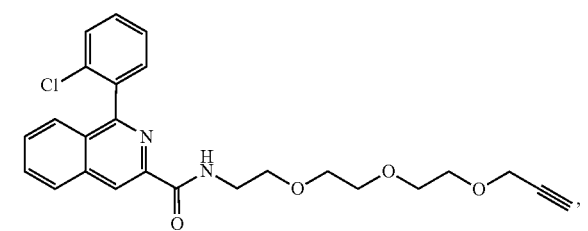
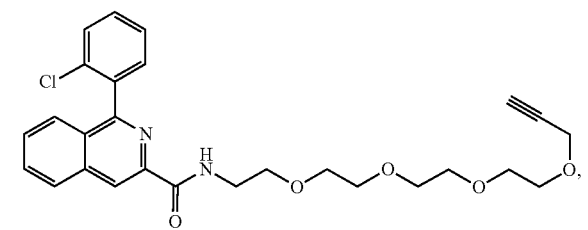
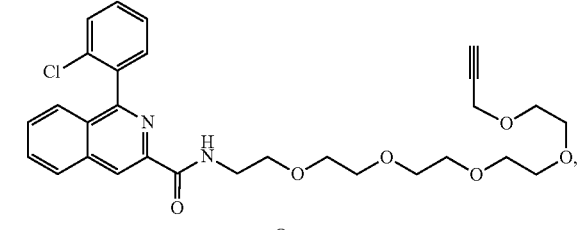
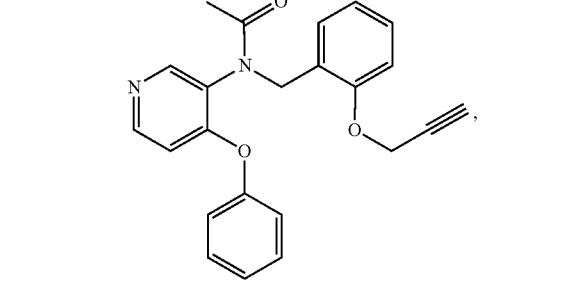
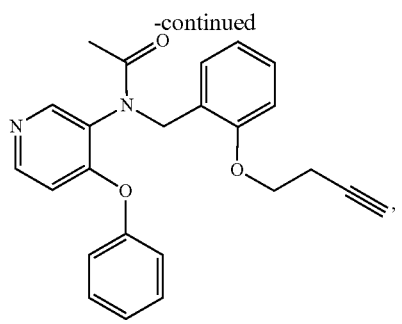
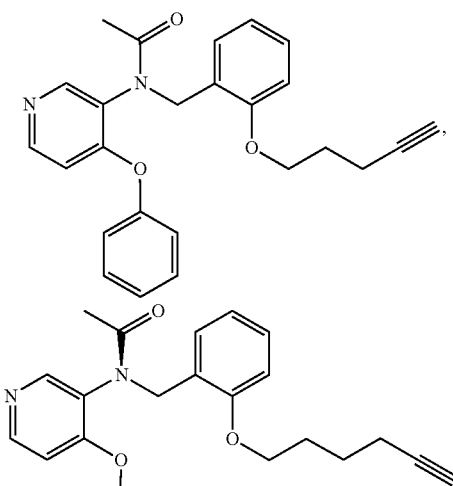
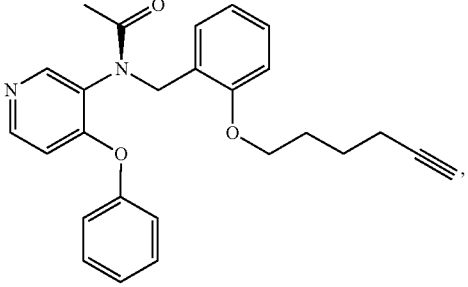
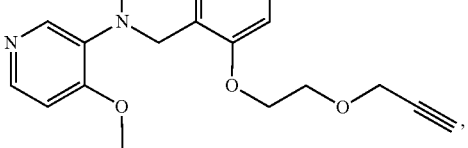
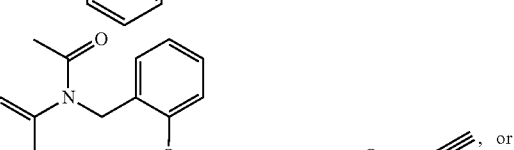
, or

2. The functionalized polymer of claim 1, wherein the molar ratio of the first monomer to the second monomer is about 25:3 to about 25:6.

3. The functionalized polymer of claim 1, further comprising a third monomer: hydroxyethyl methacrylate polycaprolactone (HEMA-PCL) comprising a functionalized carboxyl group.

4. The functionalized polymer of claim 1, wherein the monomers are polymerized using Reversible addition-fragmentation chain-transfer (RAFT) polymerization.

5. The functionalized polymer of claim 1, further comprising a hydroxyethyl methacrylate-rhodamine (HEMA-Rhodamine) monomer.

6. The functionalized polymer of claim 1, further comprising a hydroxyethyl methacrylate-succinate (HEMA-succinate) monomer.

7. The functionalized polymer according to claim 1, wherein the functionalized polymer consists of carboxyl end groups, the first monomer, the second monomer, and optionally a third monomer: hydroxyethyl methacrylate polycaprolactone (HEMA-PCL) having a carboxylic acid conjugated to a fluorescent labelled chain or radioligand for positron emission tomography (PET) imaging.

8. The functionalized polymer according to claim 1, wherein the functionalized polymer further comprises a third monomer: hydroxyethyl methacrylate polycaprolactone (HEMA-PCL) having a carboxylic acid conjugated to a fluorescent labelled chain or radioligand for positron emission tomography (PET) imaging.

9. The functionalized polymer according to claim 1, wherein the functionalized polymer is a block copolymer.

10. A nanoparticle obtained from the functionalized polymer of claim 1 optionally loaded with a therapeutic agent, detectable reporter, or combination thereof.

11. A method of targeting a cell comprising contacting the cell with the nanoparticle of claim 10 wherein the cell comprises a TSPO receptor and the TSPO ligand targets the TSPO receptor.

12. The nanoparticle according to claim 10, wherein the nanoparticle is loaded with iron.

13. A method of detecting a cell, the method comprising contacting the cell with the nanoparticle of claim 10 wherein the nanoparticle comprises a detectable reporter.

14. A method of delivering a therapeutic agent to a cell, the method comprising contacting the cell with the nanoparticle of claim 10 wherein the nanoparticle comprises the therapeutic agent.

15. A method of delivering a nucleic acid molecule to a cell, the method comprising contacting the cell with the nanoparticle of claim 10, wherein the nanoparticle comprises a nucleic acid molecule.

16. A method of treating neuroinflammation in a subject, the method comprising administering to the subject the nanoparticle of claim 10 wherein the functionalized polymer further comprises a third monomer: hydroxyethyl methacrylate-deferoxamine (HEMA-deferoxamine), wherein the deferoxamine is bound to Zirconium$^{89}$.

17. A method of treating neuroinflammation in a subject, the method comprising administering to the subject the nanoparticle of claim 10, wherein the nanoparticle comprises iron.

18. A method of treating cancer in a subject, the method comprising administering to the subject the nanoparticle of claim 10, wherein the nanoparticle comprises a chemotherapeutic agent selected from etoposide, busulfan, and lomustine.

* * * * *

UNITED STATES PATENT AND TRADEMARK OFFICE
CERTIFICATE OF CORRECTION

PATENT NO. : 12,161,663 B2
APPLICATION NO. : 17/035339
DATED : December 10, 2024
INVENTOR(S) : Marco Peviani et al.

It is certified that error appears in the above-identified patent and that said Letters Patent is hereby corrected as shown below:

In the Specification

Column 6, Line 19: Delete "Mill" and replace it with -- MRI --;

Column 6, Line 47: Delete "plglytggla" and replace it with -- plglytgqla --;

Column 19, Line 65: Delete "MM" and replace it with -- MRI --;

Column 19, Line 67: Delete "Mill" and replace it with -- MRI --;

Column 34, Line 67: Delete "HemaC15Q" and replace it with -- HemaCl5Q --;

Column 35, Line 54: Delete "HemaC15Q" and replace it with -- HemaCl5Q --;

Column 36, Line 67: Delete "HEMA-CLSQ" and replace it with -- Hema-CL5Q --;

Column 38, Line 17: Delete "MM" and replace it with -- MRI --;

Column 38, Line 45: Delete "HemaC15" and replace it with -- HemaCl5 --.

Signed and Sealed this
Nineteenth Day of August, 2025

Coke Morgan Stewart
*Acting Director of the United States Patent and Trademark Office*